US011771737B2

United States Patent
Greten et al.

(10) Patent No.: US 11,771,737 B2
(45) Date of Patent: Oct. 3, 2023

(54) TREATING OR PREVENTING ADVERSE LIVER CONDITIONS

(71) Applicant: The United States of America, as represented by the Secretary, Department of Health and Human Services, Bethesda, MD (US)

(72) Inventors: Tim F. Greten, Columbia, MD (US); Chi Ma, Olney, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 429 days.

(21) Appl. No.: 16/756,926

(22) PCT Filed: Oct. 29, 2018

(86) PCT No.: PCT/US2018/057946
§ 371 (c)(1),
(2) Date: Apr. 17, 2020

(87) PCT Pub. No.: WO2019/084535
PCT Pub. Date: May 2, 2019

(65) Prior Publication Data
US 2021/0138028 A1    May 13, 2021

Related U.S. Application Data

(60) Provisional application No. 62/578,176, filed on Oct. 27, 2017.

(51) Int. Cl.
A61K 38/14 (2006.01)
A61P 1/16 (2006.01)
(Continued)

(52) U.S. Cl.
CPC .......... *A61K 38/14* (2013.01); *A61K 31/4985* (2013.01); *A61K 31/575* (2013.01);
(Continued)

(58) Field of Classification Search
None
See application file for complete search history.

(56) References Cited

U.S. PATENT DOCUMENTS

2017/0296481 A1    10/2017    Bae et al.

OTHER PUBLICATIONS

Frankel et al. Metagenomic Shotgun Sequencing and Unbiased Metabolomic Profiling Identify Specific Human Gut Microbiota and Metabolites Associated with Immune Checkpoint Therapy Efficacy in Melanoma Patients. Neoplasia (2017) 19, 848-855 (Year: 2017).*

(Continued)

*Primary Examiner* — Joanne Hama
*Assistant Examiner* — Miles Joseph Delahoussaye
(74) *Attorney, Agent, or Firm* — Leydig, Voit & Mayer, Ltd.

(57) ABSTRACT

In embodiments, the invention provides a method of treating or preventing an adverse condition of the liver of a mammal, the method comprising administering to the mammal an effective amount of vancomycin and a checkpoint inhibitor. In embodiments, the invention provides a method of treating or preventing an adverse condition of the liver of a mammal, the method comprising administering to the mammal an effective amount of a primary bile acid.

13 Claims, 108 Drawing Sheets

(51) Int. Cl.
- A61P 35/00 (2006.01)
- A61K 31/4985 (2006.01)
- A61K 31/575 (2006.01)
- A61K 39/395 (2006.01)
- C07K 16/28 (2006.01)
- A61K 39/00 (2006.01)

(52) U.S. Cl.
CPC .......... *A61K 39/39541* (2013.01); *A61P 1/16* (2018.01); *A61P 35/00* (2018.01); *C07K 16/2818* (2013.01); *A61K 2039/505* (2013.01); *C07K 2317/76* (2013.01)

(56) References Cited

OTHER PUBLICATIONS

Pellicciari et al. Farnesoid X Receptor: From Structure to Potential Clinical Applications. Journal of Medicinal Chemistry, 2005, 48(17) 5383-5403 (Year: 2005).*
Tosello-Trampont et al. Immunoregulatory Role of NK cells in Tissue Inflammation and Regeneration. Front. Immunol. 8:301 (Year: 2017).*
Dapito et al. Promotion of Hepatocellular Carcinoma by the Intestinal Microbiota and TL4. Cancer Cell 21, 504-516 (Year: 2012).*
Bektas et al. The effects of tadalafil and pentoxifylline on apoptosis and nitric oxide synthase in liver ischemia/reperfusion injury. Kaohsiung Journal of Medical Sciences (2016) 32, 339-347 (Year: 2016).*
Bilal at al. Histological changes in the liver of diabetic rats: A review of pathogenesis of nonalcoholic fatty liver disease in type 1 diabetes mellitus, Cogent Medicine, 3:1, 1275415 (Year: 2016).*
Ventura et al. Improvement of water solubility and dissolution rate of ursodeoxycholic acid and chenodeoxycholic acid by complexation with natural and modified β-cyclodextrins. International Journal of Pharmaceutics 149 (1997) 1-13 (Year: 1997).*
Loo et al Gut Microbiota Promotes Obesity-Associated Liver Cancer through PGE2-mediated Suppression of Antitumor Immunity Cancer Discov (2017) 7 (5): 522-538 (Year: 2017).*
Wang et al Bile Acid Receptors and Liver Cancer Curr Pathobiol Rep (2013) 1:29-35 (Year: 2013).*
Califano et al. Tadalafil Augments Tumor Specific Immunity in Patients with Head and Neck Squamous Cell Carcinoma Clin Cancer Res (2015) 21(1):30-38 (Year: 2015).*
Wan et al Myeloid Cells in Hepatocellular Carcinoma Hepatology (2015) 62(4):1304-1312 (Year: 2015).*
Atarashi et al., "Induction Of Colonic Regulatory T Cells By Indigenous Clostridium Species," *Science*, 331: 334-341 (2011).
Bhowmik et al., "Structure and Functional Characterization Of A Bile Acid 7alpha Dehydratase Baie In Secondary Bile Acid Synthesis," *Proteins*, 84(3): 316-331 (2016) Author Manuscript published online in PubMed.
Briz et al., "Usefulness of Liposomes Loaded with Cytostatic Bile Acid Derivatives to Circumvent Chemotherapy Resistance of Enterohepatic Tumors," *Molecular Pharmacology*, 63(3): 742-750 (2003).
Buffie et al., "Precision Microbiome Reconstitution Restores Bile Acid Mediated Resistance To Clostridium Difficile," *Nature*, 517(7533): 205-208 (2015) Author Manuscript published online in PubMed.
Califano et al., "Tadalafil Augments Tumor Specific Immunity in Patients with Head and Neck Squamous Cell Carcinoma," *Clin Cancer Res*, 21(1): 30-38 (Jan. 1, 2015).
Caporaso et al., "QIIME Allows Analysis Of High-Throughput Community Sequencing Data," *Nat. Methods*, 7(5): 335-336 (2010) Author Manuscript published online in PubMed.
Chaisaingmongkol et al., "Common Molecular Subtypes Among Asian Hepatocellular Carcinoma and Cholangiocarcinoma," *Cancer Cell*, 32: 57-70 (2017) epub Jun. 22, 2017.
Chretien et al., "Bile Acid Glycine and Taurine Conjugates in Serum of Patients with Primary Biliary Cirrhosis: Effect of Ursodeoxycholic Treatment," *Gut*, 30:1110-1115 (1989).

Dapito et al., "Promotion of Hepatocellular Carcinoma by the Intestinal Microbiota and TLR4," *Cancer Cell*, 21:504-516 (2012).
Desantis et al., "Greengenes, a Chimera-Checked 16S rRNA Gene Database and Workbench Compatible with ARB," *Appl. Environ. Microbiol.*, 72(7): 5069-5072 (Jul. 2006).
Eggert et al., "Distinct Functions of Senescence-Associated Immune Responses in Liver Tumor Surveillance and Tumor Progression," *Cancer Cell*, 30(4): 533-547 (Oct. 10, 2016).
El-Khoueiry et al., "Nivolumab in Patients With Advanced Hepatocellular Carcinoma (Checkmate 040): An Open-Label, Non-Comparative, Phase 1/2 Dose Escalation And Expansion Trial," *Lancet*, 389: 2492-2502 (2017).
European Patent Office, International Search Report and Written Opinion of the International Searching Authority, dated Jul. 18, 2019, in International Application No. PCT/US2018/057946, 18 pages.
Frankel et al., "Metagenomic Shotgun Sequencing and Unbiased Metabolomic Profiling Identify Specific Human Gut Microbiota and Metabolites Associated with Immune Checkpoint Therapy, Efficacy in Melanoma Patients," *Neoplasia*, 19(10): 848-855 (Oct. 2017).
Gonzales et al., "Oral Cholic Acid for Hereditary Defects of Primary Bile Acid Synthesis: A Safe and Effective Long-Term Therapy," *Gatroenterology*, 137: 1310-1320 (2009).
Hassel et al., "Tadalafil has Biologic Activity in Human Melanoma. Results of a Pilot Trial with Tadalafil in Patients with Metastatic Melanoma (TaMe)," *OncoImmunology*, 6(9): 1-10 (2007).
Iida et al., "Commensal Bacteria Control Cancer Response to Therapy by Modulating the Tumor Microenvironment," *Science*, 342(6161): 967-970 (2013).
Kudo, "Immune Checkpoint Inhibition in Hepatocellular Carcinoma: Basics and Ongoing Clinical Trials," *Oncology*, 92(supp 1): 50-62 (2017).
Lee et al., "Steady State Production Of IL-4 Modulates Immunity In Different Strains And Is Determined By Lineage Diversity Of Inkt Cells," *Nat. Immunol.*, 14(11): 1146-1154 (2013).
Ma et al., "Gut Microbiome-mediated Bile Acid Metabolism Regulates Liver Cancer Via NKT Cells," *Science*, 360 (6391): 1-9 (2018).
Ma et al., "Gut Microbiome-mediated Bile Acid Metabolism Regulates Liver Cancer Via NKT Cells," *Science*, 360 (876): 1 page (2018) Research Article Summary.
Ma et al., "NAFLD Causes Selective CD4(+) T Lymphocyte Loss and Promotes Hepatocarcinogenesis," *Nature*, 531(7593): 253-257 (2016) Author Manuscript published online in PubMed.
Ma et al., "Anti-Gr-1 Antibody Depletion Fails To Eliminate Hepatic Myeloid-Derived Suppressor Cells In Tumor-Bearing Mice," *J. Leukoc. Biol.*, 92: 1199-1206 (2012).
Ridlon et al., "Bile Acids and the Gut Microbiome," *Current Opinion—Gastroenterology*, 30(3): 332-338 (May 2014).
Ridlon et al., "Bile Salt Biotransformations By Human Intestinal Bacteria," *Journal of Lipid Res*, 47: 241-259 (2006).
Roderburg et al., "The Role of the Gut Microbiome in the Development and Progression of Liver Cirrhosis and Hepatocellular Carcinoma," *Gut Microbes*, 5(4): 441-445 (2014) doi: 10.4161/gmic.29599. Epub Jul. 9, 2014.
Sayim et al., "Gut Microbiota Regulates Bile Acid Metabolism by Reducing the Levels of Tauro-Beta-Muricholic Acid, a Naturally Occurring FXR Antagonist," Cell Metab. 17(2): 225-235 (Feb. 5, 2013).
Shramm, "Bile Acids, the Microbiome, Immunity, and Liver Tumors," *N Engl J Med*, 379(9): 888-890 (Aug. 30, 2018).
Smyth et al., "Differential Tumor Surveillance by Natural Killer (Nk) and Nkt Cells," *J. Exp. Med.*, 191(4): 661-668 (2000).
Staley et al., "Interaction of Gut Microbiota With Bile Acid Metabolism and Its Influence on Disease States," *App Microbiol. Biotechnol.*, 101(1): 47-64 (Jan. 2016) epub Nov. 25, 2016.
Theriot et al., "Antibiotic-Induced Alterations of the Gut Microbiota Alter Secondary Bile Acid Production and Allow for Clostridium difficile Spore Germination and Outgrowth in the Large Intestine," *mSphere* 1(1): 1-16 (Jan.-Feb. 2016).
Vrieze et al., "Impact of Oral Vancomycin on Gut Microbiota, Bile Acid Metabolism, and Insulin Sensitivity," *Journal of Hepatology*, 60: 824-831 (2014).

(56) References Cited

OTHER PUBLICATIONS

Wang et al., "Naive Bayesian Classifier for Rapid Assignment of rRNA Sequences Into the New Bacterial Taxonomy," *Appl. Environ. Microbiol.*, 73(16): 5261-5267 (2007).

Wang et al., "Bifidobacterium can Mitigate Intestinal Immunopathology in the Context of CTLA-4 Blockade," *PNAS*, 115(1): 157-161 (Jan. 2, 2018).

Weed et al., "Tadalafil Reduces Myeloid-Derived Suppressor Cells And Regulatory T Cells And Promotes Tumor Immunity In Patients With Head And Neck Squamous Cell Carcinoma," *Clin Cancer Research*, 21(1):39-48 (2015) Author Manuscript published online in PubMed.

Yasuda et al., "Intestinal Perforation After Nivolumab Immunotherapy for a Malignant Melanoma: A Case Report," *Surgical Case Reports*, 3(94): 1-4 (2017).

Yoshimoto et al., "Obesity-Induced Gut Microbial Metabolite Promotes Liver Cancer Through Senescence Secretome," *Nature*, 499(7456): 97-101 (2013) epub Jun. 26, 2013.

Yu et al., The gut microbiome and liver cancer: mechanisms and clinical translation. Nat Rev Gastroenterol Hepatol. Sep. 2017;14(9):527-539. doi: 10.1038/nrgastro.2017.72. Epub Jul. 5, 2017.

Zhang et al., "Effects Of Feeding Bile Acids And A Bile Acid Sequestrant On Hepatic Bile Acid Composition In Mice," *J Lipid Res* 51(11): 3230-3242 (2010).

\* cited by examiner

TREATING OR PREVENTING ADVERSE LIVER CONDITIONS

CROSS-REFERENCE TO RELATED APPLICATIONS

This patent application is a U.S. National Phase of International Patent Application No. PCT/US2018/057946, filed Oct. 29, 2018, which claims the benefit of U.S. Provisional Patent Application No. 62/578,176, filed Oct. 27, 2017, each of which is incorporated by reference herein in its entirety.

STATEMENT REGARDING FEDERALLY SPONSORED RESEARCH AND DEVELOPMENT

This invention was made with Government support under project number ZIA BC 011345 by the National Institutes of Health, National Cancer Institute. The Government has certain rights in the invention.

BACKGROUND OF THE INVENTION

The gut microbiome is emerging as a factor regulating anti-tumor immunity, controlling the efficacy of chemo- and immunotherapies. The liver is exposed to bacterial components and metabolites via the portal vein. Profound effects of the gut microbiome on hepatocellular carcinoma (HCC) development have been described. Secondary hepatic malignancies (liver metastases) account for 95% of all hepatic malignancies, and liver is the most common site for organ metastasis in the body.

There is an unmet need of controlling metastasis and improving anti-tumor immunity in the liver.

BRIEF SUMMARY OF THE INVENTION

In embodiments, the invention provides a method of treating or preventing an adverse condition of the liver of a mammal, the method comprising administering to the mammal an effective amount of vancomycin and a checkpoint inhibitor.

In embodiments, the invention provides a method of treating or preventing an adverse condition of the liver of a mammal, the method comprising administering to the mammal an effective amount of a primary bile acid.

DETAILED DESCRIPTION OF THE INVENTION

Figure 1A:
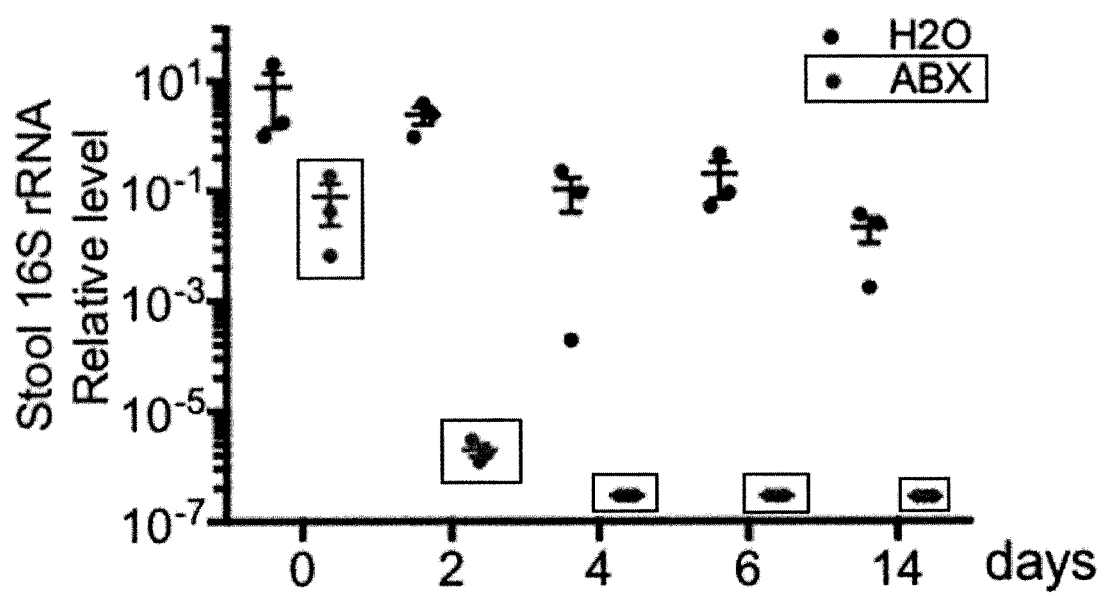
FIG. 1A is a dot plot showing the quantified efficacy of an antibody cocktail of vancomycin, neomycin, and primaxin (ABX) to remove gut bacteria as measured by quantifying stool bacterial load using real-time PCR to detect the 16S rRNA gene.

In embodiments, the invention provides a method of treating or preventing an adverse condition of the liver of a mammal, the method comprising administering to the mammal an effective amount of vancomycin and a checkpoint inhibitor. In embodiments, the checkpoint inhibitor is administered simultaneously with the administration of the vancomycin. In embodiments, the checkpoint inhibitor is administered sequentially with (e.g., before or after) the administration of the vancomycin.

In embodiments, the method comprises administering to the mammal an effective amount of a phosphodiesterase type 5 (PDE5) inhibitor. In embodiments, the PDE5 inhibitor is administered simultaneously with the administration of the vancomycin or checkpoint inhibitor. In embodiments, the PDE5 inhibitor is administered sequentially with (e.g., before or after) the administration of the vancomycin or checkpoint inhibitor. In embodiments, the PDE5 inhibitor is tadalafil, avanafil, lodenafil, mirodenafil, sildenafil, vardenafil, udenafil, zaprinast, benzamidenafil, and dasantafil. In embodiments, the PDE5 inhibitor is tadalafil.

In embodiments, the method comprises administering to the mammal an effective amount of a primary bile acid. In embodiments, two, three, or all of the vancomycin, checkpoint inhibitor, PDE5 inhibitor, and primary bile acid are in a single composition.

In embodiments, the invention provides a method of treating or preventing an adverse condition of the liver of a mammal, the method comprising administering to the mammal an effective amount of a primary bile acid. In embodiments, the primary bile acid is formulated for direct absorption by the intestine, formulated for protection from intestinal enzymes, or both.

In embodiments, the checkpoint inhibitor is pembrolizumab, nivolumab, atezolizumab, avelumab, durvalumab, or ipilimumab. In embodiments, the checkpoint inhibitor is a programmed death 1 (PD-1) inhibitor. In embodiments, the PD-1 inhibitor is pembrolizumab or nivolumab. In embodiments, the PD-1 inhibitor is nivolumab. In embodiments, the checkpoint inhibitor is an indoleamine (2,3)-dioxygenase (IDO) inhibitor. In embodiments, the inhibitor is epacadostat, indoximod, BMS-986205, NLG802, or HTI-1090.

In embodiments, the primary bile acid is administered in combination with a substance that inhibits immunosuppression, a substance that elicits an immune response, or both. In embodiments, the substance is anti TGF-beta or anti IL-10. In embodiments, the substance is a checkpoint inhibitor, e.g., those as described above.

In embodiments, the substance is a tumor vaccine. In embodiments, the vaccine is an AFP peptide, a DC pulsed AFP peptide, or an NY-ESO-1 peptide. In embodiments, the substance is a chemotherapeutic compound. In embodiments, the chemotherapeutic compound is abraxane, amsacrine, azacitidine, bendamustine, bleomycin, busulfan, cabazitaxel, capecitabine, carboplatin, carmustine, chlorambucil, cisplatin, 5FU, cladribine, clofarabine, crisantaspase, cyclophosphamide, cytarabine, dacarbazine, dactinomycin, daunorubicin, docetaxel, doxorubicin, epirubicin, eribulin, etoposide, FLAG-Ida, fludarabine, fluorouracil, gemcitabine, hydroxycarbamide, idarubicin, ifosfamide, irinotecan, leucovorin, liposomal daunorubicin, liposomal doxorubicin, melphalan, mercaptopurine, mesna, methotrexate, mitomycin, mitotane, mitoxantrone, oxaliplatin, paclitaxel, pemetrexed, pentostatin, pertuzumab, procarbazine, raltitrexed, rasburicase, streptozocin, temozolomide, thiotepa, tioguanine, topotecan, trabectedin, treosulfan, trifluridine-tipiracil hydrochloride, vinblastine, vincristine, vindesine, or vinorelbine.

In embodiments, the primary bile acid is formulated for protection from intestinal enzymes. In embodiments, the protection prevents or reduces dehydroxylation by a dehydroxylase. In embodiments, the formulation comprises lactulose, wheat bran, NAD+, or NADH.

In embodiments, the adverse condition is tumor growth, tumor metastasis, or autoimmune disease. In embodiments, the adverse condition is autoimmune disease. In embodiments, the autoimmune disease is Type 1 diabetes, allergic encephalomyelitis, arthritis, systemic lupus erythematosus, inflammatory colitis, or Graves's thyroiditis. In embodiments, the adverse condition is liver metastasis or hepatocellular carcinoma (HCC). In embodiments, the adverse condition is colorectal, lung, breast, pancreatic, stomach, melanoma, or neuroendocrine cancer. In embodiments, the adverse condition comprises metastasis of one or more of these conditions into the liver.

In embodiments, the method is a method of treating the adverse condition. In embodiments, the method is a method of preventing the adverse condition.

In embodiments, the primary bile acid is taurocholic acid (TCA), β-muricholic acid (β-MCA), tauro-β-muricholic acid (T-β-MCA), or chenodeoxycholic acid (CDCA).

In embodiments, the administration is intravenous. In embodiments, the administration is via the portal vein.

In embodiments, the administration of the primary bile acid reduces the presence of a species of the gut microbiome, wherein the species inhibits expansion of hepatic cells that express CXCR6. In embodiments, the hepatic cells that express CXCR6 are hepatic NKT cells. In embodiments, the hepatic cells that express CXCR6 are $CD4^+$ T cells. In embodiments, the hepatic cells that express CXCR6 are $CD8^+$ T cells. In embodiments, the hepatic cells that express CXCR6 are MAIT cells. In embodiments, the species is of the genus *Clostridium*. In embodiments, the species is *C. scindens*.

As FDA approval for HCC treatment with nivolumab, patients may be treated with 240 mg every 2 weeks or 480 mg every 4 weeks for HCC. Tadalafil may be administered at 10-20 mg per day for at least 10 days; however, the higher end of the range may negatively impact antitumor immunity. For vancomycin, 125 mg four times daily for 10 days has been used as initial standard dose for non-severe *Clostridium difficile* infection. It is contemplated that when using nivolumab, tadalafil, and vancomycin, the standard doses may be effective. In embodiments, the checkpoint inhibitor, e.g., nivolumab, is administered at 240 mg every 2 weeks or 480 mg every 4 weeks. In embodiments, the PDE5 inhibitor, e.g., tadalafil, is administered at 10-20 mg per day for at least 10 days, e.g., 10 mg PO (by mouth) daily. In embodiments, the vancomycin is administered at 125 mg four times daily for 10 days, e.g., 125 mg every 6 hours PO daily.

In embodiments, the primary bile acid is administered at a dose of from about 100 mg/kg to about 700 mg/kg (mg of primary bile acid to kg body weight of human). In embodiments, the dose is about 100 mg/kg, about 200 mg/kg, about 300 mg/kg, about 400 mg/kg, about 500 mg/kg, about 600 mg/kg, or about 700 mg/kg. In embodiments, the dose is about 400 mg/kg. In embodiments, the dose is from about 100 mg/kg to about 200 mg/kg, from about 100 mg/kg to about 300 mg/kg, from about 100 mg/kg to about 400 mg/kg, from about 100 mg/kg to about 500 mg/kg, from about 100 mg/kg to about 600 mg/kg, from about 100 mg/kg to about 700 mg/kg, from about 200 mg/kg to about 300 mg/kg, from about 200 mg/kg to about 400 mg/kg, from about 200 mg/kg to about 500 mg/kg, from about 200 mg/kg to about 600 mg/kg, from about 200 mg/kg to about 700 mg/kg, from about 300 mg/kg to about 400 mg/kg, from about 300 mg/kg to about 500 mg/kg, from about 300 mg/kg to about 600 mg/kg, from about 300 mg/kg to about 700 mg/kg, from about 400 mg/kg to about 500 mg/kg, from about 400 mg/kg to about 600 mg/kg, from about 400 mg/kg to about 700 mg/kg, from about 500 mg/kg to about 600 mg/kg, from about 500 mg/kg to about 700 mg/kg, or from about 600 mg/kg to about 700 mg/kg.

Without wishing to be bound by any theory, it is believed that depleting commensal bacteria, e.g., with the use of antibiotics, alters bile acids, preserving primary bile acids that induce CXCL16 expression, and reducing secondary bile acids that inhibit CXCL16 expression, causing CXCL16 upregulation in liver sinusoidal endothelial cells (LSEC), followed by accumulation in the liver of, e.g., NKT cells, which express CXCR6 (Mouse CXCR6 Gene ID: 80901, Human CXCR6 Gene ID: 10663) that recognize CXCL16 as its ligand. These NKT cells are more active and produce more IFNγ when they encounter antigen loaded tumor cells compared to normal NKT cells, indicating stronger anti-tumor function. In mouse liver, NKT, $CD4^+$ T and $CD8^+$ T cells together comprise ~85% of the $CXCR6^+$ population. The rest are 7% double negative T cells and ~8% $CD3^-$ leukocytes.

An "effective amount" or "an amount effective to treat" refers to a dose that is adequate to prevent or treat an adverse condition in the liver in a mammal. Amounts effective for a therapeutic or prophylactic use will depend on, for example, the stage and severity of the condition being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various conditions could require prolonged administration involving multiple administrations, perhaps in each or various rounds of administration.

For purposes of the invention, the amount or dose should be sufficient to effect a therapeutic or prophylactic response in the mammal over a reasonable time frame. For example, the dose should be sufficient to treat or prevent a condition in a period of from about 2 hours or longer, e.g., about 12 to about 24 or more hours, from the time of administration. In certain embodiments, the time period could be even longer.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of an adverse condition of the liver in a mammal. Furthermore, the treatment or prevention provided by the inventive method can include treatment or prevention of one or more conditions or symptoms being treated or prevented. Also, for purposes herein, "prevention" can encompass delaying the onset of the condition, or a symptom thereof.

The following includes certain aspects of the invention.

1. A set comprising vancomycin and a checkpoint inhibitor for use in treating or preventing an adverse condition of the liver of a mammal.

2. The set according to the use of aspect 1, wherein the checkpoint inhibitor is to be administered simultaneously with the administration of the vancomycin.

3. The set according to the use of aspect 1, wherein the checkpoint inhibitor is to be administered sequentially with the administration of the vancomycin.

4. The set according to the use of any one of aspects 1-3, wherein the checkpoint inhibitor is a programmed death 1 (PD-1) inhibitor.

5. The set according to the use of aspect 4, wherein the PD-1 inhibitor is nivolumab.

6. The set according to the use of any one of aspects 1-5, wherein the set further comprises a phosphodiesterase type 5 (PDE5) inhibitor.

7. The set according to the use of aspect 6, wherein the PDE5 inhibitor is to be administered simultaneously with the administration of the vancomycin or checkpoint inhibitor.

8. The set according to the use of aspect 6, wherein the PDE5 inhibitor is to be administered sequentially with the administration of the vancomycin or checkpoint inhibitor.

9. The set according to the use of any one of aspects 6-8, wherein the PDE5 inhibitor is tadalafil.

10. The set according to the use of any one of aspects 1-9, wherein the set further comprises a primary bile acid 11. The set according to the use of aspect 10, wherein the primary bile acid is taurocholic acid (TCA), β-muricholic acid (β-MCA), tauro-β-muricholic acid (T-β-MCA), or chenodeoxycholic acid (CDCA).

12. The set according to the use of any one of aspects 1-11, wherein the adverse condition is tumor growth, tumor metastasis, or autoimmune disease.

13. The set according to the use of aspect 12, wherein the adverse condition is autoimmune disease.

14. The set according to the use of aspect 13, wherein the autoimmune disease is Type 1 diabetes, allergic encephalomyelitis, arthritis, systemic lupus erythematosus, inflammatory colitis, or Graves's thyroiditis.

15. The set according to the use of any one of aspects 1-11, wherein the adverse condition is liver metastasis or hepatocellular carcinoma (HCC).

16. The set according to the use of any one of aspects 1-11, wherein the adverse condition is colorectal, lung, breast, pancreatic, stomach, melanoma, or neuroendocrine cancer.

17. The set according to the use of any one of aspects 1-16, wherein the use is for treating the adverse condition.

18. The set according to the use of any one of aspects 1-16, wherein the use is for preventing the adverse condition.

19. The set according to the use of any one of aspects 1-18, wherein the mammal is a human.

20. A composition comprising vancomycin and a checkpoint inhibitor for use in treating or preventing an adverse condition of the liver of a mammal.

21. The composition according to the use of aspect 20, wherein the checkpoint inhibitor is a programmed death 1 (PD-1) inhibitor.

22. The composition according to the use of aspect 21, wherein the PD-1 inhibitor is nivolumab.

23. The composition according to the use of any one of aspects 20-22, wherein the composition further comprises a phosphodiesterase type 5 (PDE5) inhibitor.

24. The composition according to the use of aspect 23, wherein the PDE5 inhibitor is tadalafil.

25. The composition according to the use of any one of aspects 20-24, wherein the composition further comprises a primary bile acid.

26. The composition according to the use of aspect 25, wherein the primary bile acid is taurocholic acid (TCA), β-muricholic acid (β-MCA), tauro-β-muricholic acid (T-β-MCA), or chenodeoxycholic acid (CDCA).

27. The composition according to the use of any one of aspects 20-26, wherein the adverse condition is tumor growth, tumor metastasis, or autoimmune disease.

28. The composition according to the use of aspect 27, wherein the adverse condition is autoimmune disease.

29. The composition according to the use of aspect 28, wherein the autoimmune disease is Type 1 diabetes, allergic encephalomyelitis, arthritis, systemic lupus erythematosus, inflammatory colitis, or Graves's thyroiditis.

30. The composition according to the use of any one of aspects 20-26, wherein the adverse condition is liver metastasis or hepatocellular carcinoma (HCC).

31. The composition according to the use of any one of aspects 20-26, wherein the adverse condition is colorectal, lung, breast, pancreatic, stomach, melanoma, or neuroendocrine cancer.

32. The composition according to the use of any one of aspects 20-31, wherein the use is for treating the adverse condition.

33. The composition according to the use of any one of aspects 20-31, wherein the use is for preventing the adverse condition.

34. The composition according to the use of any one of aspects 20-33, wherein the mammal is a human.

35. A primary bile acid for use in treating or preventing an adverse condition of the liver of a mammal.

36. The primary bile acid according to the use of aspect 35, wherein the primary bile acid is formulated for direct absorption by the intestine, formulated for protection from intestinal enzymes, or both.

37. The primary bile acid according to the use of aspect 35 or 36, wherein the primary bile acid is administered in combination with a substance that inhibits immunosuppression, a substance that elicits an immune response, or both.

38. A method of treating or preventing an adverse condition of the liver of a mammal, the method comprising administering to the mammal an effective amount of a primary bile acid.

39. The method of aspect 38, wherein the primary bile acid is formulated for direct absorption by the intestine, formulated for protection from intestinal enzymes, or both.

40. The method of aspect 38 or 39, wherein the primary bile acid is administered at a dose from about 100 mg/kg to about 700 mg/kg.

41. The method of aspect 40, wherein the dose is about 400 mg/kg.

42. The method of any one of aspects 38-41, wherein the primary bile acid is administered in combination with a substance that inhibits immunosuppression, a substance that elicits an immune response, or both.

43. The method of aspect 42, wherein the substance is anti TGF-beta or anti IL-10.

44. The method of aspect 42, wherein the substance is a checkpoint inhibitor.

45. The method of aspect 44, wherein the checkpoint inhibitor is pembrolizumab, nivolumab, atezolizumab, avelumab, durvalumab, or ipilimumab.

46. The method of aspect 44, wherein the checkpoint inhibitor is an indoleamine (2,3)-dioxygenase (IDO) inhibitor.

47. The method of aspect 46, wherein the inhibitor is epacadostat, indoximod, BMS-986205, NLG802, or HTI-1090.

48. The method of aspect 42, wherein the substance is a tumor vaccine.

49. The method of aspect 48, wherein the vaccine is an AFP peptide, a DC pulsed AFP peptide, or an NY-ESO-1 peptide.

50. The method of aspect 42, wherein the substance is a chemotherapeutic compound.

51. The method of aspect 50, wherein the chemotherapeutic compound is abraxane, amsacrine, azacitidine, bendamustine, bleomycin, busulfan, cabazitaxel, capecitabine, carboplatin, carmustine, chlorambucil, cisplatin, 5fu, cladribine, clofarabine, crisantaspase, cyclophosphamide, cytarabine, dacarbazine, dactinomycin, daunorubicin, docetaxel, doxorubicin, epirubicin, eribulin, etoposide, flag-ida, fludarabine, fluorouracil, gemcitabine, hydroxycarbamide, idarubicin, ifosfamide, irinotecan, leucovorin, liposomal daunorubicin, liposomal doxorubicin, melphalan, mercaptopurine, mesna, methotrexate, mitomycin, mitotane, mitoxantrone, oxaliplatin, paclitaxel, pemetrexed, pentostatin, pertuzumab, procarbazine, raltitrexed, rasburicase, streptozocin, temozolomide, thiotepa, tioguanine, topotecan, trabectedin, treosulfan, trifluridine-tipiracil hydrochloride, vinblastine, vincristine, vindesine, or vinorelbine.

52. The method of any one of aspects 38-51, wherein the primary bile acid is formulated for protection from intestinal enzymes.

53. The method of aspect 52, wherein the protection prevents or reduces dehydroxylation by a dehydroxylase.

54. The method of aspect 53, wherein the formulation comprises lactulose, wheat bran, NAD+, or NADH.

55. The method of any one of aspects 38-54, wherein the adverse condition is tumor growth, tumor metastasis, or autoimmune disease.

56. The method of aspect 55, wherein the adverse condition is autoimmune disease.

57. The method of aspect 56, wherein the autoimmune disease is Type 1 diabetes, allergic encephalomyelitis, arthritis, systemic lupus erythematosus, inflammatory colitis, or Graves's thyroiditis.

58. The method of aspect 55, wherein the adverse condition is liver metastasis or hepatocellular carcinoma.

59. The method of aspect 55, wherein the adverse condition is colorectal, lung, breast, pancreatic, stomach, melanoma, or neuroendocrine cancer.

60. The method of any one of aspects 38-59, wherein the method is a method of treating the adverse condition.

61. The method of any one of aspects 38-59, wherein the method is a method of preventing the adverse condition.

62. The method of any one of aspects 38-61, wherein the primary bile acid is taurocholic acid (TCA), β-muricholic acid (β-MCA), tauro-β-muricholic acid (T-β-MCA), or chenodeoxycholic acid (CDCA).

63. The method of any one of aspects 38-62, wherein the administration is intravenous.

64. The method of any one of aspects 38-63, wherein the administration is via the portal vein.

65. The method of any one of aspects 38-64, wherein the administration of the primary bile acid reduces the presence of a species of the gut microbiome, wherein the species inhibits expansion of hepatic cells that express CXCR6.

66. The method of aspect 65, wherein the hepatic cells that express CXCR6 are hepatic NKT cells.

67. The method of aspect 65, wherein the hepatic cells that express CXCR6 are CD4+ T cells.

68. The method of aspect 65, wherein the hepatic cells that express CXCR6 are CD8+ T cells.

69. The method of aspect 65, wherein the hepatic cells that express CXCR6 are MAIT cells.

70. The method of any one of aspects 65-69, wherein the species is of the genus *Clostridium*.

71. The method of aspect 70, wherein the species is *C. scindens*.

It shall be noted that the preceding are merely examples of embodiments. Other exemplary embodiments are apparent from the entirety of the description herein. It will also be understood by one of ordinary skill in the art that each of these embodiments may be used in various combinations with the other embodiments provided herein.

A previous study (Vrieze et al., J. Hepatol., 2014, 60: 824-831, incorporated herein by reference) on individuals (obese individuals considered healthy in terms of not having cancer) treated with oral vancomycin showed decreased fecal secondary bile acids with a simultaneous postprandial increase in primary bile acids in plasma (Reference is made to FIGS. 3A-D of Vrieze et al., which are incorporated herein by reference along with portions of Vrieze et al. discussing the figures and the data they present). This finding indicates there are certain similarities between human and mice regarding the metabolic change of bile acid to oral vancomycin. Feeding secondary bile acids or colonization of bile acid-metabolizing bacteria reversed both NKT cell accumulation and inhibition of liver tumor growth in mice with altered gut commensal bacteria. The use in humans of vancomycin, and optionally a primary bile acid, is contemplated in addition to the use of a checkpoint inhibitor.

Another previous study (Hassel et al., Oncoimmunology, 6:9, e1326440, incorporated herein by reference) shows a representative image at FIG. 1 (which is incorporated herein by reference along with portions of Hassel et al. discussing the figure and the data it presents) of PET-CT scans from a metastatic melanoma patient. The scans show stable disease under tadalafil. Califano et al. (Clin. Cancer Res., 21:30-38 (2015), incorporated by reference) finds that tadalafil augments tumor specific immunity in patients with HNSCC. The use in humans of a PDE5 inhibitor, e.g., tadalafil, is contemplated in addition to the use of vancomycin and a checkpoint inhibitor.

The following examples further illustrate the invention but, of course, should not be construed as in any way limiting its scope.

Example 1

This example demonstrates alteration of the gut microbiome, in accordance with embodiments of the invention.

Murine Studies

SPF C57BL/6 and BALB/c mice were purchased from Charles River Laboratories (Wilmington, Mass., USA). CXCR6 knockout mice were purchased from Jackson Laboratory (Bar Harbor, Me., USA). CD1d knockout mice, LAP-tTA, and TRE-MYC mice have been previously described (Ma et al., Nature, 531: 253-257 (2016), incorporated by reference herein). Germ-free mice were provided by Dr. Romina Goldszmid (cancer and inflammation program, NIH, Bethesda, Md., USA). Newly purchased four-week old C57BL/6 or BALB/c mice were randomized into 5 mice/cage and housed for one week to normalize gut microbiome.

Then mice were assigned into $H_2O$ or ABX administration groups. Mice in the ABX group received a three-antibiotic cocktail in the drinking water containing vancomycin (Hospira, Lake Forest, Ill., USA, 0.5 g/L), neomycin (VETone, Boise, Id., USA, 0.5 g/L) and primaxin (Merck & Co., Kenilworth, N.J., USA, 0.5 g/L) as previously reported (Iida et al., Science, 342: 967-970 (2013), incorporated by reference herein). In some experiments mice were given single antibiotic water, and cefoperazone (MP Biomedicals, Santa Ana, Calif., USA) was given at the concentration of 0.5 g/L. Fresh antibiotic water was replaced every other day.

After 3 weeks of ABX administration, mice were challenged with different tumor cell lines. B16-F1 and A20 cells were purchased from ATCC (Manassas, Va., USA). EL4 cells were used as described (Ma et al., J. Leukoc. Biol., 92: 1199-1206 (2012), incorporated by reference herein). $1\times10^6$ EL4 tumor cells were given by subcutaneous (s.c.) or tail vein injection, $3\times10^5$ B16-F1 tumor cells were given by intrasplenic injection as described before (Eggert et al., Cancer Cell, 30: 533-547 (2016), incorporated by reference herein), and $1\times10^6$ A20 tumor cells were given by tail vein injection.

In some experiments mice were fed with a 2% cholestyramine diet made by Research Diets Inc. (New Brunswick, N.J., USA). Mice were administered 500 µg anti-CD4 (clone GK1.5, BioxCell, West Lebanon, N.H., USA) or 200 µg anti-CD8 (clone 2.43, BioxCell) 24 hrs before receiving tumor injection for depletion studies.

For in vivo NKT cell stimulation, $1\times10^6$ αGalCer-loaded A20 tumor cells in the combination of brefeldin A (500 µg/mouse) were given by tail vein injection, and mice were sacrificed 3 hrs after injection. αGalCer-loading was performed by incubate A20 cells with 1 µg/ml αGalCer overnight followed by three times of washing.

At the experimental end points, mice were sacrificed for organ harvest. All experiments were conducted according to local institutional guidelines and approved by the Animal Care and Use Committee of the National Institutes of Health, Bethesda, USA.

Flow Cytometry

Cells were surface-labelled with the indicated antibodies for 15 min at 4° C. Intracellular staining using a Foxp3/transcription factor staining buffer set (eBioscience, now part of ThermoFisher Scientific, Waltham, Mass., USA) was used according the manufacturer's instructions. Flow cytometry was performed on a BD LSRFortessa platform (BD Biosciences, San Jose, Calif., USA) and results were analyzed using FlowJo software version 9.3.1.2 (TreeStar, Ashland, Oreg., USA). Dead cells were excluded by using live/dead fixable near-IR dead cell staining kit (ThermoFisher Scientific).

The following antibodies were used for flow cytometry analysis: anti-TCRβ-BV510 (clone H57-587, Biolegend, San Diego, Calif., USA), PBS57/CD1d-tetramer-APC (NIH core facility, Bethesda, Md., USA), anti-CXCR6-FITC (clone SA051D1, Biolegend), anti-CD3-PE (clone 17A2, Biolegend), anti-CD4-PE (clone RM4-5, Biolegend), anti-CD4-Alexa Fluor 700 (clone GK1.5, Biolegend), anti-CD8-BV210 (clone 53-61 Biolegend), anti-CD19-PerCP/Cy5.5 (clone eBiolD3, eBioscience), anti-CD49b (clone DX5, eBioscience), anti-TCRγ/δ-PE, (clone GL3, BD pharmingen, BD Biosciences), anti-CD11b-BV421 (clone M1/70, Biolegend), anti-Ly6G-Alexa Fluor 700 (clone 1A8, Biolegend), anti-Ly6C-APC (clone HK1.4, Biolegend), anti-CD44-PE/Cy7 (clone IM7, eBioscience), anti-CD62L-PerCP/Cy5.5 (MEL-14, Biolegend), anti-CD69-Pacific blue (clone H1.2F3, Biolegend), anti-CD25-FITC (clone 7D4, BD pharmingen), anti-4-1BB-PE (clone 17B5, Biolegend), anti-Foxp3-Alexa Fluor 488 (clone 22F6, Biolegend), anti-Tbet-Pacific Blue (clone 4B10, Biolegend), anti-RORγ-PE (clone B2D, eBioscience), anti-PLZF-PerCP/Cy5.5 (clone 9E12, Biolegend), anti-CD1d-PE (clone 1B1, eBioscience), anti-IFNγ-PE (clone XMG1.2, BD Biosciences), and anti-TNFα-PerCP/Cy5.5 (clone MP6-XT22, Biolegend).

The following markers were used for identifying different immune cell subsets: TCRβ$^+$CD1d-Teteramer$^+$ for NKT cells, CD3$^+$CD4$^{hi}$ for hepatic CD4$^+$ T cells, CD3$^+$CD8$^+$ for CD8$^+$ T cells, CD3$^-$CD19$^+$ for B cells, CD3$^-$CD49b$^+$ for NK cells, CD3$^+$TCRγ/δ$^+$ for γ/δ T cells, CD11b$^+$Ly6G$^+$Ly6C$^{lo}$ for G-MDSC. Absolute numbers were calculated by multiplying frequencies obtained from flow cytometry by the total live mononuclear cell count, and then divided by liver weight.

In Vivo Cytotoxicity Assay

Splenocytes isolated from naïve C57BL/6 mice were loaded with α-galactosylceramide (1 µg/ml) then labelled with high dose of CFSE as target cells. Unloaded cells were labelled with low dose of CFSE as control cells. Then CFSE$^{hi}$ target cell and CFSE$^{lo}$ controls cells were mixed at about 1:1 ratio. 10$^7$ mixed cells were injected i.v. into ABX or H2O-administered C57BL/6 mice. Sixteen hours later, mice were killed and cytotoxicity was analyzed by flow cytometry. r=(% CFSE$^{lo}$/% CFSE$^{hi}$); $r_o$ is the ratio of mixed cells without injection; % cytotoxicity=[1−($r_0$/r)]×100.

Immunohistochemistry and Quantification

Immunohistochemistry was performed on 3 µm sections obtained from formalin-fixed paraffin-embedded liver tissues of H$_2$O (n=5) or ABX (n=5) administered mice using the Opal™ 5-color IHC Kit (PerkinElmer, Waltham, Mass., USA) according to the manufacturer's instructions.

The following primary antibodies were used: anti-CXCL16 (Bions Antibodies, Woburn, Mass., USA; bs-1441R, rabbit polyclonal, 1/4.000, Opal 620), anti-LYVE1 (Abcam, Cambridge, UK; rabbit polyclonal, 1/15.000, Opal 520). Slides were evaluated using the Vectra® 3 automated, high-throughput quantitative pathology imaging system (PerkinElmer, Waltham, Mass., USA) and the inForm® software (PerkinElmer) for segmentation and quantification of CXCL16$^+$/LYVE1$^+$ cells.

Hepatic Bile Acid Profiling

Fresh mice liver tissue was snap frozen in liquid nitrogen and then kept at −80° C. Hepatic bile acid composition was measured at West Coast Metabolomics Center at UC Davis (Davis, Calif., USA) using the targeted metabolite analysis service.

Liver Sinusoidal Endothelia Cell Preparation and Bile Acids Administration

Primary mice liver sinusoidal endothelia cells were isolated as previously described (Limmer et al., Nat. Med., 6: 1348-1354 (2000), incorporated by reference herein). Briefly, mice were CO$_2$ euthanized, and then the portal vein was cannulated, and the liver was perfused with 0.05% collagenase in Ca$^{2+}$ deprived medium. Liver cells were dissociated, and parenchymal cells were killed by incubation in 0.04% collagenase in Gey's balanced salt solution at 37° C. for 15 minutes. Then density gradient centrifugation was performed using Nycodenz solution at the final solution of 1.089 g/cm$^3$. Liver sinusoidal endothelial cells (LSEC) were isolated using anti-LSEC microbeads (Miltenyi, Bergisch Gladbach, Germany) according to the manufacturer's instructions. LSECs or the human SK-HEP1 cell line (ATCC, HTB-52) were administered different bile acids for 24 hours. Gene expression was analyzed by real-time PCR. Taurocholic acid (TCA), chenodeoxycholic acid (CDCA), deoxycholic acid (DCA), and taurodeoxycholic acid (TDCA) were purchased from Sigma (now Millpore-Sigma, St. Louis, Mo., USA). Tauro-β-muricholic acid (T-β-MCA), ω-muricholic acid (ω-MCA), and tauro-ω-muricholic acid (T-ω-MCA) were purchased from Steraloids Inc. (Newport, R.I., USA).

In Vivo Bile Acids Feeding

Mice were kept on ABX cocktail and fresh ABX was replaced every other day. Mice were fed with bile acids by oral gavage 48, 24 and 16 hrs prior to sacrifice. For A20 tumor bearing mice, ω-MCA were given 3 times/week. ω-MCA and CDCA were dissolved in corn oil and given at the dose of 6 mg/15 g body weight.

Gut Colonization with *Clostridium scindens*

Mice were fed with vancomycin in drinking water (Hospira, 0.5 g/L) for one week. Fresh antibiotic water was replaced every other day. One week later vancomycin was stopped, and the mice were given oral gavage of 10$^9$ *C. scindens* or vehicle (anaerobic glycerol) every day for 5 days. *C. scindens* was purchased from ATCC (35704), and grown under anaerobic conditions. One day after gavage, the colonization of *C. scindens* were confirmed by real-time PCR using primers specific for *C. scindens*.

16S rRNA Sequencing and Analysis

Mouse stool DNA extraction and 16S V4 tregion amplification were performed on the liquid handling robots (epMotion 5075 and epMotion 5073, Eppendorf, Hamburg, Germany). The V4 region of the 16S rDNA gene (515F-806R) was sequenced, generating partially overlapping, paired-end reads on the Illumina MiSeq platform (Illumina, San Diego, Calif., USA). After quality control filtering, a total of 3,979,728 reads were processed with an average of 132,657 reads per sample. The demultiplexed FASTQ files containing the 16S rRNA gene sequences were filtered for chimeric sequences using the USEARCH (Edgar, Bioinformatics, 26: 2460-2461 (2010), incorporated by reference herein; version 8.1.1831) utility's UCHIME implementation and the 'gold' database (version microbiomeutil-r20110519). The reads were then binned into Operational Taxonomic Units (OTUs) at 97% similarity using USEARCH's cluster_otus command. The OTUs thus obtained were classified and aligned using QIIME (Caporaso et al., Nat. Methods, 7: 335-336 (2010), incorporated by reference herein; version 1.9.1) scripts. The assign_taxonomy.py script was used to assign taxonomy using the default RDP method (Wang et al., Appl. Environ. Microbiol., 73: 5261-5267 (2007), incorporated by reference herein) and the default GreenGenes database (DeSantis et al., Appl. Environ. Microbiol., 72: 5069-5072 (2006), incorporated by reference herein). This provided insight into the larger trends at higher taxonomic levels (such as order Clostridiales).

Human Studies

Non-tumor specimens derived from a set of 142 patients of the TIGER-LC Consortium were used in this study (Chaisaingmongkol et al., Cancer Cell, 32: 57-70 (2017), incorporated by reference herein). Transcript expression was measured using the Affymetrix Human Transcriptome Array 2.0 (Affymetrix, Santa Clara, Calif., USA). Data has been deposited into the Gene Expression Omnibus (GEO) public database at NCBI (GEO Series GSE76297). A total of 718 biochemical metabolite species were measured by Metabolon's Discover HD4 Platform. All expression and metabolite data were $\log_2$ transformed. Pearson correlation analysis was performed using GraphPad Prism 7 (GraphPad Software, La Jolla, Calif., USA) to determine correlation between CXCL16 gene expression and selected metabolites. Due to the missing information caused by detection limitations, 85 valid patient data were used to correlate CDCA and CXCL16 expression.

Statistical Analysis

The sample sizes for animal studies were guided by previous murine studies. Statistical analysis was performed with GraphPad Prism 6 (GraphPad Software). The significant differences between groups were calculated by Student's unpaired t-test, one-way, or two-way ANOVA (Tukey's and Bonferroni's multiple comparison test). Welch's corrections were used when variances between the groups were unequal. $P<0.05$ was considered as statistically significant.

Ma et al., Science, 360, eaan5931 (2018) is incorporated herein by reference in its entirety.

Altering Gut Microbiome Suppresses Liver Tumors

Figure 1B:
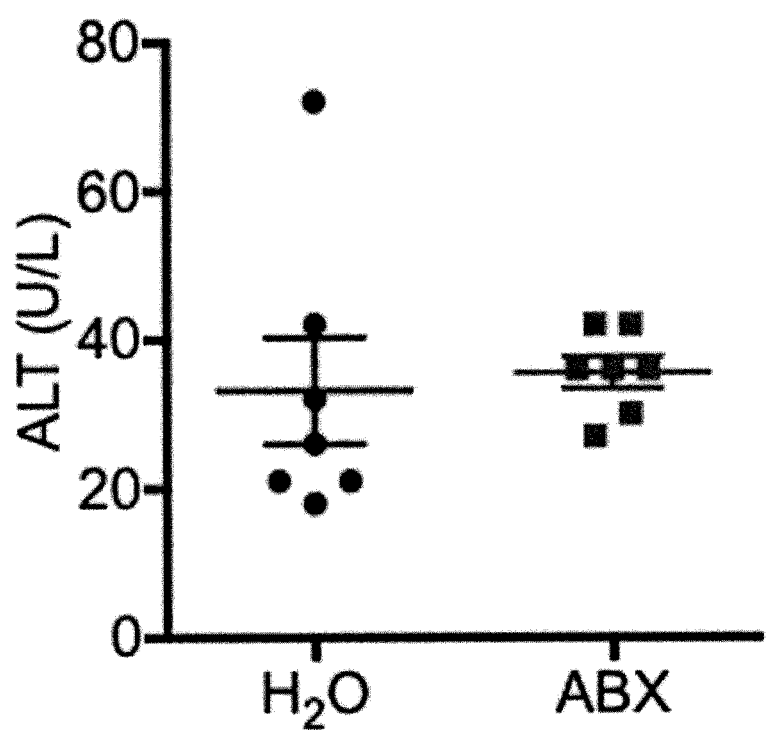
FIG. 1B is a dot plot showing serum alanine aminotransferase (ALT) levels in mice administered ABX or $H_2O$. n=7.
Figure 1C:
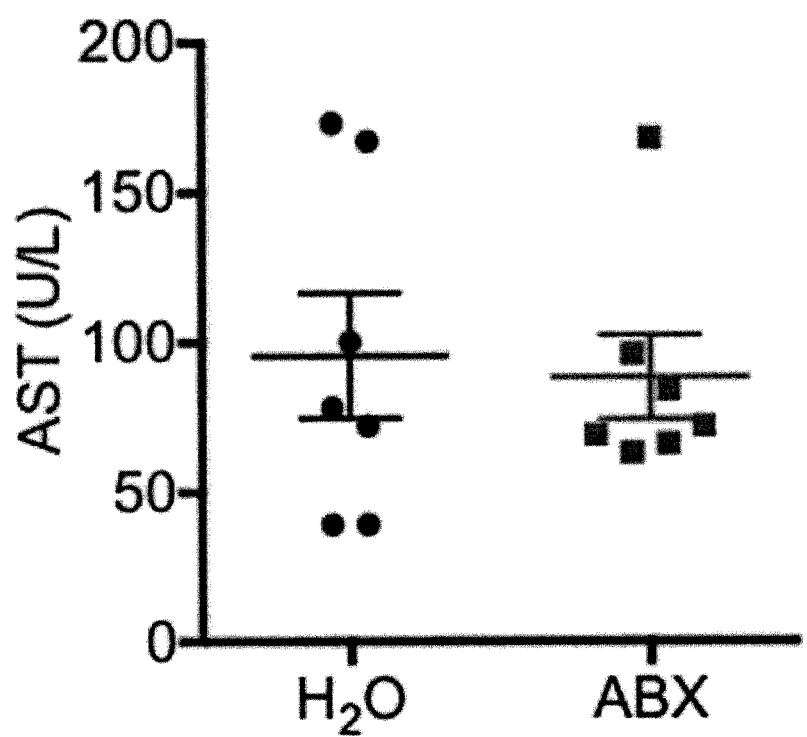
FIG. 1C is a dot plot showing serum aspartate aminotransferase (AST) levels in mice administered ABX or $H_2O$. n=7.
Figure 2A:
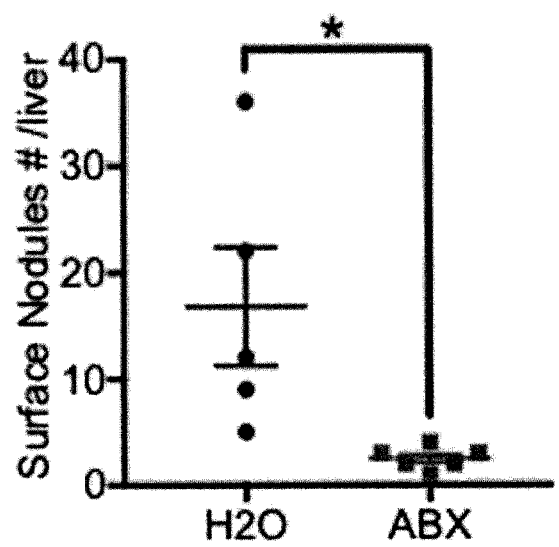
FIG. 2A is a dot plot showing liver surface tumor nodules counts, in accordance with embodiments of the invention. MYC transgene was turned on at the age of 4 weeks. MYC-ON mice were fed with ABX or regular water. Ten weeks later, mice were sacrificed and liver surface tumor nodules were counted. Representative liver image and quantitative results are shown. n=5 for $H_2O$, 6 for ABX, $p<0.05$, Student's t-test.
Figure 2B:
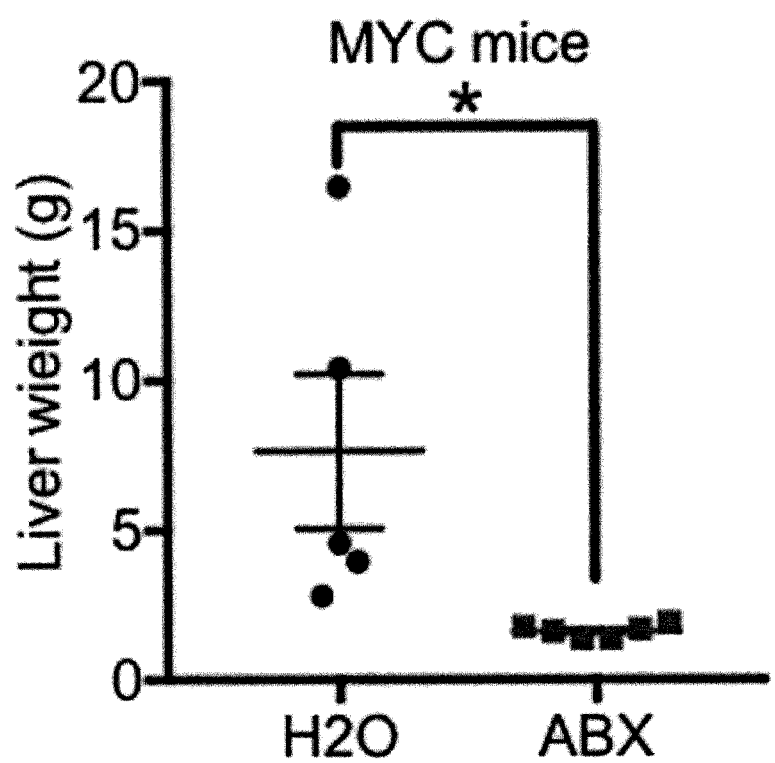
FIG. 2B is a dot plot showing liver weight of liver sections of the MYC-ON mice described in FIG. 2A, in accordance with embodiments of the invention. n=5 for $H_2O$, 6 for ABX. $p<0.05$, Student's t-test.

Spontaneous HCC was induced in MYC transgenic mice as described (Ma et al., Nature, 531: 253-257 (2016), incorporated by reference herein). An antibiotic cocktail (ABX) was added to drinking water to deplete gut commensal bacteria (Iida et al., Science, 342: 967-970 (2013), incorporated by reference herein). The antibacterial efficacy of ABX was confirmed, and the cocktail was not toxic to the liver (FIGS. 1A-1C). Consistent with previous findings, fewer and smaller HCC were found in ABX-administered MYC mice (FIGS. 2A and 2B).

Figure 3:
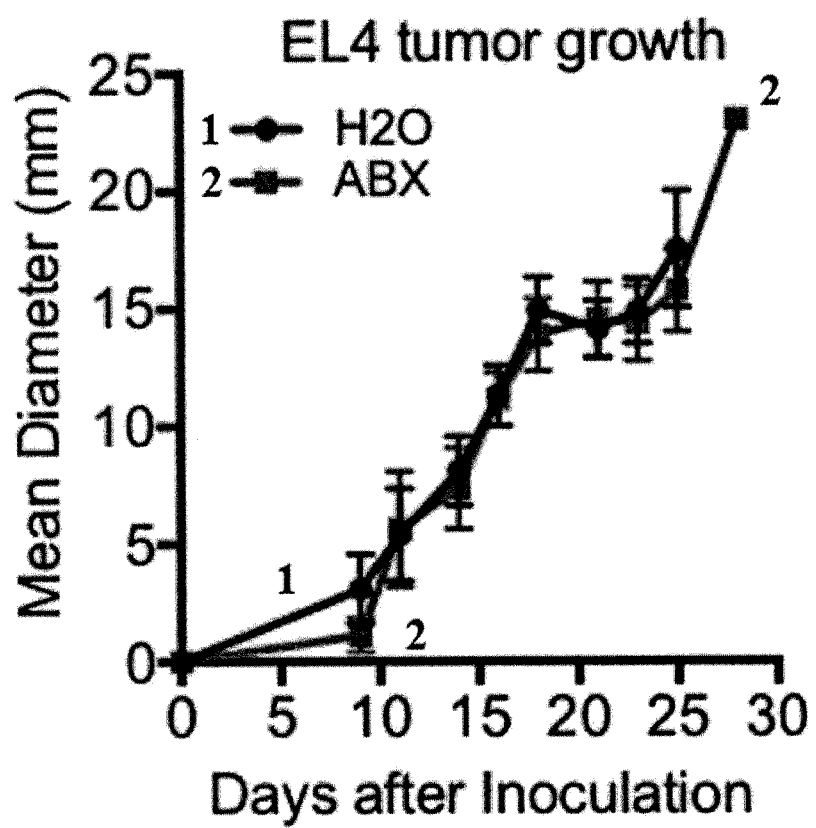
FIG. 3 is a line graph showing a growth curve of subcutaneous (s.c.) EL4 tumors in mice administered ABX or $H_2O$. n=5.
Figure 4:
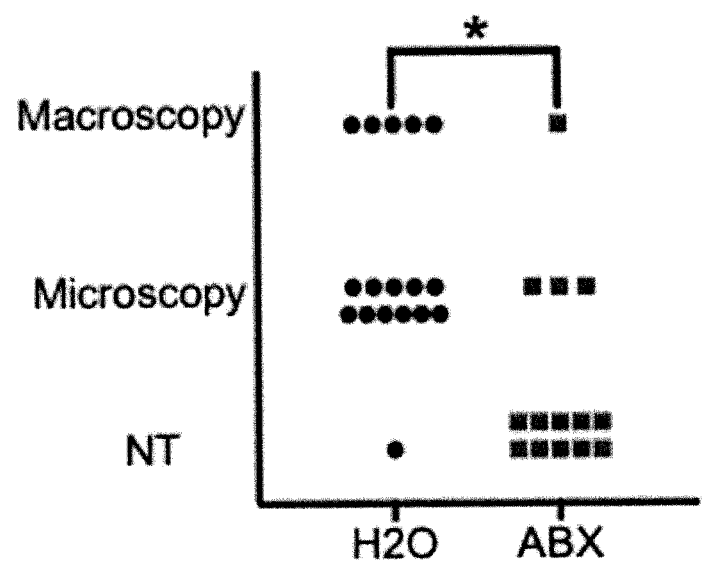
FIG. 4 is a dot plot showing tumor counts, in accordance with embodiments of the invention, of 5 week old C57BL/6 mice administered ABX or $H_2O$ for 3 weeks before receiving s.c. EL4 tumor cell injection, where 4 weeks later, liver metastases were determined. n=17 for $H_2O$, 12 for ABX. $p<0.05$, Chi-square test.
Figure 5:
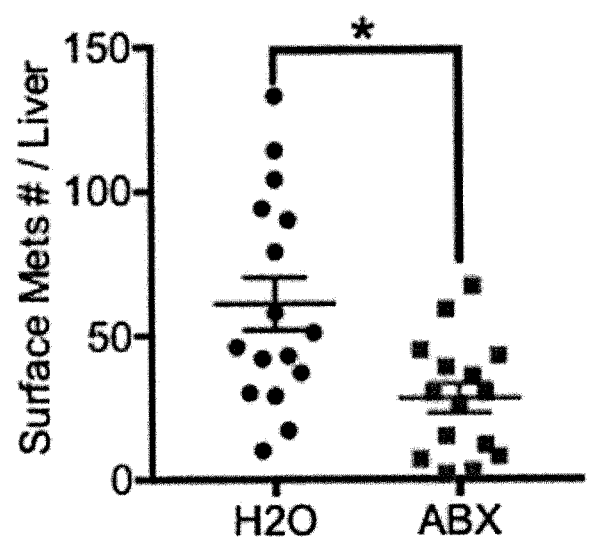
FIG. 5 is a dot plot showing surface cumulative liver tumor counts, in accordance with embodiments of the invention, of 5 week old C57BL/6 mice administered for 3 weeks with ABX or $H_2O$, then given intrasplenic B16 tumor cell injection. One and a half weeks after injection, liver metastases were measured. n=18 for $H_2O$, 15 for ABX. $p<0.05$, Student's t-test.

Next, the studies were extended to an s.c. implantation model (EL4 thymoma) to study potential systemic effects. ABX administration did not affect the growth of s.c. EL4 tumor in syngeneic C57BL/6 mice (FIG. 3). In contrast, fewer spontaneous liver metastasis were seen in mice with large s.c. EL-4 tumors upon ABX administration (FIG. 4). To confirm this liver-selective anti-tumor effect, an intrasplenic tumor injection model was used (Eggert et al., Cancer Cell, 30: 533-547 (2016), incorporated by reference herein). Similarly, a robust decrease of B16 liver metastasis was found (FIG. 5).

Figure 6:
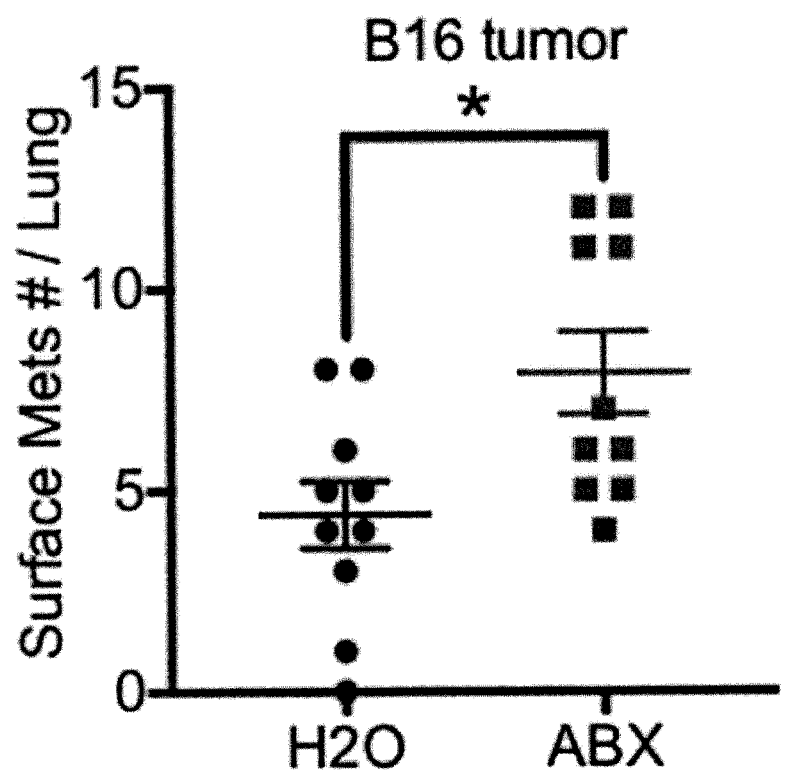
FIG. 6 is a dot plot showing surface lung tumor counts of ABX or $H_2O$ administered mice given tail vein injection of B16 tumor cells. Lung metastasis was measured. n=10, $p<0.05$, Student's t-test.
Figure 7A:
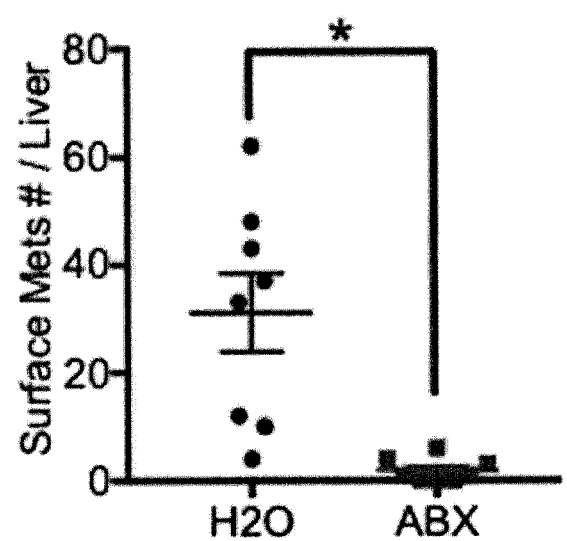
FIG. 7A is a dot plot showing liver metastases counted for 5 week old BALB/c mice administered ABX or $H_2O$ for 3 weeks, then injected with A20 tumor cell via tail vein injection. Liver metastases were counted three weeks after injection. Cumulative data are shown. n=8, $p<0.05$, Student's t-test.
Figure 7B:
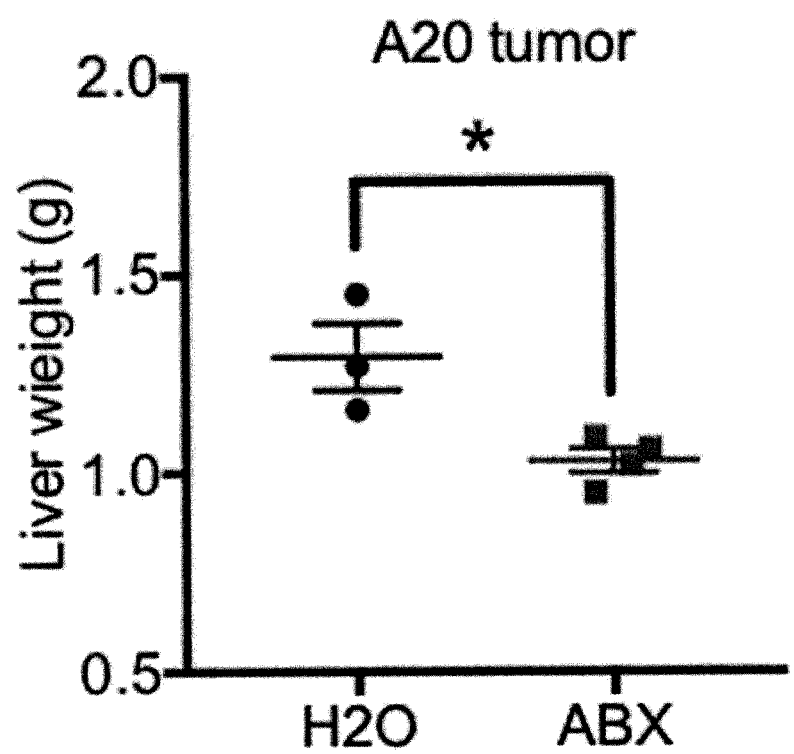
FIG. 7B is a dot plot showing liver weight of liver sections in mice that received tail vein injection of A20 tumor cells. n=4, $p<0.05$, Student's t-test.

Unlike in the liver, lung metastasis were increased by ABX when the same B16 tumor cells were injected via the tail vein (FIG. 6). Similar results were observed in BALB/c mice using A20 tumors (FIGS. 7A and 7B). Together, the results showed that changing gut commensal bacteria can modify growth kinetics of intrahepatic tumors.

Hepatic NKT Cell Accumulation Precedes the Tumor Inhibition

Figure 8A:
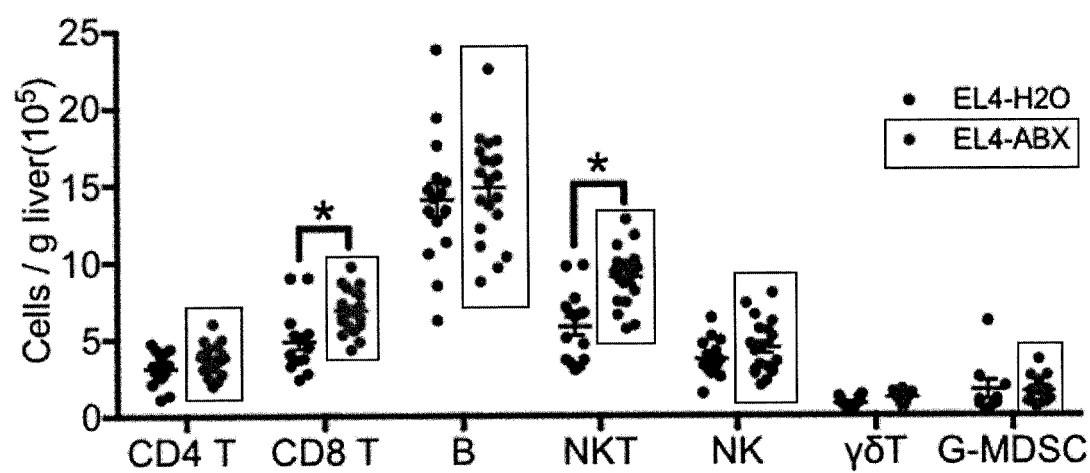
FIG. 8A is a dot plot showing cells/g liver of liver infiltrating immune cells, in accordance with embodiments of the invention, measured in ABX or $H_2O$ administered C57BL/6 mice, two and a half weeks after being given s.c. EL4 tumor injection. Cumulative data are shown. n=15 for EL4-$H_2O$, 20 for EL4-ABX. $p<0.05$, two-way ANOVA.
Figure 8B:
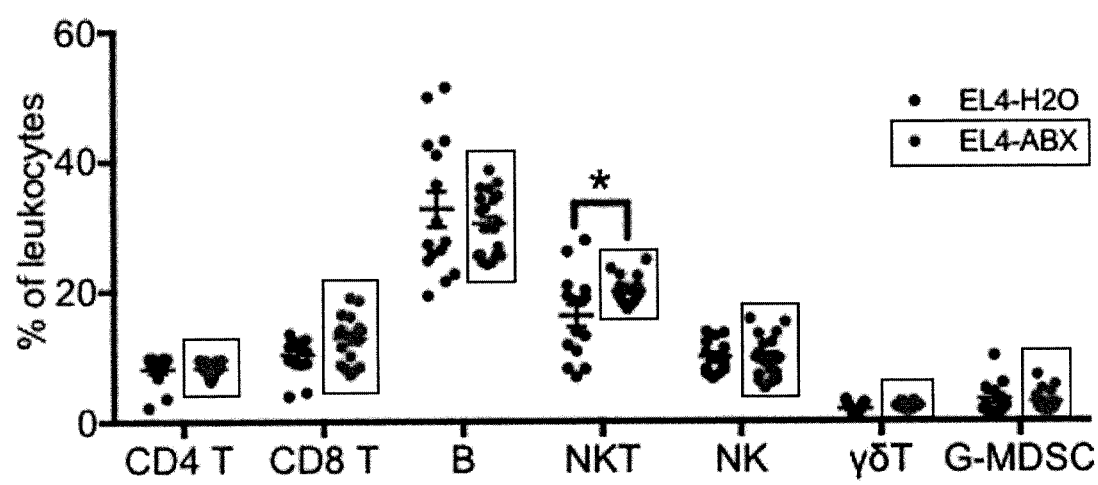
FIG. 8B is a dot plot showing frequencies of immune cell subsets in liver infiltrating mononuclear cells, in accordance with embodiments of the invention, from EL4-tumor bearing mice administered ABX or $H_2O$ described in FIG. 8A. n=15 for EL4-$H_2O$, 20 for EL4-ABX. $p<0.05$, two-way ANOVA.
Figure 9A:
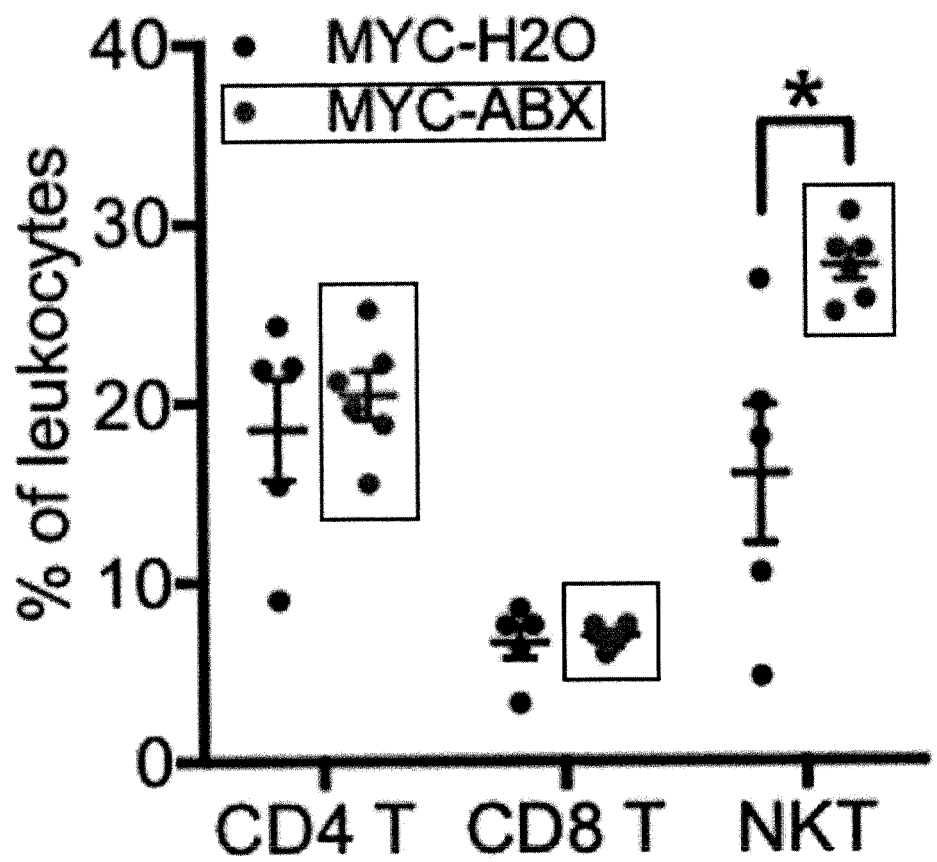
FIG. 9A is a dot plot showing hepatic natural killer T (NKT) cell, CD4 T cell, and CD8 T cell levels of MYC mice described in FIG. 2A, in accordance with embodiments of the invention. $p<0.05$, two-way ANOVA.
Figure 9B:
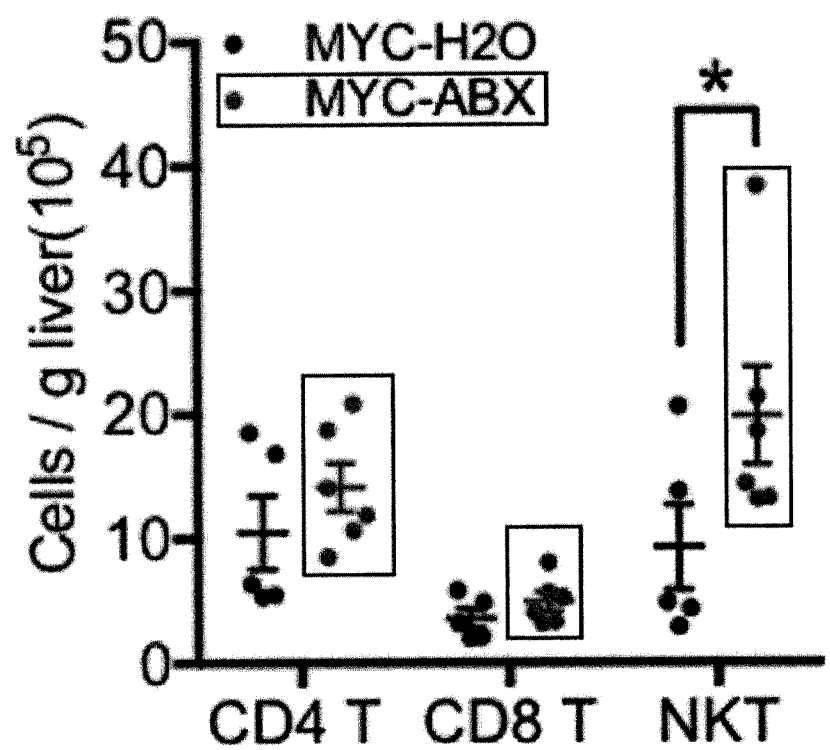
FIG. 9B is a dot plot showing absolute numbers of hepatic NKT, CD4 T and CD8 T cells in MYC mice described in FIG. 2A, in accordance with embodiments of the invention. n=5 for $H_2O$, 6 for ABX. $p<0.05$, two-way ANOVA.
Figure 10:
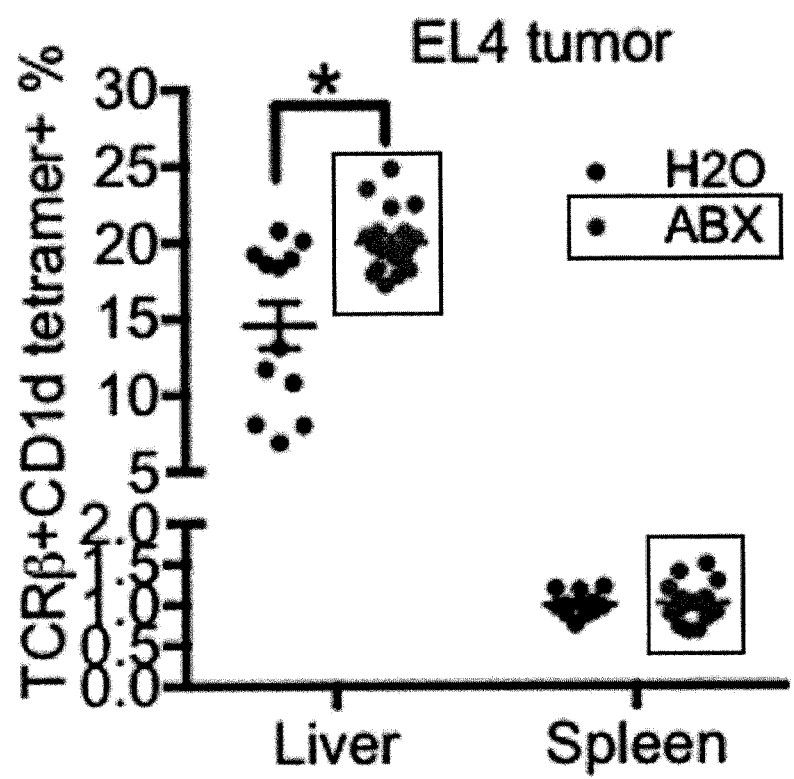
FIG. 10 is a dot plot showing frequencies of NKT cells in the liver and spleen of EL4 tumor-bearing mice administered ABX or $H_2O$. n=15 for EL4-$H_2O$, 20 for EL4-ABX. $p<0.05$, two-way ANOVA.
Figure 11A:
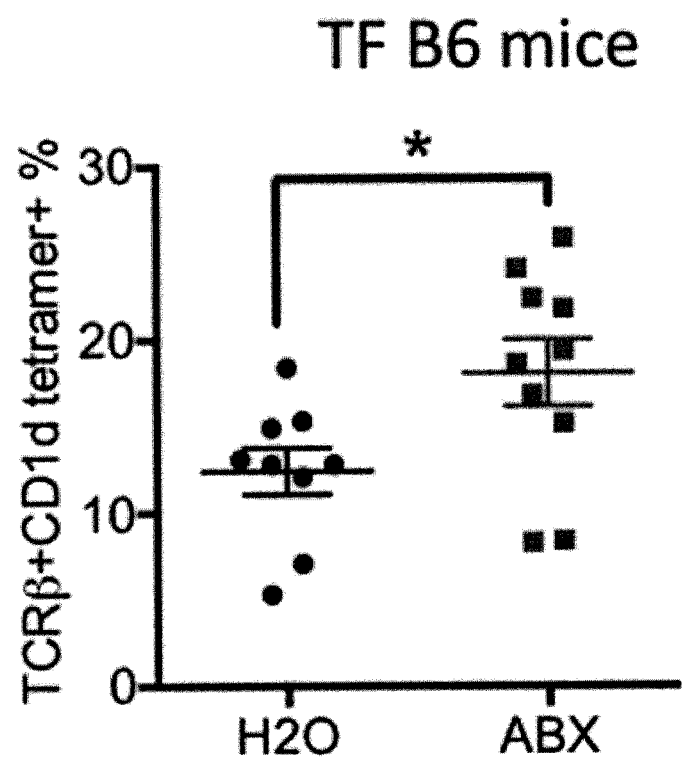
FIG. 11A is a dot plot showing percentage hepatic NKT cells in tumor-free C57BL/6 mice fed with ABX or $H_2O$, in accordance with embodiments of the invention. n=9 for $H_2O$, 10 for ABX. $p<0.05$, Student's t-test.
Figure 11B:
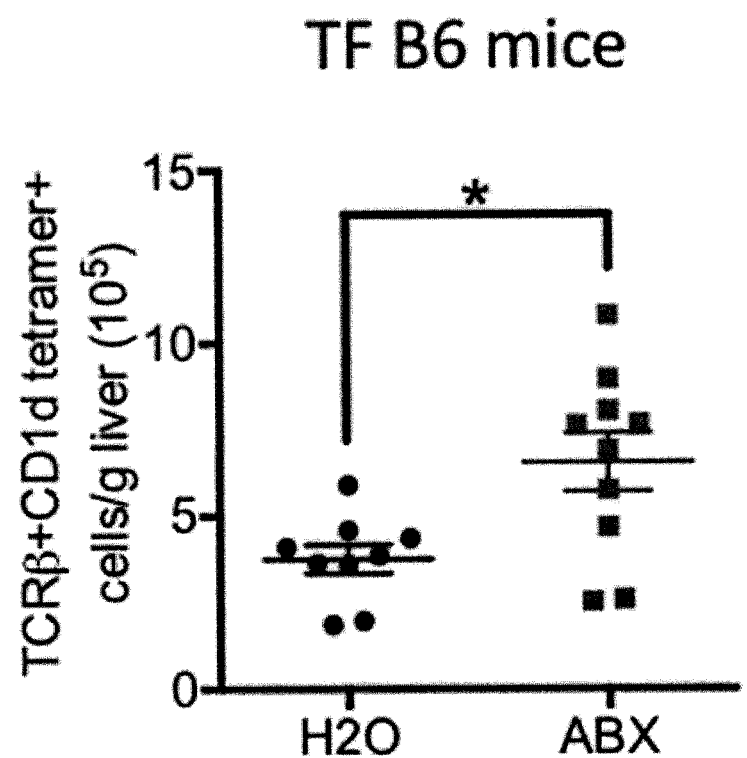
FIG. 11B is a dot plot showing cells/g liver hepatic NKT cells in tumor-free C57BL/6 mice fed with ABX or $H_2O$, in accordance with embodiments of the invention. n=9 for $H_2O$, 10 for ABX. $p<0.05$, Student's t-test.
Figure 11C:
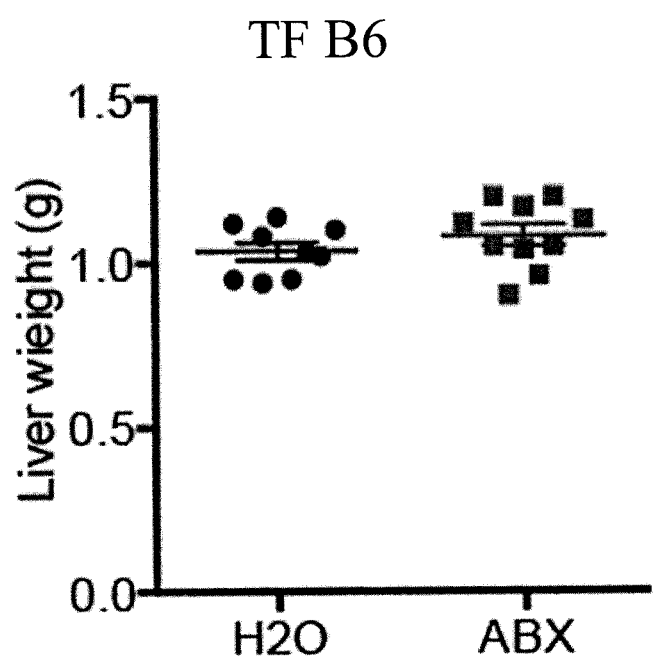
FIG. 11C is a dot plot showing liver weight of C57BL/6 mice administered ABX or H2O for 3 weeks. n=9 for H$_2$O, 10 for ABX, p<0.05, Student's t-test.
Figure 11D:
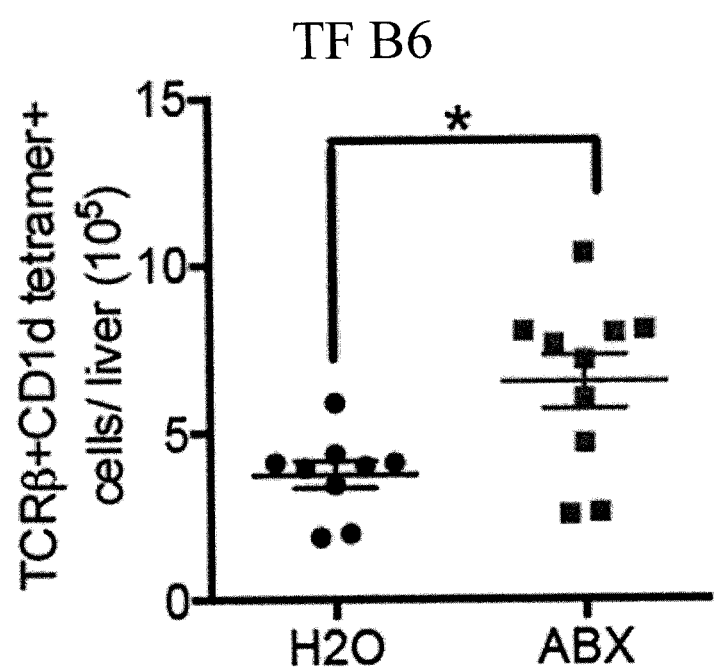
FIG. 11D is a dot plot showing hepatic NKT cell absolute number per liver of C57BL/6 mice administered ABX or H$_2$O for 3 weeks. n=9 for H2O, 10 for ABX, p<0.05, Student's t-test.

To explore the mechanism, the immune cell subsets in EL4-tumor bearing mice kept on ABX administration were studied. FIGS. 8A and 8B show that ABX administration caused a prominent expansion of hepatic NKT and CD8$^+$ T cells, while no changes were found in other immune cells (B cells, CD4$^+$ T, NK, $\gamma/\delta$ T cells and G-MDSC). The accumulation of hepatic NKT cells, but not CD8$^+$ T cells, was also observed in ABX-administered MYC mice bearing HCC (FIGS. 9A and 9B) suggesting a common phenomenon. Splenic NKT cell levels remained unchanged, suggesting a liver-specific effect (FIG. 10).

Figure 12A:
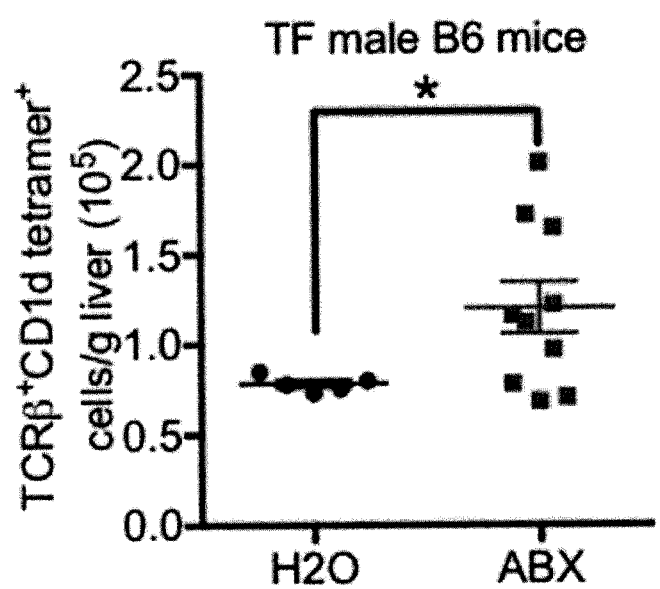
FIG. 12A is a dot plot showing cells/g liver hepatic NKT cells measured from male C57BL/6 mice fed with ABX or H$_2$O, in accordance with embodiments of the invention. n=5 for H$_2$O, 10 for ABX. p<0.05, Student's t-test.
Figure 12B:
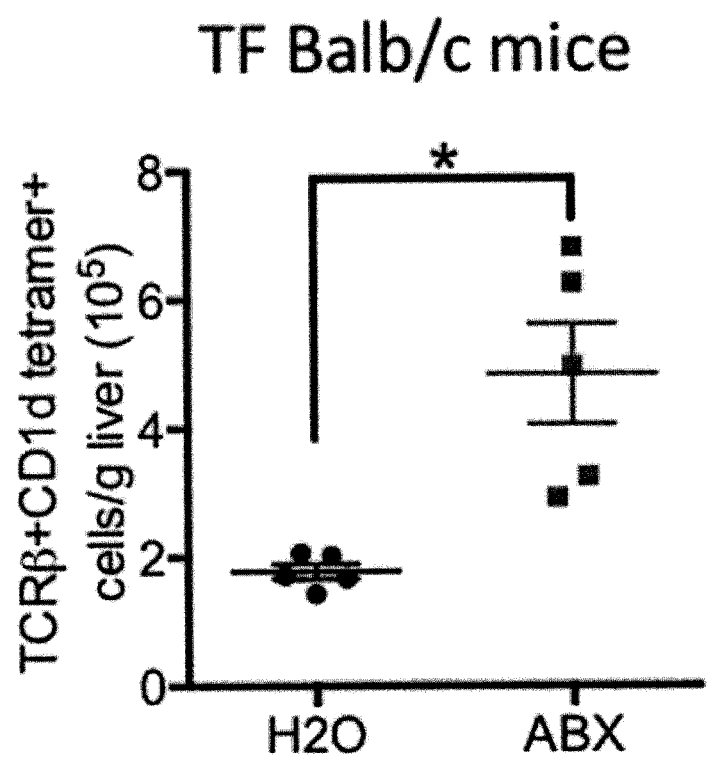
FIG. 12B is a dot plot showing cells/g liver of hepatic NKT cells in tumor-free BALB/c mice fed with ABX or H$_2$O, in accordance with embodiments of the invention. n=5, p<0.05, Student's t-test.
Figure 12C:
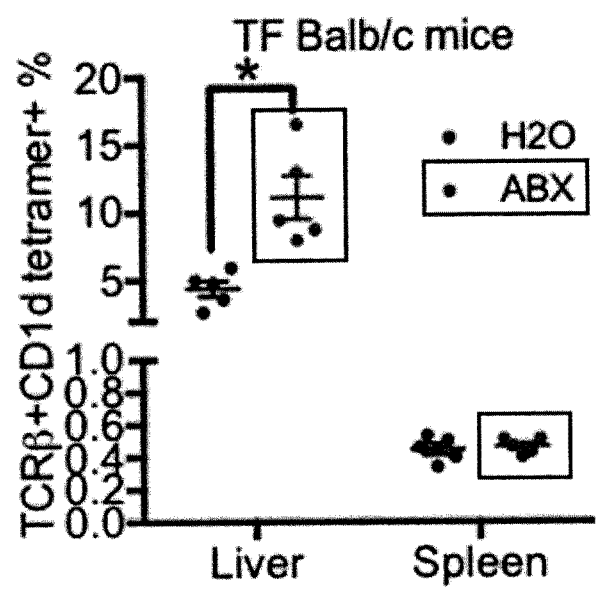
FIG. 12C is a dot plot showing frequencies of NKT cells in the liver and spleen of tumor-free BALB/c mice administered ABX or H$_2$O, in accordance with embodiments of the invention. n=5, p<0.05, two-way ANOVA.
Figure 12D:
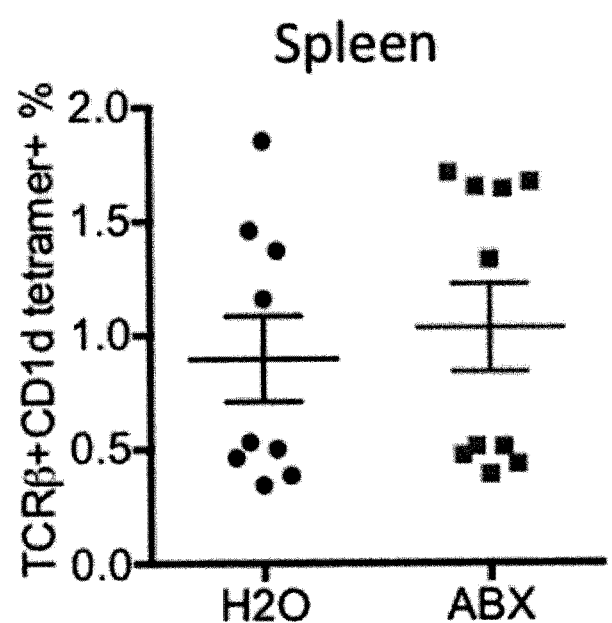
FIG. 12D is a dot plot showing frequencies of NKT cells in the spleen of naïve C57BL/6 mice. n=9 for H$_2$O, 10 for ABX.

To dissect the mechanism of how the gut microbiome may mediate hepatic NKT cell accumulation, tumor-free mice were used. Naïve ABX administered C57BL/6 mice had more absolute and relative hepatic NKT cells than the controls (FIGS. 11A-11D). This increase was independent of gender (FIG. 12A), was also present in livers of BALB/c mice (FIGS. 12B and 12C), but not seen in the spleen (FIG. 12D).

Figure 13:
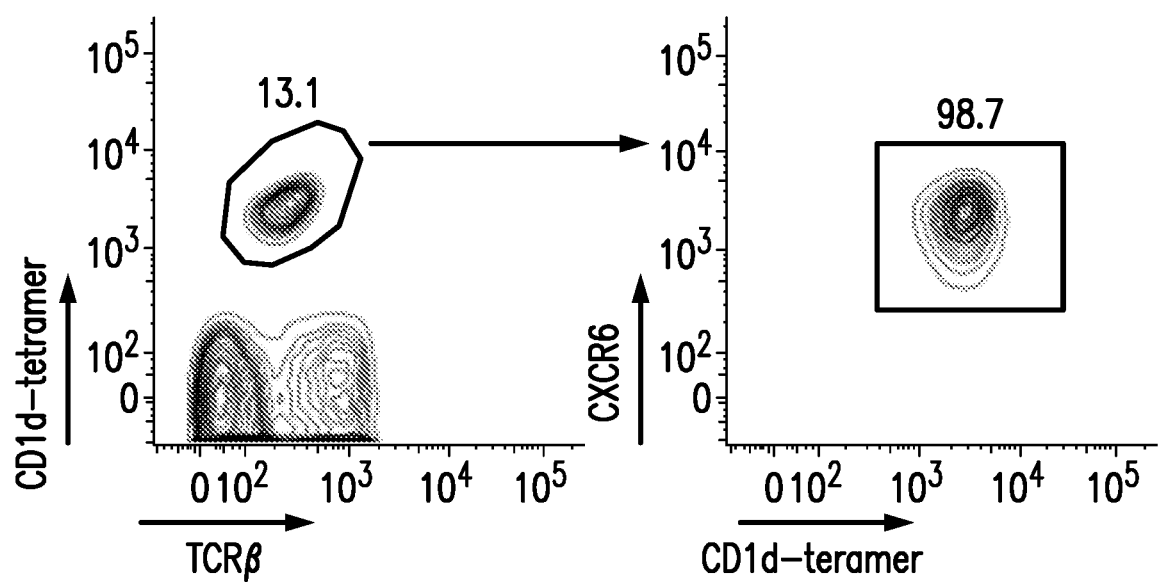
FIG. 13 presents dot plots showing representative CXCR6 staining in hepatic NKT cells measured by flow cytometry.
Figure 14A:
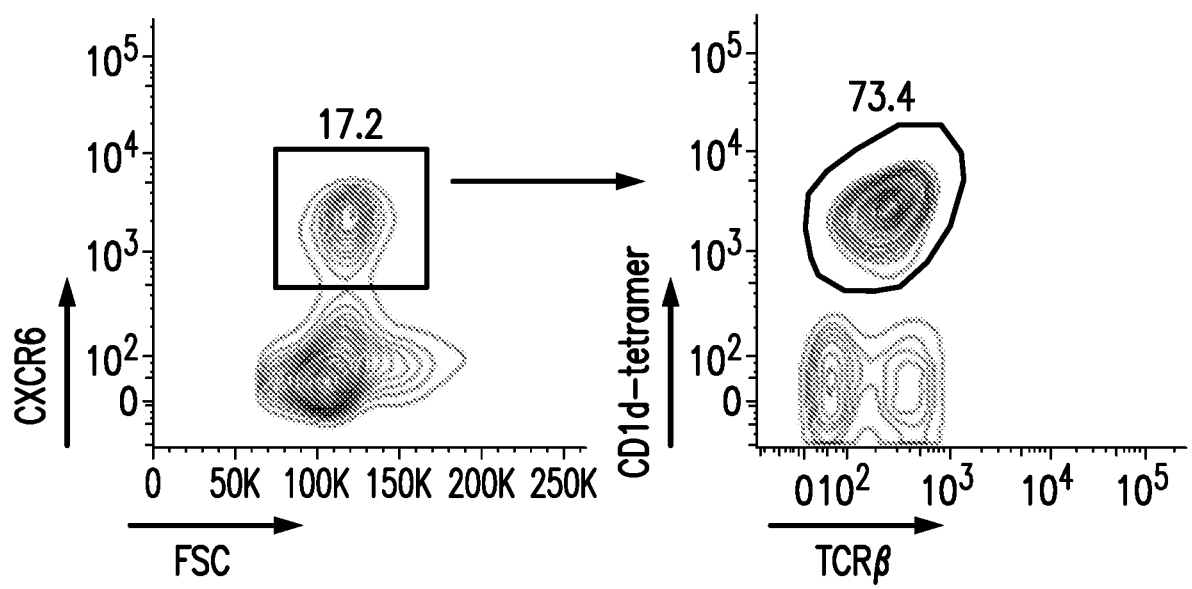
FIG. 14A presents dot plots showing representative NKT cells staining in CXCR6$^+$ liver infiltrating mononuclear cells measured by flow cytometry.
Figure 14B:
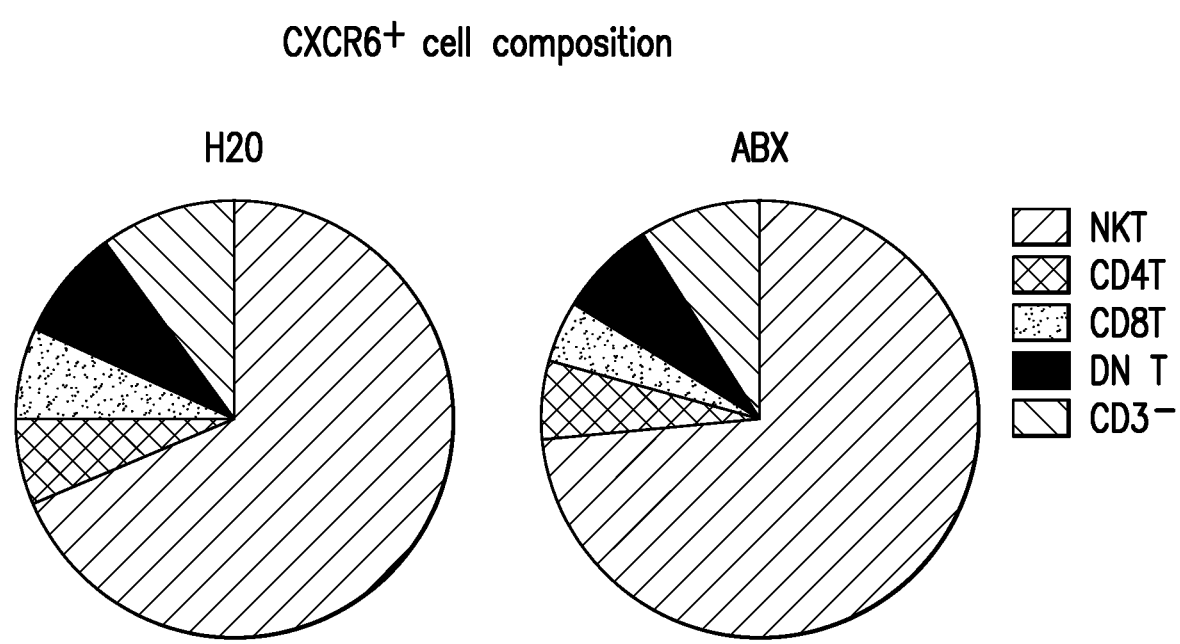
FIG. 14B presents pie charts showing the composition of CXCR6$^+$ liver infiltrating mononuclear cells in tumor-free C57BL/6 mice fed with ABX or H$_2$O. DN T: double negative T cells. H$_2$O condition: NKT 67.3%, CD4T 6.3%, CD8T 6.5%, DN T 7.7%, CD3$^-$ 9.8%; ABX condition: NKT 73.5%, CD4T 5.6%, CD8T 4.6%, DN T 7%, CD3$^-$ 8.9%.
Figure 15:
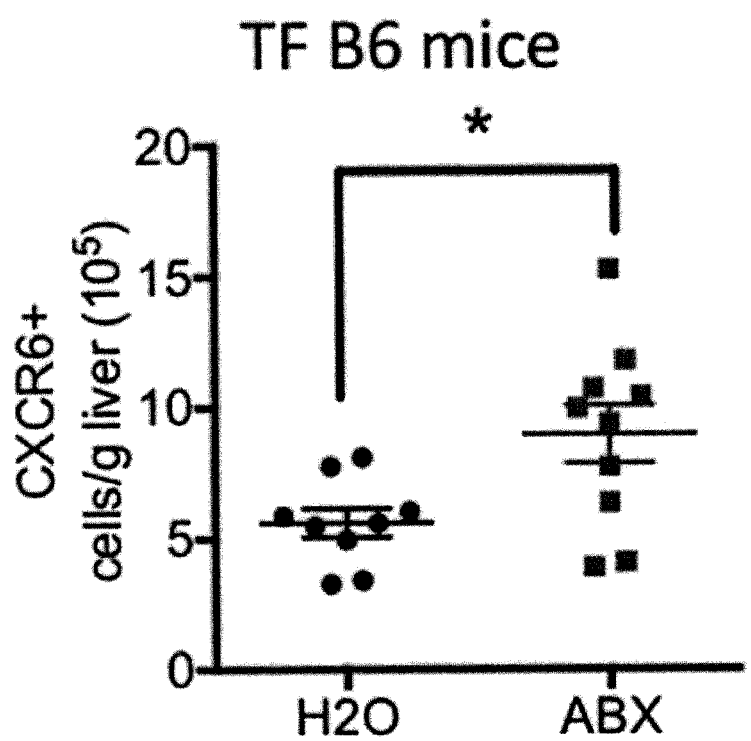
FIG. 15 is a dot plot showing levels of CXCR6$^+$ liver infiltrating cells in tumor-free C57BL/6 mice fed with ABX or H$_2$O, in accordance with embodiments of the invention. n=9 for H$_2$O, 10 for ABX. p<0.05, Student's t-test.
Figure 16:
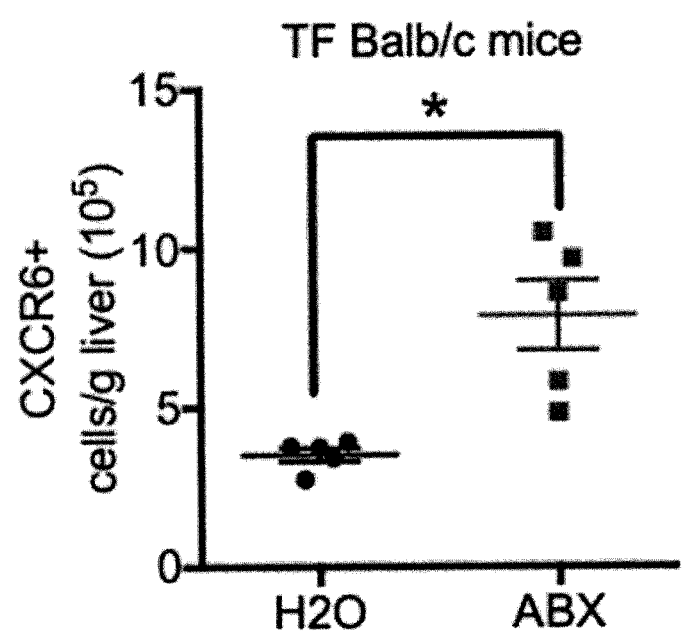
FIG. 16 is a dot plot showing CXCR6$^+$ liver infiltrating mononuclear cell counts in tumor-free BALB/c mice after ABX or H$_2$O administration, in accordance with embodiments of the invention. n=5, p<0.05, Student's t-test.
Figure 17A:
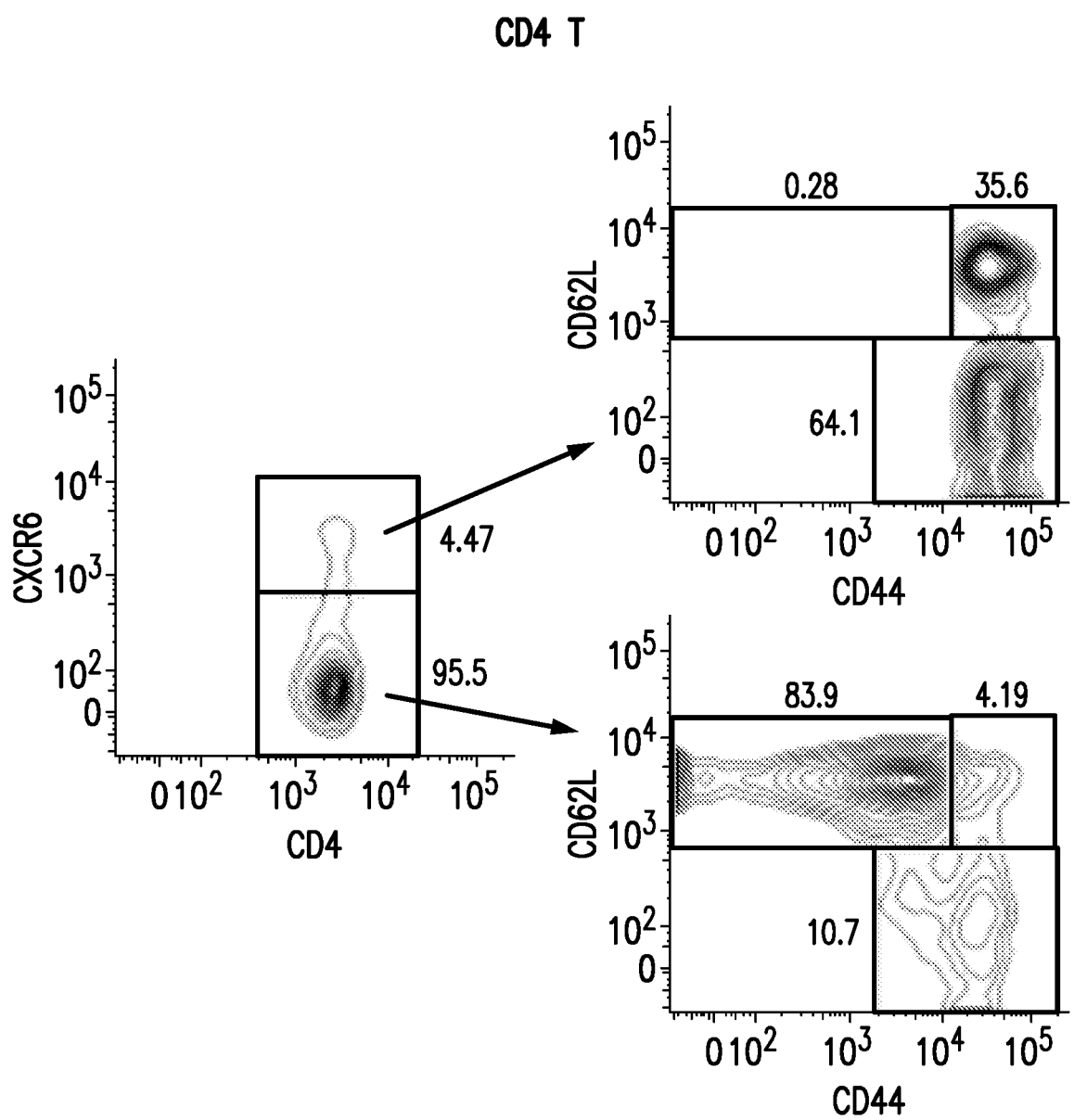
FIG. 17A presents dot plots showing representative CD44 and CD62L staining of CXCR6$^+$ CD4 T cells, in accordance with embodiments of the invention, in liver measured by flow cytometry.
Figure 17B:
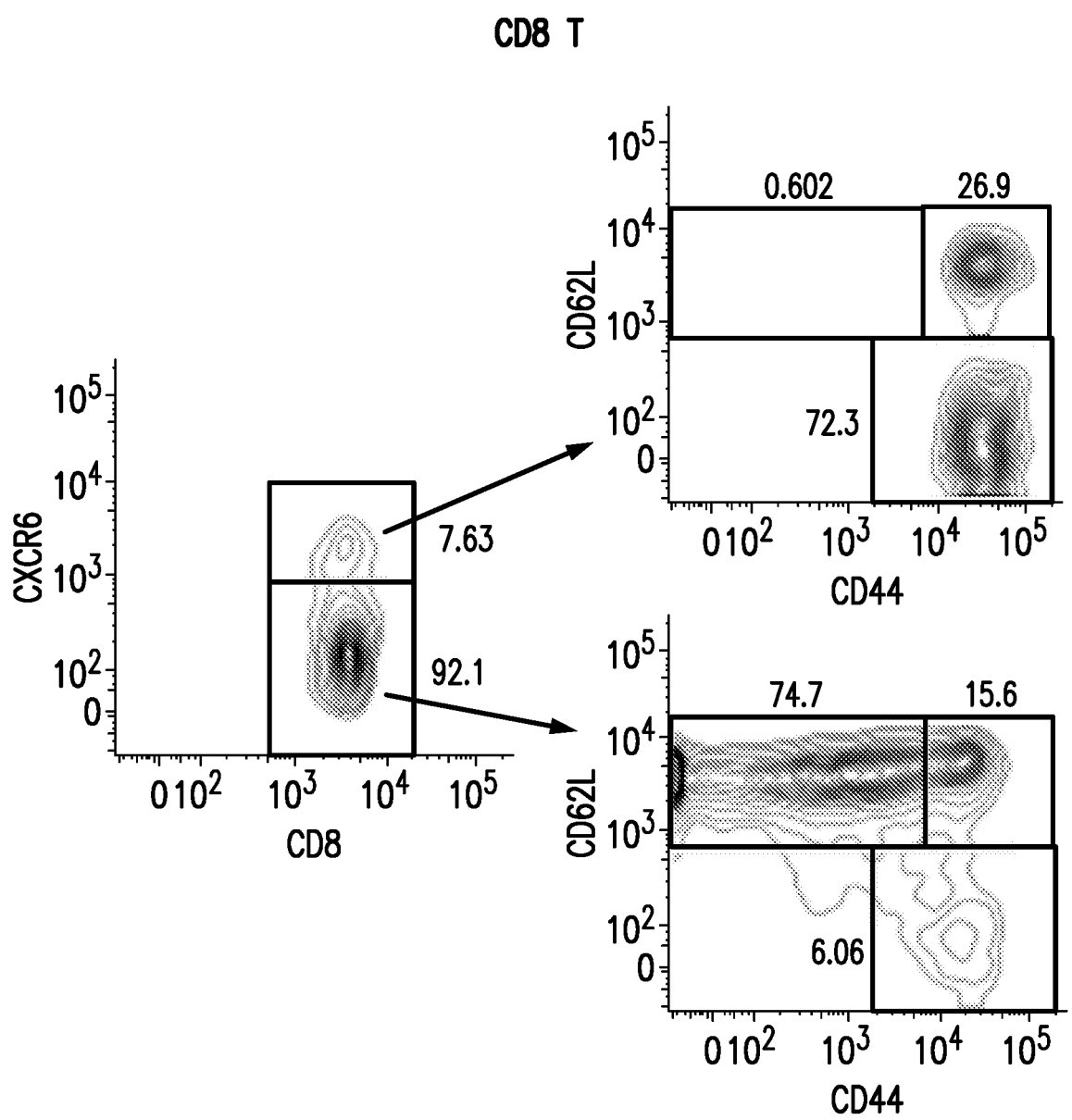
FIG. 17B presents dot plots showing representative CD44 and CD62L staining of CXCR6$^+$ CD8 T cells, in accordance with embodiments of the invention, in liver measured by flow cytometry.
Figure 17C:
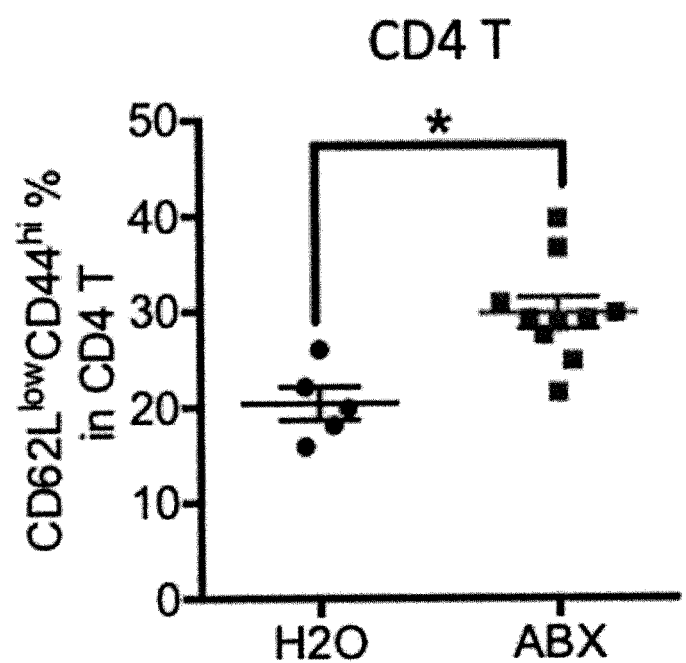
FIG. 17C is a dot plot showing frequency of effector/memory CD4 T cells, in accordance with embodiments of the invention, in liver of tumor-free C57BL/6 mice administered ABX or H$_2$O.
Figure 17D:
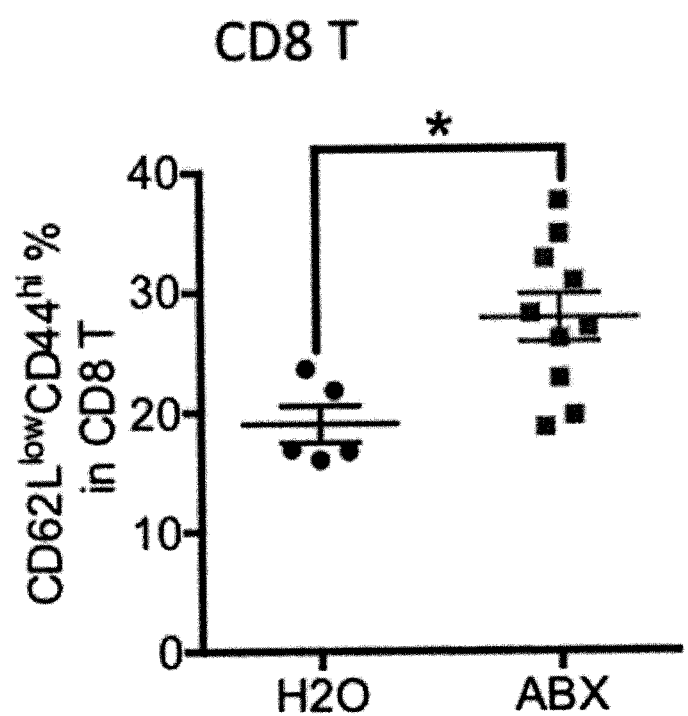
FIG. 17D is a dot plot showing frequency of effector/memory CD8 T cells, in accordance with embodiments of the invention, in liver of tumor-free C57BL/6 mice administered ABX or H$_2$O.

Chemokine receptor CXCR6 mediates NKT cell survival and accumulation in liver. All hepatic NKT cells expressed CXCR6 (FIG. 13). NKT cells comprise the majority of hepatic CXCR6$^+$ cells (~75%) (FIG. 14A), and its proportion did not change after ABX administration (FIG. 14B). Consistently, ABX administration caused an about two-fold increase of CXCR6$^+$ cells in the liver (FIG. 15). A similar increase of hepatic CXCR6$^+$ cells was observed in tumor-free BALB/c mice after ABX administration (FIG. 16). Since CXCR6 is also expressed on T cells, T cells were studied in this analysis. Both hepatic CXCR6$^+$ CD62L$^{low}$CD44$^{hi}$ effector/memory CD4$^+$ and CD8$^+$ T cells increased after ABX administration (FIGS. 17A-17D).

Figure 18A:
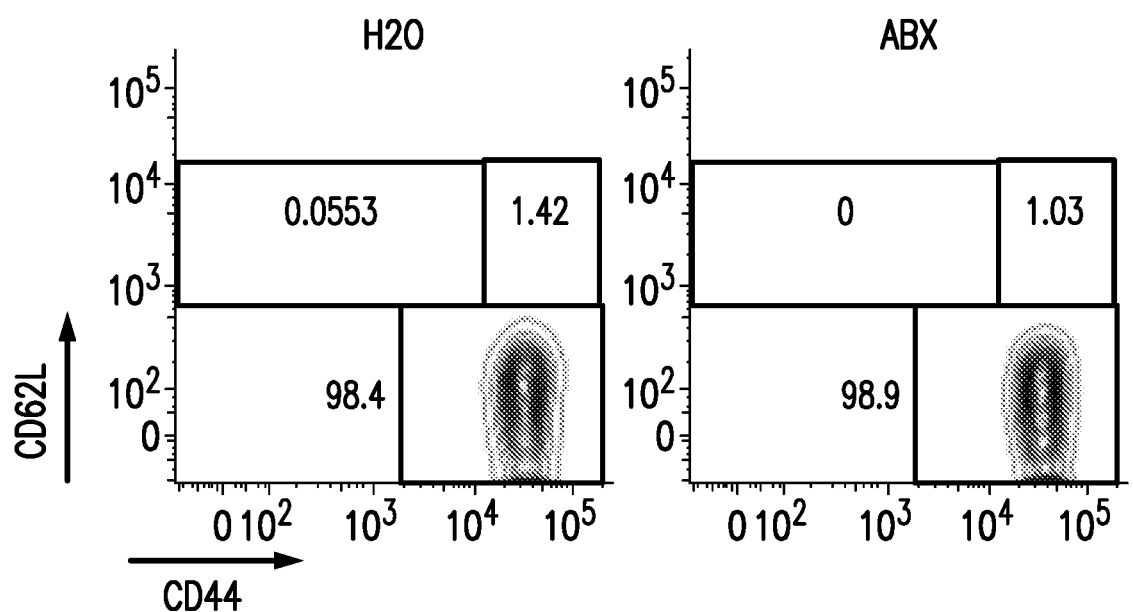
FIG. 18A presents dot plots showing representative CD44 and CD62L staining of hepatic NKT cells measured by flow cytometry.
Figure 18B:
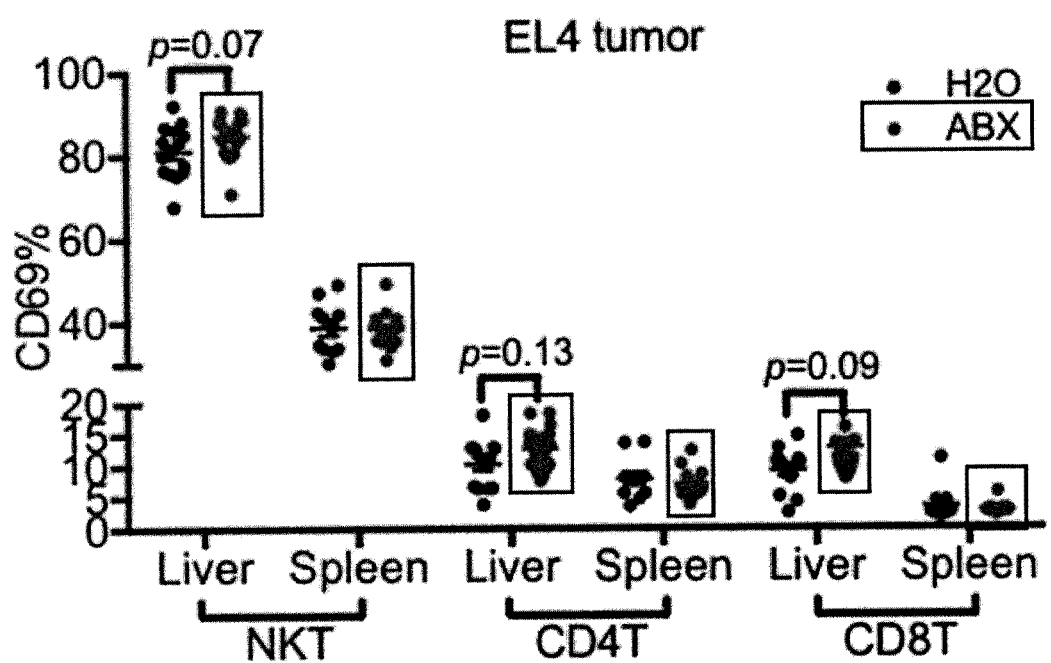
FIG. 18B is a dot plot showing frequencies of CD69$^+$, NKT, CD4 T and CD8 T cells in the liver and spleen from EL4-tumor bearing mice. n=15 for EL4-H$_2$O, 20 for EL4-ABX.
Figure 18C:
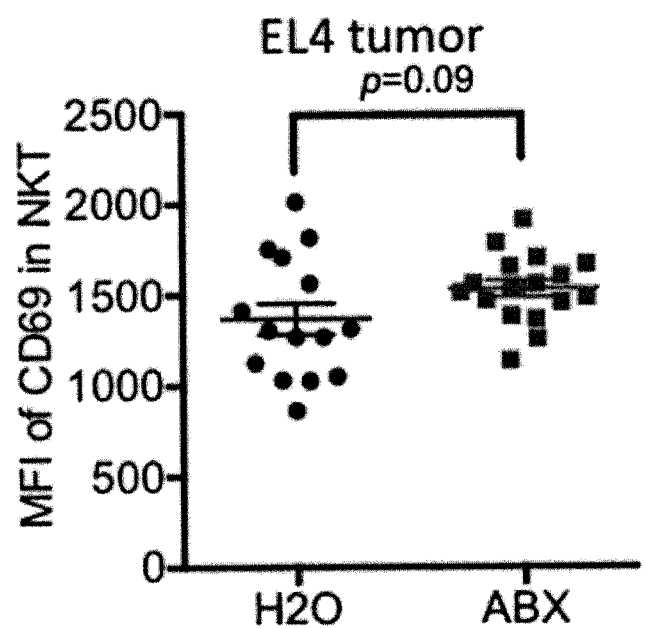
FIG. 18C is a dot plot showing MFI (mean fluorescence intensity) of CD69 in hepatic NKT cells. n=15 for H$_2$O, 18 for ABX.
Figure 18D:
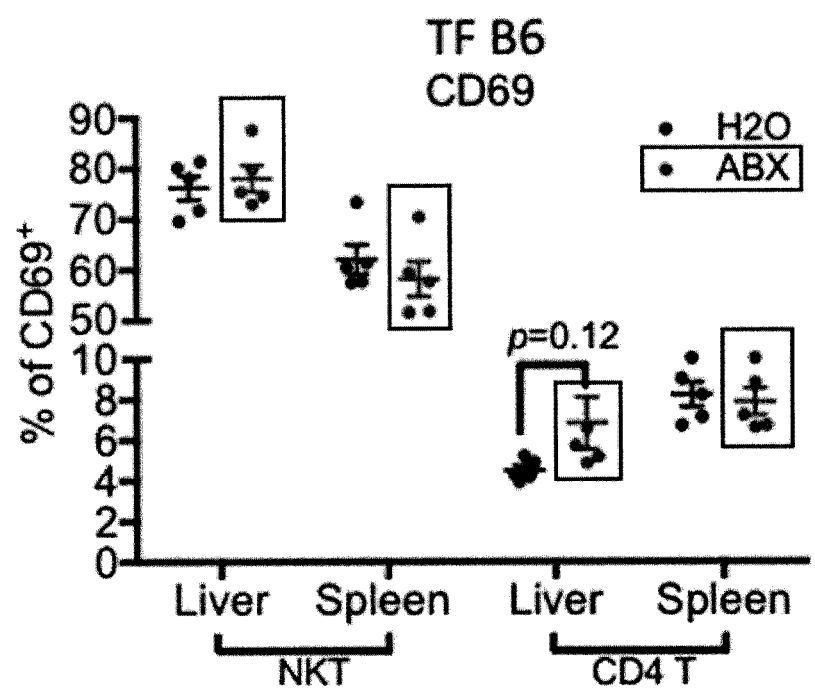
FIG. 18D is a dot plot showing CD69$^+$ levels of NKT and CD4 T cells in liver and spleen from tumor-free C57BL/6 mice. n=5, two-way ANOVA.
Figure 18E:
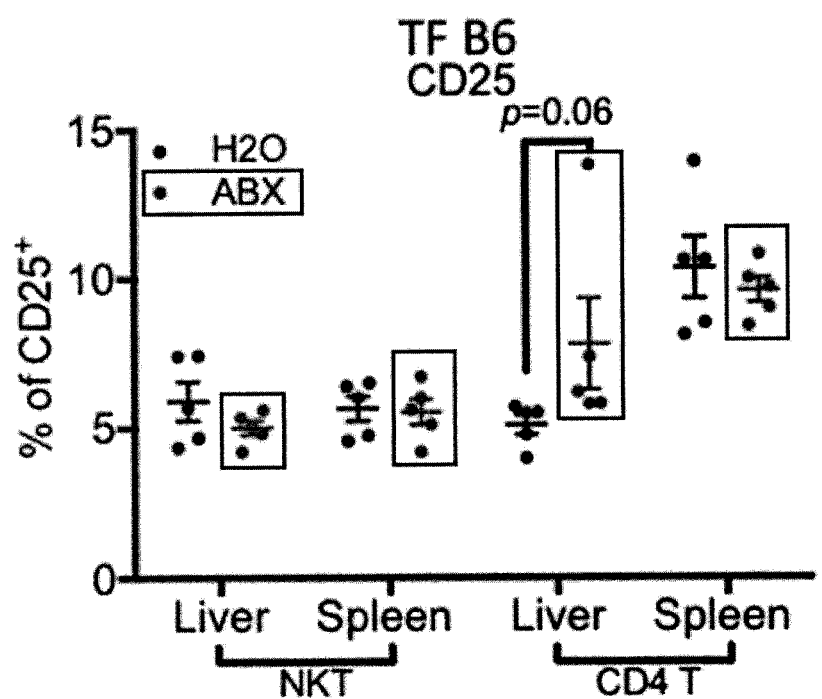
FIG. 18E is a dot plot showing CD25 levels of NKT and CD4 T cells in liver and spleen from tumor-free C57BL/6 mice. n=5, two-way ANOVA.
Figure 18F:
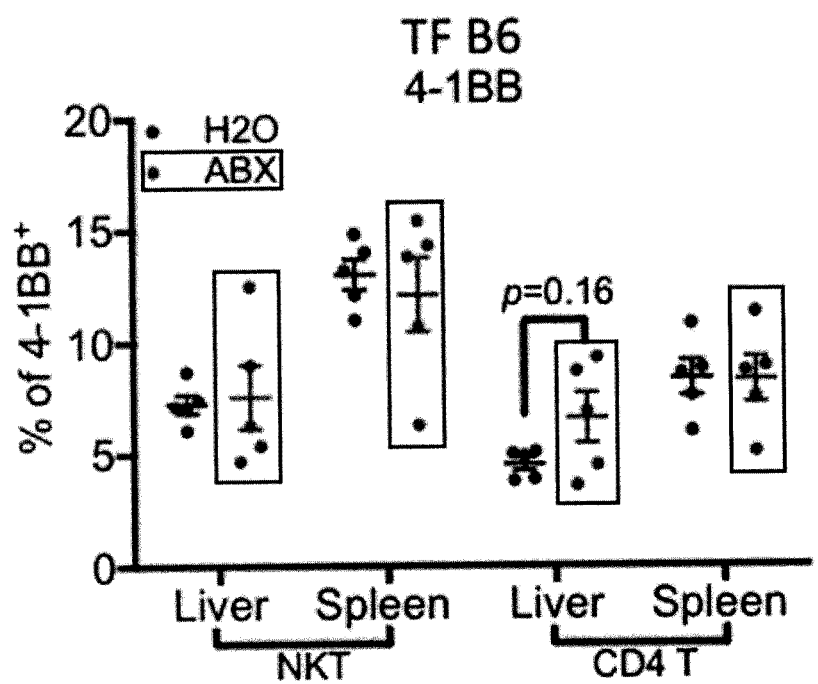
FIG. 18F is a dot plot showing 4-1BB levels of NKT and CD4 T cells in liver and spleen from tumor-free C57BL/6 mice. n=5, two-way ANOVA.
Figure 18G:
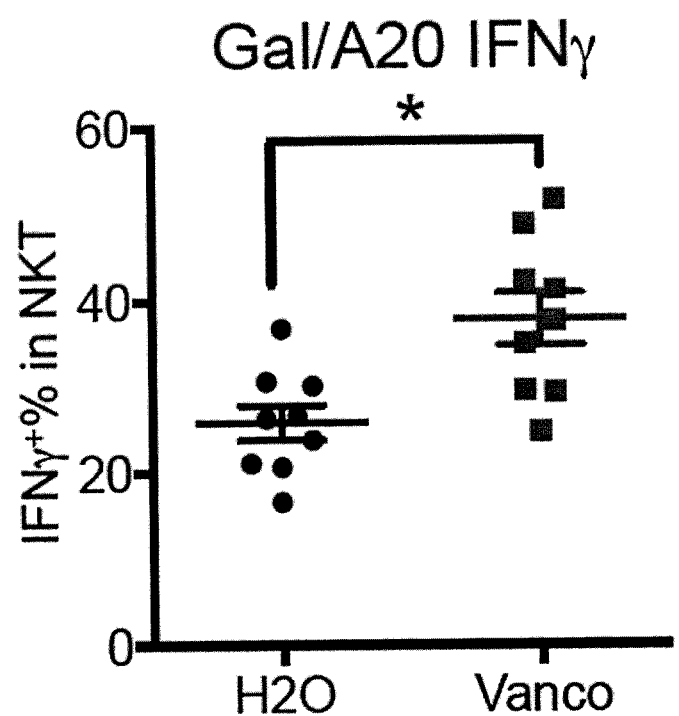
FIG. 18G is a dot plot showing IFNγ levels of hepatic NKT cells after in vivo stimulation by injecting aGalCer-loaded A20 tumor cells (Gal/A20) into vancomycin (Vanco) or H$_2$O-fed BABL/c mice. n=9, p<0.05, Student's t-test.
Figure 18H:
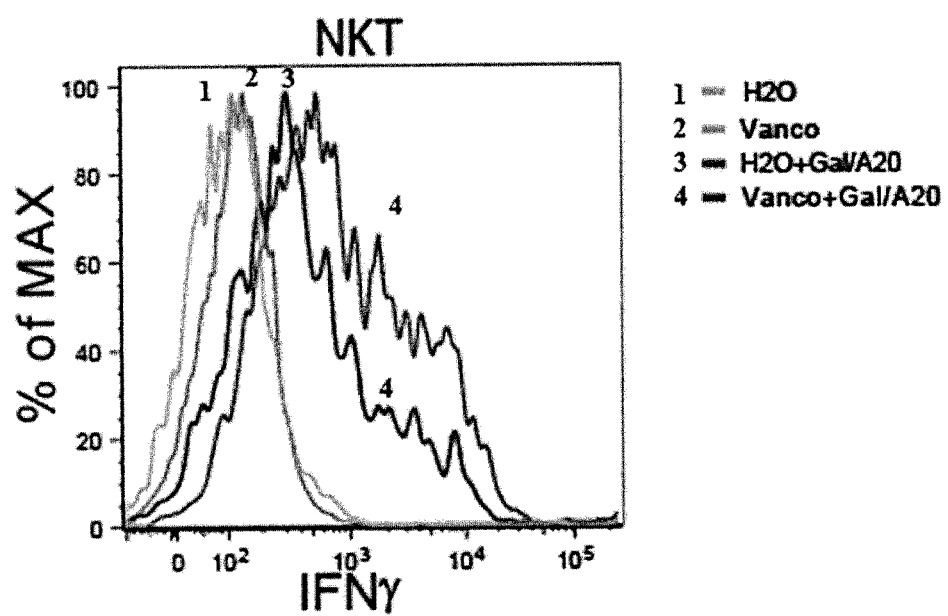
FIG. 18H is graph showing IFNγ levels. BALB/c mice fed on vancomycin or H$_2$O were given i.v. injection of $10^6$ α-galactosylceramide-loaded A20 tumor cells (Gal/A20) in the combination of brefeldin A (500 μg/mouse), where 3 hours later the level was measured by flow cytometry. n=9, p<0.05, Student's t-test.
Figure 18I:
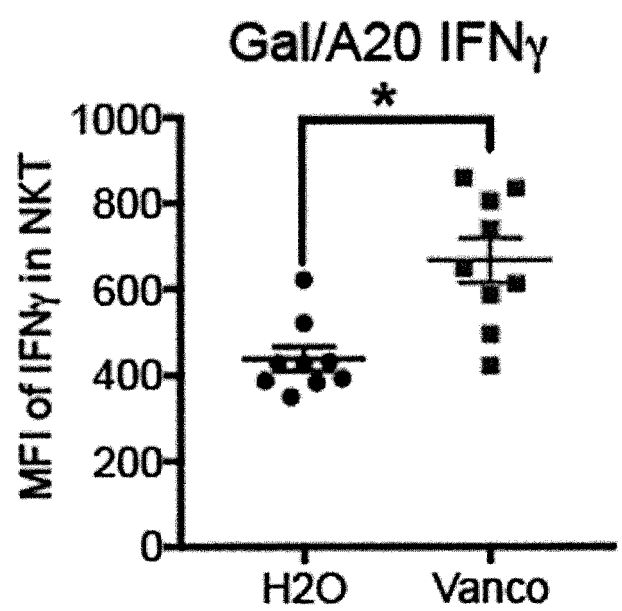
FIG. 18I is a dot plot showing IFNγ levels. BALB/c mice fed on vancomycin or H$_2$O were given i.v. injection of $10^6$ α-galactosylceramide-loaded A20 tumor cells (Gal/A20) in the combination of brefeldin A (500 μg/mouse), where 3 hours later the level was measured by flow cytometry. n=9, p<0.05, Student's t-test.
Figure 18J:
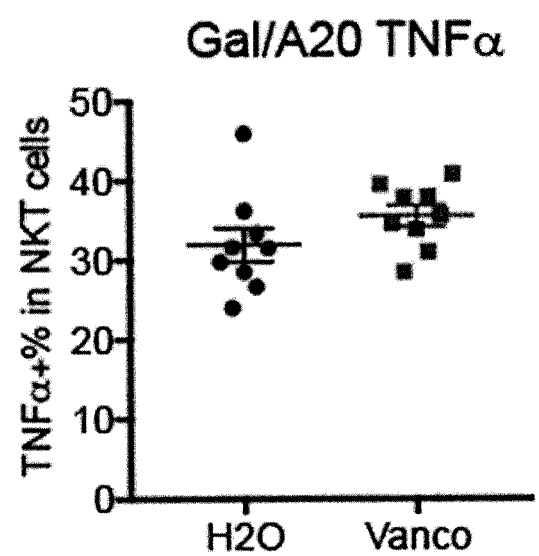
FIG. 18J is a dot plot showing TNFα levels. BALB/c mice fed on vancomycin or H$_2$O were given i.v. injection of $10^6$ α-galactosylceramide-loaded A20 tumor cells (Gal/A20) in the combination of brefeldin A (500 μg/mouse), where 3 hours later the level was measured by flow cytometry. n=9, p<0.05, Student's t-test.
Figure 18K:
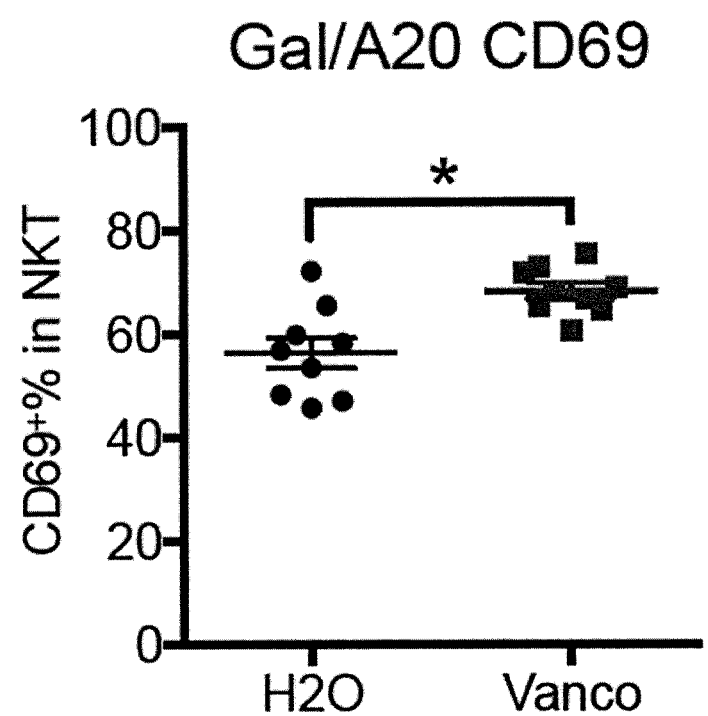
FIG. 18K is a dot plot showing CD69 levels of hepatic NKT cells after in vivo stimulation by injecting aGalCer-loaded A20 tumor cells (Gal/A20) into vancomycin (Vanco) or H$_2$O-fed BABL/c mice. n=9, p<0.05, Student's t-test.
Figure 18L:
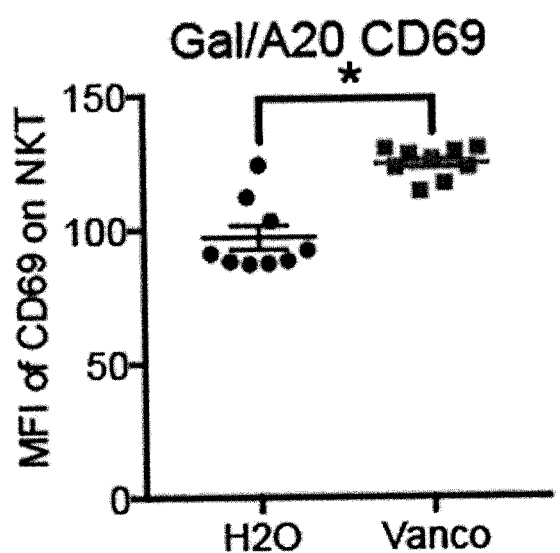
FIG. 18L is a dot plot showing CD69 levels. BALB/c mice fed on vancomycin or H$_2$O were given i.v. injection of $10^6$ α-galactosylceramide-loaded A20 tumor cells (Gal/A20) in the combination of brefeldin A (500 μg/mouse), where 3 hours later the level was measured by flow cytometry. n=9, p<0.05, Student's t-test.
Figure 18M:
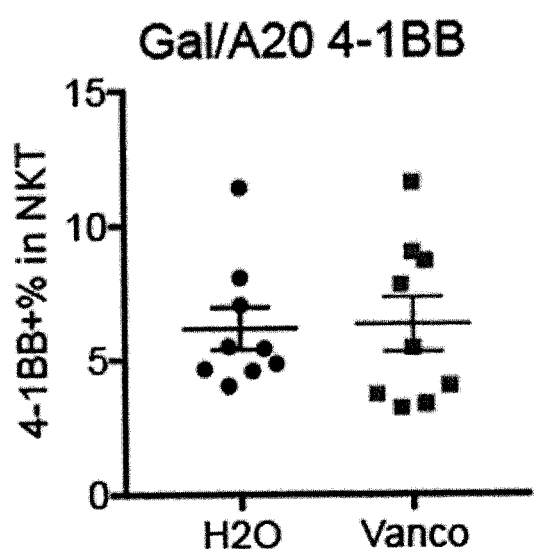
FIG. 18M is a dot plot showing 4-1BB levels. BALB/c mice fed on vancomycin or H$_2$O were given i.v. injection of $10^6$ α-galactosylceramide-loaded A20 tumor cells (Gal/A20) in the combination of brefeldin A (500 μg/mouse), where 3 hours later the level was measured by flow cytometry. n=9, p<0.05, Student's t-test.

Next, hepatic NKT cells were studied in further detail. The majority of NKT cells were CD44$^{hi}$CD62L$^{low}$ (FIG. 18A). Almost all hepatic NKT cells were CD69$^{hi}$ in both tumor-bearing (FIGS. 18B and 18C) and tumor-free mice (FIG. 18D). CD25 and 4-1BB, two additional activation markers, did not change in hepatic NKT cells after ABX administration (FIGS. 18E and 18F).

Figure 18N:
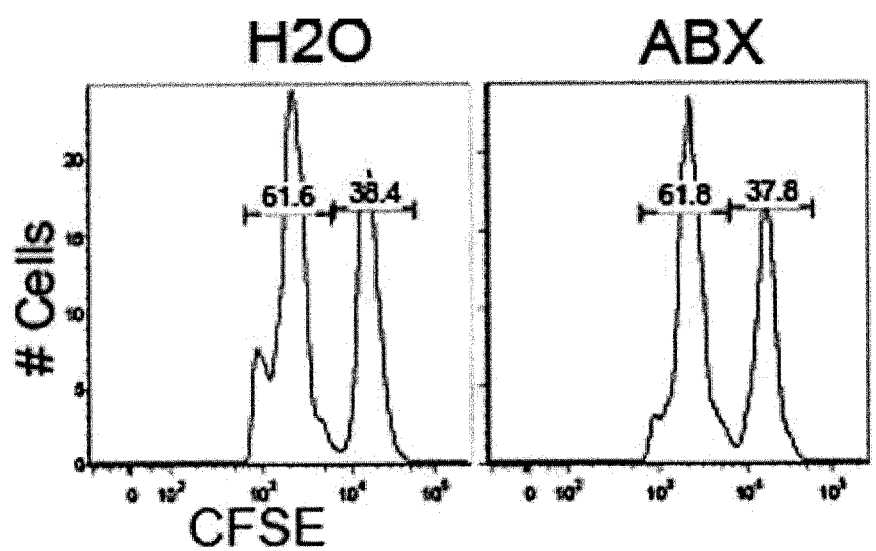
FIG. 18N presents graphs showing representative histogram of CFSE-labelled cells isolated from livers 16 hrs after injection in an in vivo cytotoxicity analysis of NKT cells of ABX- or H$_2$O administered mice. n=5 for H$_2$O, 4 for ABX.
Figure 18O:
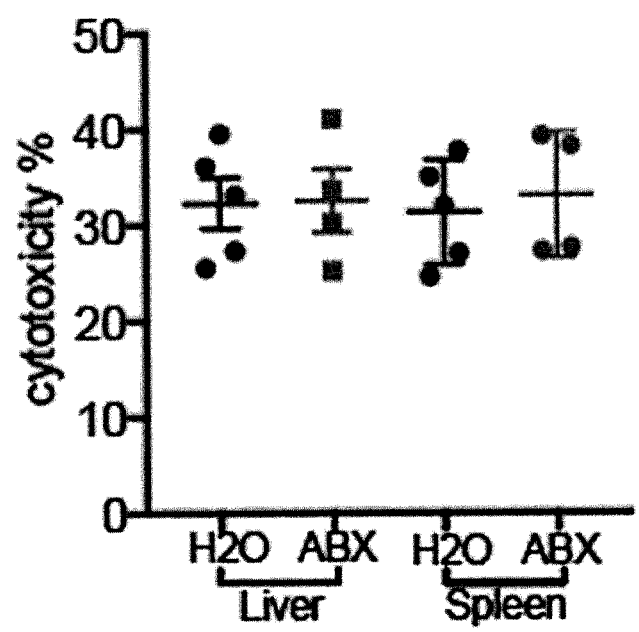
FIG. 18O is a dot plot showing quantification of FIG. 18N.

NKT cells can exert diverse functions via rapid release of cytokines after activation. Next, cytokine expression in NKT cells was measured after in vivo antigen-specific stimulation by injecting mice with α-galactosylceramide (aGalCer)-loaded tumor cells. Higher IFNγ was detected in hepatic NKT cells from mice received antibiotic administration; unlike IFNγ, TNFα level did not change; higher CD69 but no change of 4-1BB level was also observed suggests that the NKT cells are more active (FIGS. 18G-18M). IFNγ production of NKT cells has been proved to be a key for NKT cell-initiated tumor immunity. The results indicate that depleting gut commensal bacteria renders hepatic NKT cells a stronger anti-tumor function. The in vivo cytotoxicity of NKT cells was measured, but no change was observed after ABX administration (FIGS. 18N and 18O).

Figure 18P:
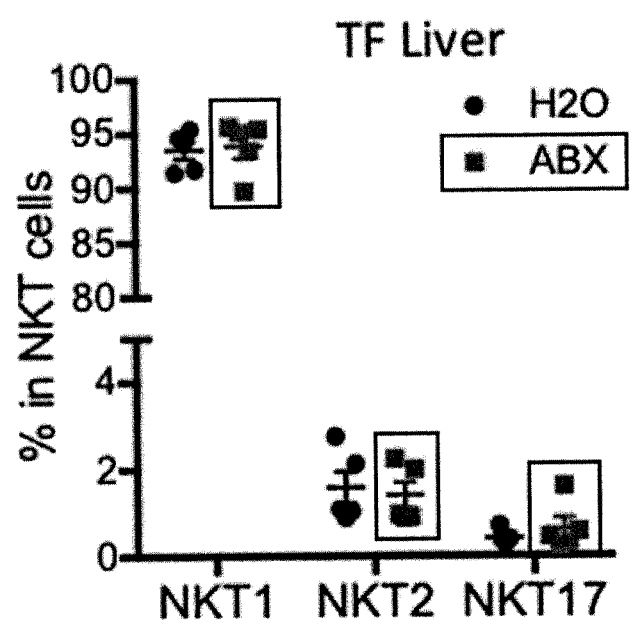
FIG. 18P is a dot plot showing NKT1 (T-bet$^{hi}$PLZF$^{lo}$), NKT2 (T-bet$^{lo}$PLZF$^{hi}$), and NKT17 (T-bet$^{lo}$PLZF$^{int}$) levels in hepatic NKT cells.
Figure 19A:
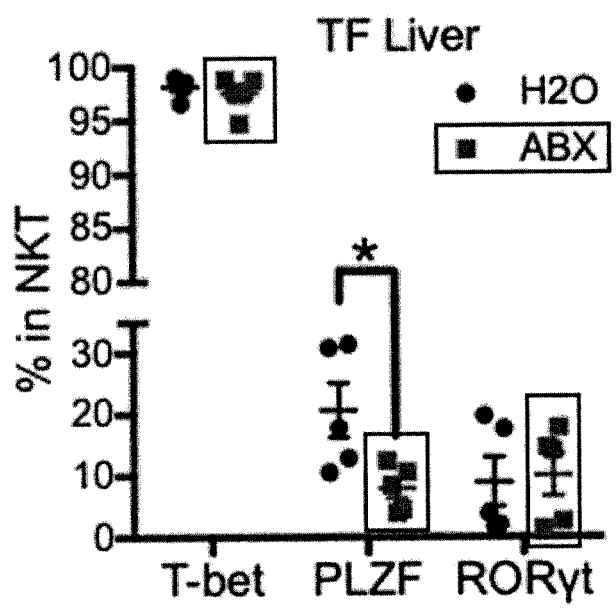
FIG. 19A is a dot plot showing T-bet$^+$, PLZF$^+$, and RORγ$^+$ levels of NKT in the liver of tumor-free C57BL/6 mice after ABX or H$_2$O administration. n=5, p<0.05, two-way ANOVA.
Figure 19B:
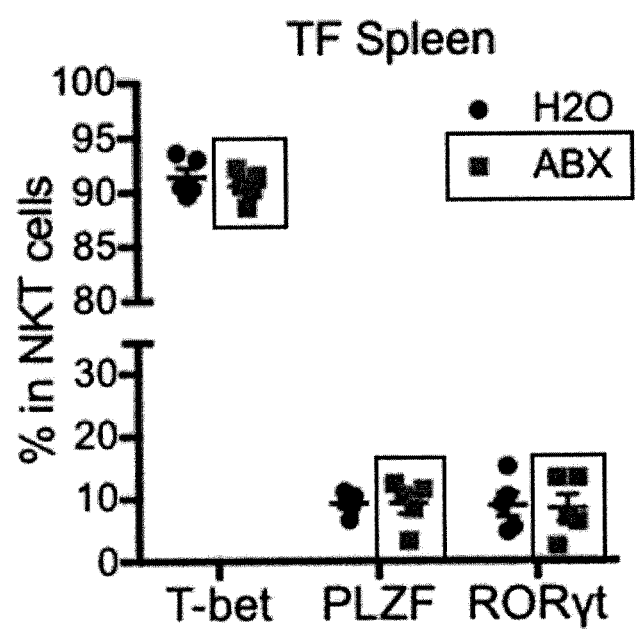
FIG. 19B is a dot plot showing T-bet$^+$, PLZF$^+$, and RORγ$^+$ levels of NKT in the spleen of tumor-free C57BL/6 mice after ABX or H$_2$O administration. n=5, p<0.05, two-way ANOVA.
Figure 19C:
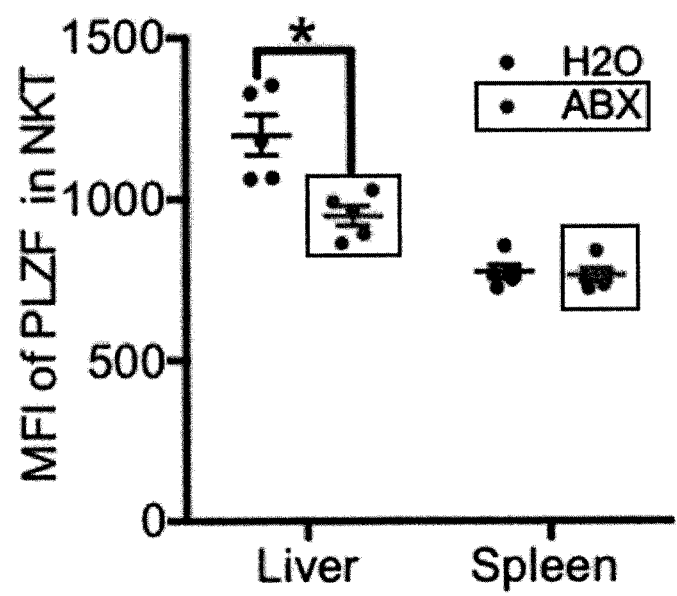
FIG. 19C is a dot plot showing MFI of PLZF in hepatic NKT cells. n=5, p<0.05, two-way ANOVA.

NKT subpopulations were studied based on the expression of transcriptional factors (Lee et al., Nat. Immunol., 14: 1146-1154 (2013), incorporated by reference herein). The majority of hepatic NKT cells were NKT1, and the levels of NKT subsets did not change (FIG. 18P). Interestingly, PLZF, which is involved in NKT development, significantly decreased after ABX administration (FIG. 19A). The decrease was not found in the spleen (FIGS. 19B and 19C).

Figure 20A:
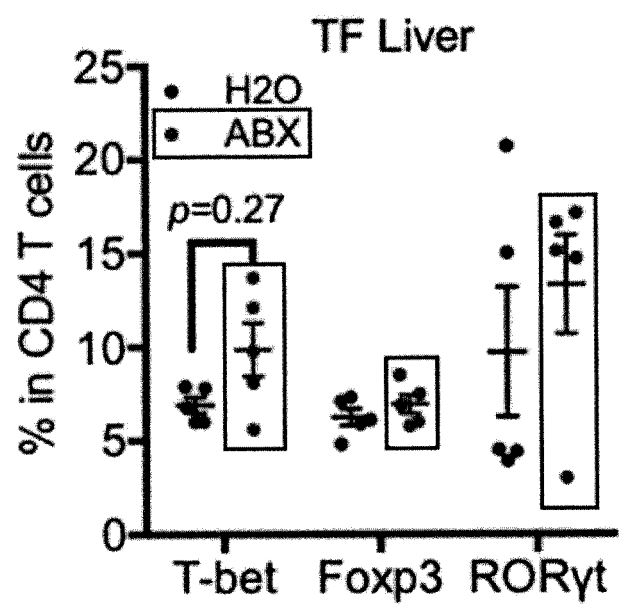
FIG. 20A is a dot plot showing T-bet$^+$, Foxp3 and RORγ$^+$ levels of CD4 T cells in the liver of C57BL/6 mice administered ABX or H$_2$O. n=5.
Figure 20B:
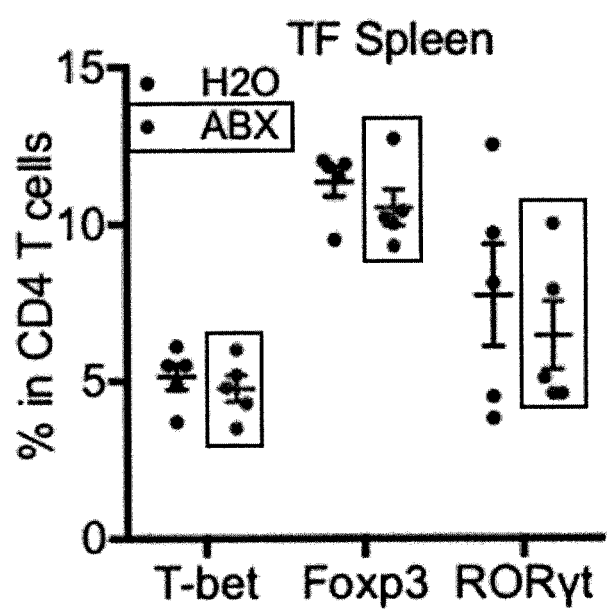
FIG. 20B is a dot plot showing T-bet$^+$, Foxp3 and RORγ$^+$ levels of CD4 T cells in the spleen of C57BL/6 mice administered ABX or H$_2$O. n=5.
Figure 21A:
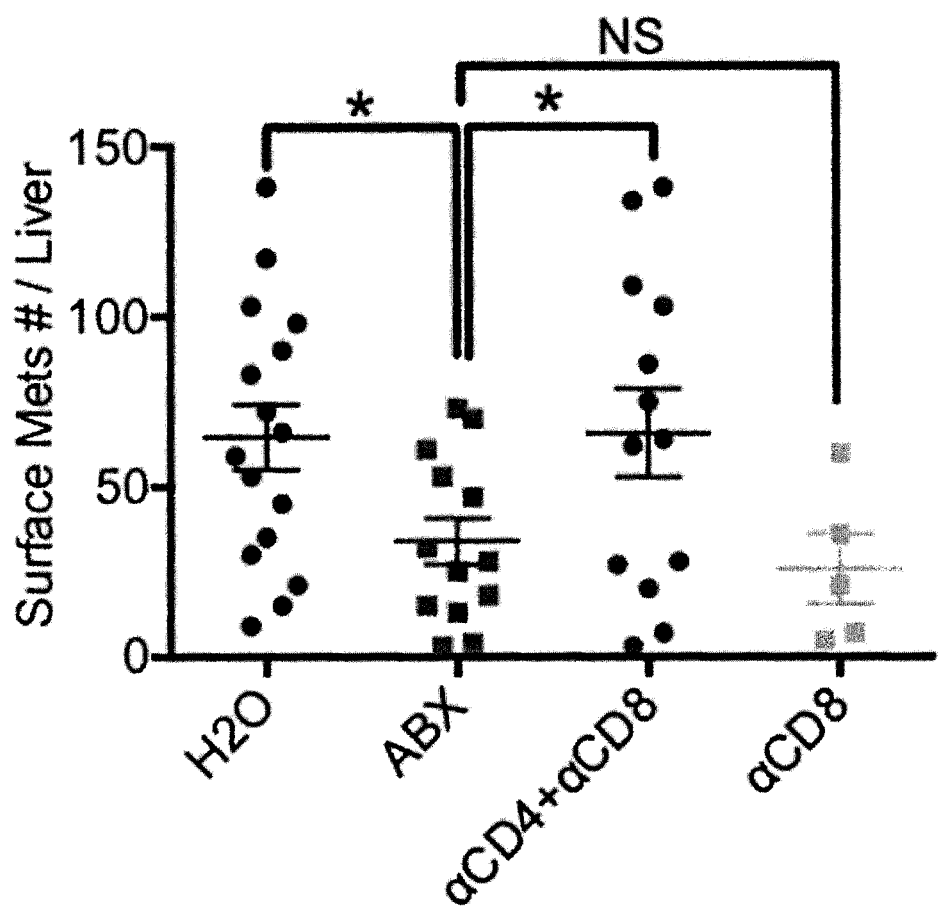
FIG. 21A is a dot plot showing cumulative liver metastasis counts, in accordance with embodiments of the invention, in 5 week old B6 mice administered ABX or H$_2$O for 3 weeks, intrasplenically injected with B16 tumor cells. One day before tumor injection the mice were given intraperitoneal (i.p.) injection of a combination of anti-CD4 (500 μg/mouse) and anti-CD8 (200 μg/mouse) antibodies or anti-CD8 alone (200 μg/mouse) for T cell depletion. Measurements were taken 1.5 weeks after injection. n=16 for H$_2$O, 14 for ABX, 13 for anti-CD4+anti-CD8, 5 for anti-CD8. p<0.05, one-way ANOVA.
Figure 21B:
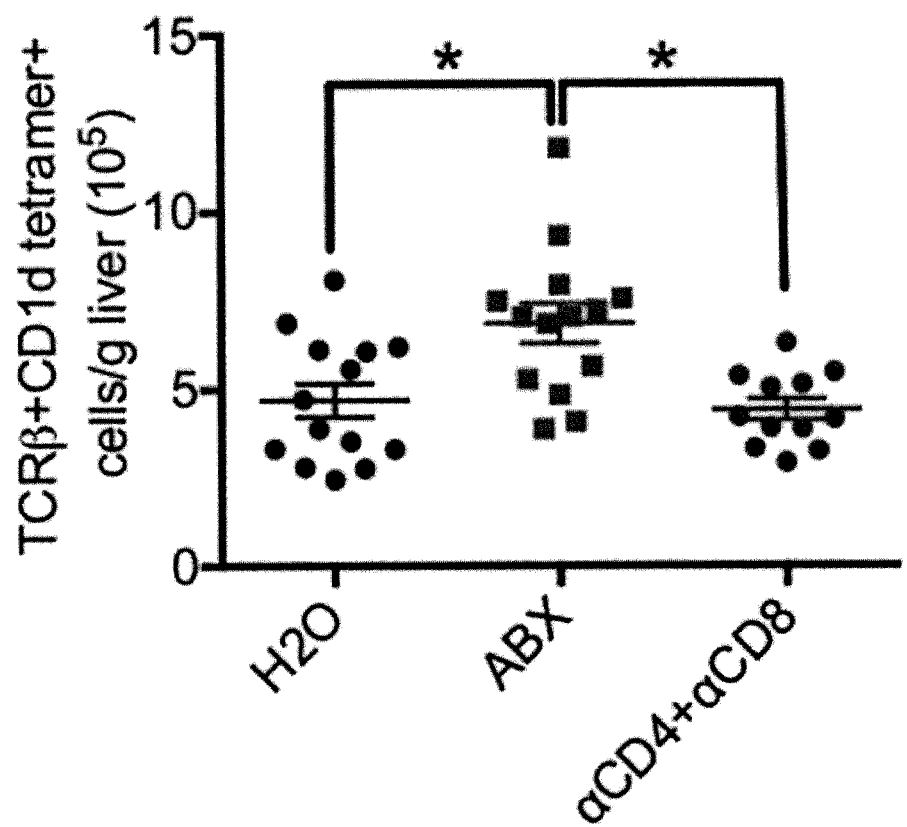
FIG. 21B is a dot plot showing hepatic NKT cell levels, in accordance with embodiments of the invention, in 5 week old B6 mice administered ABX or H$_2$O for 3 weeks, then intrasplenically injected with B16 tumor cells. One day before tumor injection the mice were given i.p. injection of a combination of anti-CD4 (500 μg/mouse) and anti-CD8 (200 μg/mouse) antibodies or anti-CD8 alone (200 μg/mouse) for T cell depletion. Measurements were taken 1.5 weeks after injection. n=16 for H$_2$O, 14 for ABX, 13 for anti-CD4+anti-CD8, 5 for anti-CD8. p<0.05, one-way ANOVA.
Figure 21C:
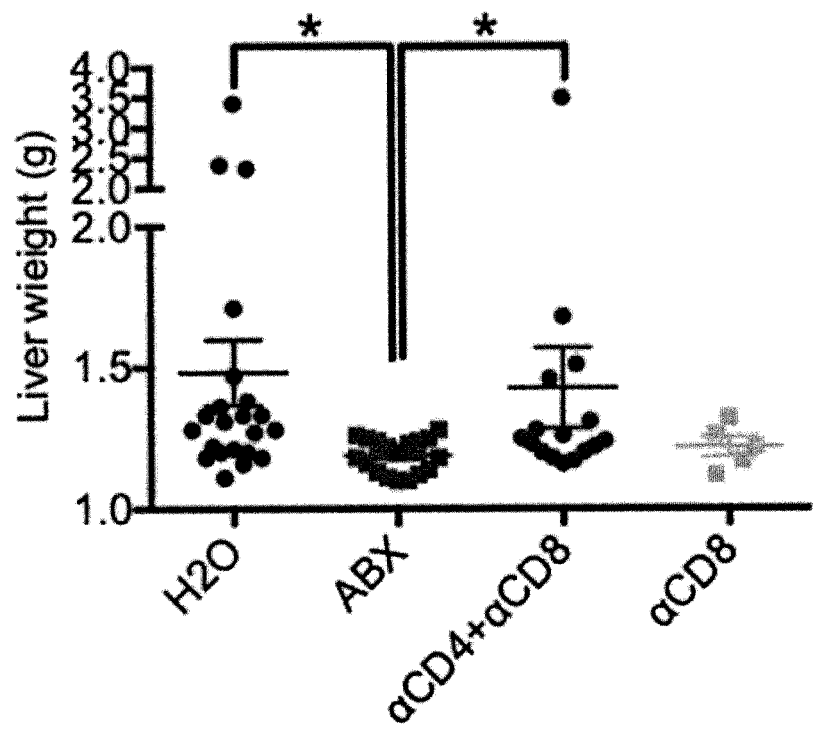
FIG. 21C is a dot plot showing liver weight of mice that received lymphocyte depletion, in accordance with embodiments of the invention. n=16 for H$_2$O, 14 for ABX, 13 for anti-CD4+anti-CD8, 5 for anti-CD8. p<0.05, one-way ANOVA.
Figure 21D:
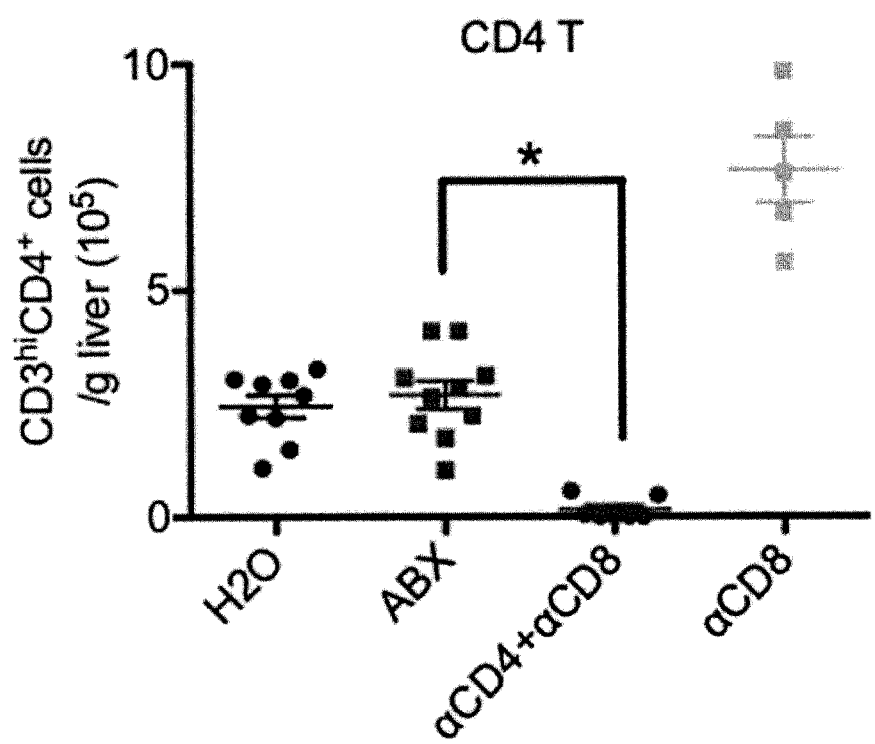
FIG. 21D is a dot plot showing hepatic CD4 T cell levels of mice that received lymphocyte depletion, in accordance with embodiments of the invention. n=16 for H$_2$O, 14 for ABX, 13 for anti-CD4+anti-CD8, 5 for anti-CD8. p<0.05, one-way ANOVA.
Figure 21E:
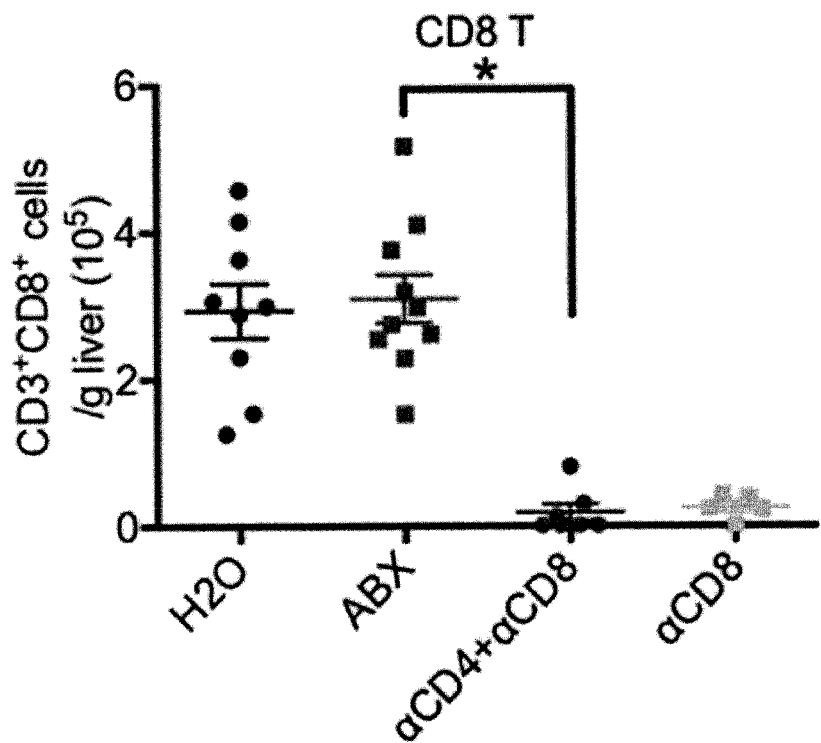
FIG. 21E is a dot plot showing hepatic CD8 T cell levels of mice that received lymphocyte depletion, in accordance with embodiments of the invention. n=16 for H$_2$O, 14 for ABX, 13 for anti-CD4+anti-CD8, 5 for anti-CD8. p<0.05, one-way ANOVA.

Regulatory T cells (Treg) are important modulators in tumor progression. The gut microbiome has been reported to affect Treg population. Treg levels were measured, but no change of Foxp3$^+$CD4$^+$ population was seen in spleen or liver of ABX-administered C57BL/6 (FIGS. 20A and 20B) or BALB/c mice.

Together, these results show that altering the gut microbiome caused accumulation of hepatic NKT and effector memory CD4$^+$ or CD8$^+$ T the NKT cells are more active and produce higher level of IFNγ when encounter antigen-loaded tumor cells. All these changes favor a tumor-rejecting environment.

Hepatic NKT Cells Mediate Tumor Inhibition

Antibody-mediated cell depletion was performed to investigate the specific function of individual immune cell populations controlling liver tumor immunity in ABX administered mice. ABX-administered C57BL/6 mice were given intrasplenic injection of B16 tumor cells. T cell depletion was performed one day before tumor injection. Removing all the three major hepatic T cell subsets (CD4$^+$ T, CD8$^+$ T and NKT cells) completely reversed the inhibition of liver metastasis caused by elimination of gut commensal bacteria (FIGS. 21A-21E), while depleting CD8$^+$ T cells alone had minor effects.

Figure 22:
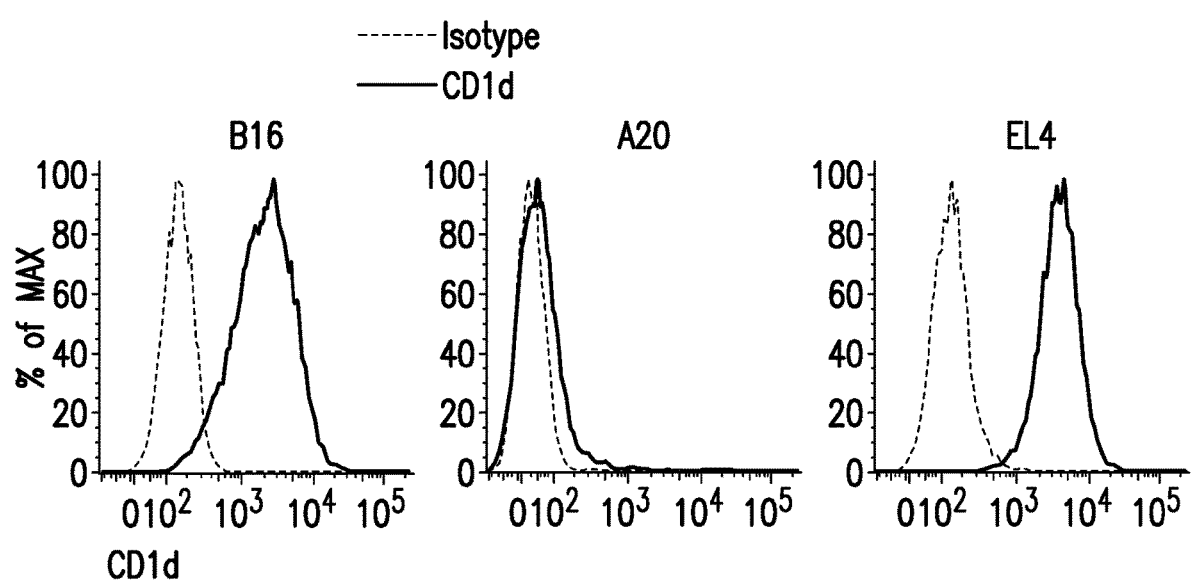
FIG. 22 presents line graphs showing CD1d expression levels in B16, A20 and EL4 tumor cells determined by flow cytometry.
Figure 23:
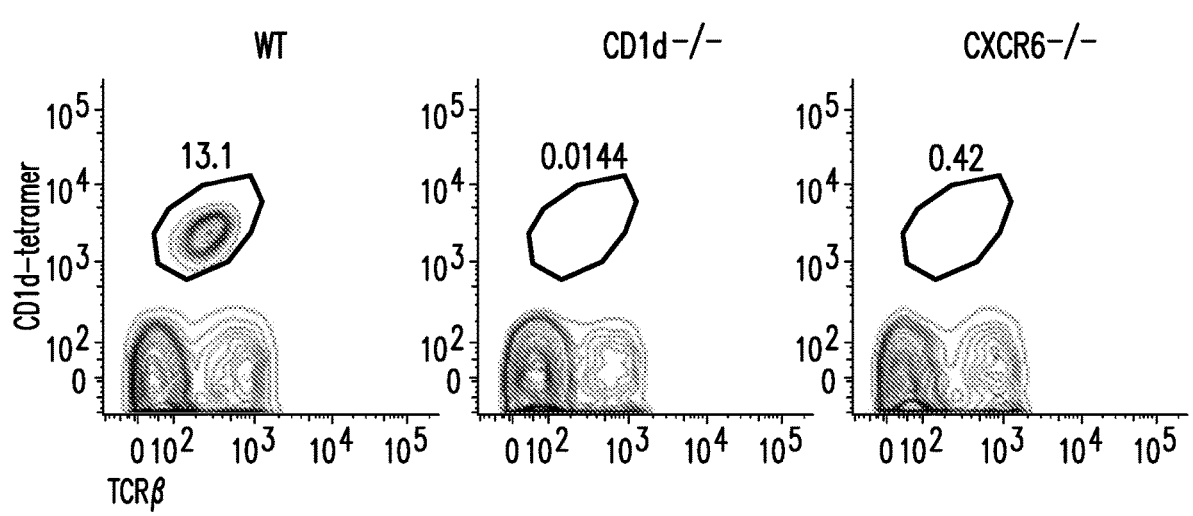
FIG. 23 presents dot plots showing representative hepatic NKT staining in CXCR6$^{-/-}$ and CD1d$^{-/-}$ mice measured by flow cytometry.
Figure 24:
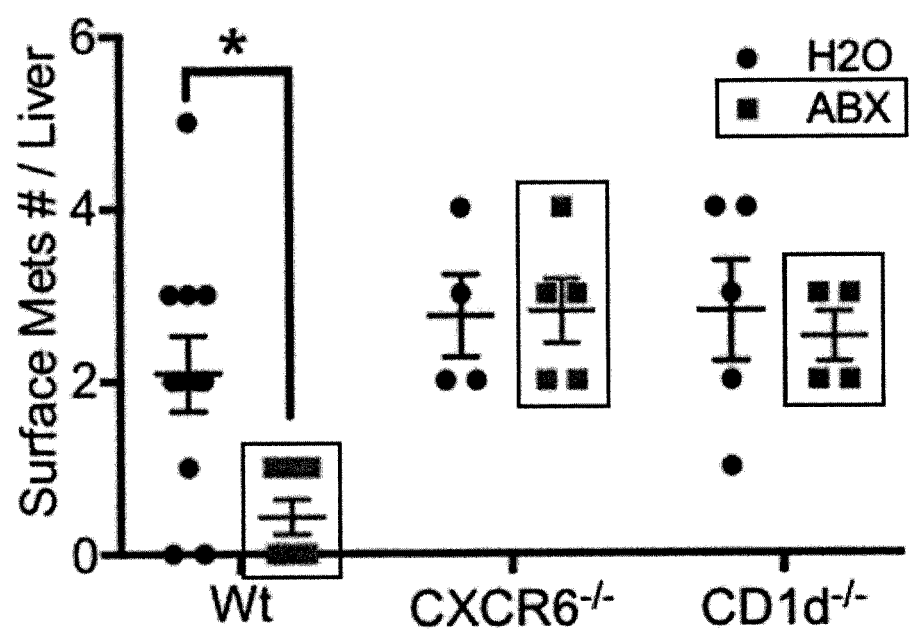
FIG. 24 is a dot plot showing liver metastases determined for CXCR6$^{-/-}$, CD1d$^{-/-}$ and wildtype 5 week old mice administered ABX or H$_2$O for 3 weeks and then given EL4 tumor cell via tail vein injection. Measurements were taken 3 weeks after injection. Cumulative data are shown. n=10 for Wt-H$_2$O, 7 for Wt-ABX, 4 for CXCR6$^{-/-}$-H$_2$O, 5 for CXCR6$^{-/-}$-ABX, 5 for CD1d$^{-/-}$-H$_2$O, 4 for CD1d$^{-/-}$-ABX. p<0.05, two-way ANOVA.
Figure 25A:
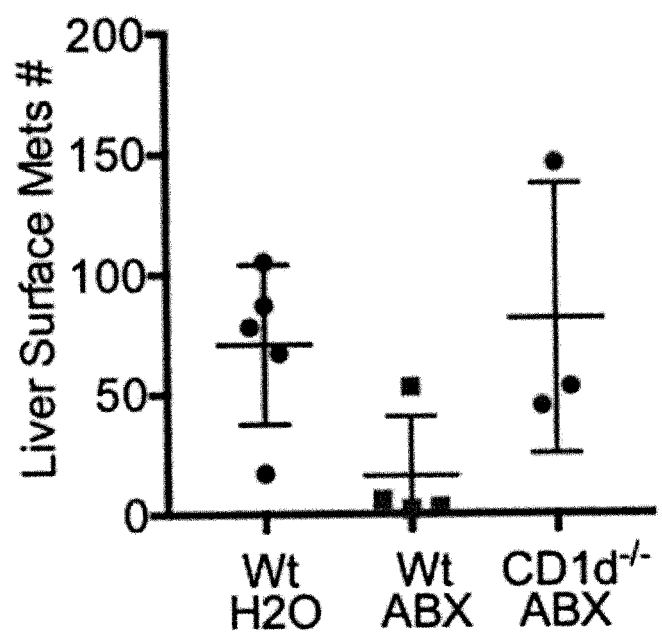
FIG. 25A is a dot plot showing liver metastases determined for WT and CXCR6$^{-/-}$ mice (starting at 5 weeks old) administered ABX or H$_2$O for 3 weeks and then given intrasplenic B16 tumor cell injection. Measurements were taken 1.5 weeks after injection. Liver surface metastatic tumor counts are shown.
Figure 25B:
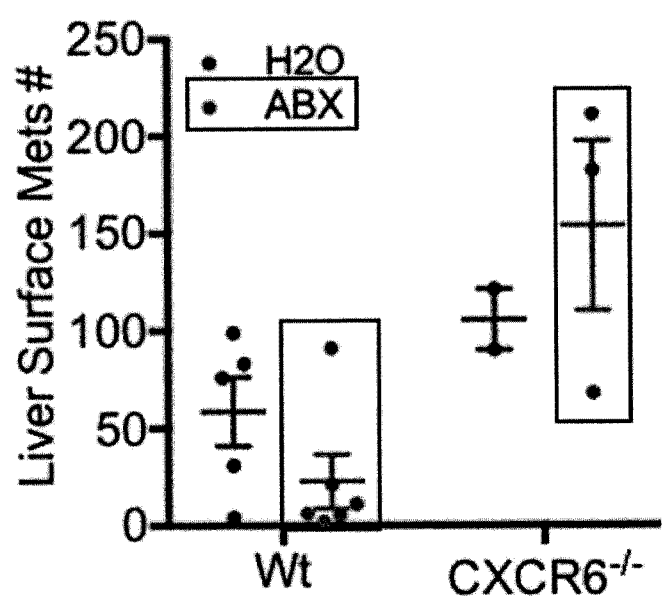
FIG. 25B is a dot plot showing liver metastases determined for WT and CXCR6$^{-/-}$ mice (starting at 5 weeks old) administered ABX or H$_2$O for 3 weeks and then given intrasplenic B16 tumor cell injection. Measurements were taken 1.5 weeks after injection. Liver surface metastatic tumor counts are shown.

NKT cells are known to have anti-tumor function and can directly kill CD1d expressing tumors. All three tested tumor models (B16, EL4 and A20) expressed CD at different levels (FIG. 22). To investigate the role of NKT cells in this setting, CD1d knockout and CXCR6 knockout mice were used. CD1d knockout mice completely lack NKT cells, while CXCR6 knockout mice have a selective NKT deficiency in the liver. Loss of hepatic NKT cells in these mice was confirmed (FIG. 23). Liver tumors were induced by intravenous injection of EL4 tumor cells (Smyth et al., J. Exp. Med., 191: 661-668 (2000), incorporated by reference herein). Depleting gut microbiome reduced EL4 liver tumor burden in wild-type mice. In contrast, no reduction of liver tumor was found in either CD1d knockout or CXCR6 knockout mice after ABX administration (FIG. 24). B16 tumor cell intrasplenic injection was repeated in CD knockout or CXCR6 knockout mice. Similar results were observed (FIGS. 25A and 25B), indicating that hepatic NKT cells are involved in tumor growth in the liver induced by changes in the gut microbiome.

Bile Acids/CXCL16/CXCR6 Axis Controls Hepatic NKT Accumulation

Figure 26:
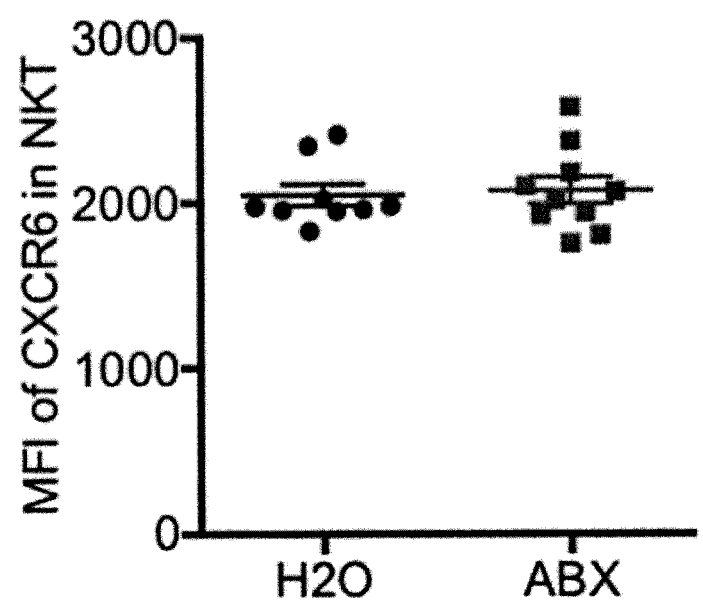
FIG. 26 is a dot plot showing MFI of CXCR6 in hepatic NKT cells from ABX or H$_2$O administered mice. n=9 for H$_2$O, 10 for ABX.

Next, the mechanism of how gut commensal bacteria control hepatic NKT accumulation was studied. Virtually all hepatic NKT cells express CXCR6 (FIG. 13), and ABX administration increased the accumulation of CXCR6$^+$ cells into the liver (FIG. 15), while CXCR6 MFI did not change on NKT cells (FIG. 26). Therefore, CXCL16, the only ligand for CXCR6, was further studied.

Figure 27A:
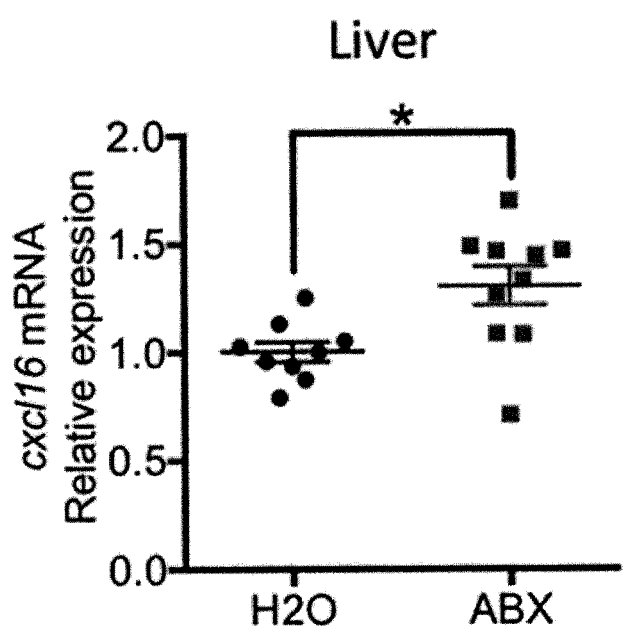
FIG. 27A is a dot plot showing CXCL16 mRNA expression levels in liver tissues from ABX or H$_2$O administered tumor-free C57BL/6 mice, in accordance with embodiments of the invention. n=9 for H$_2$O, 10 for ABX. p<0.05, Student's t-test.
Figure 27B:
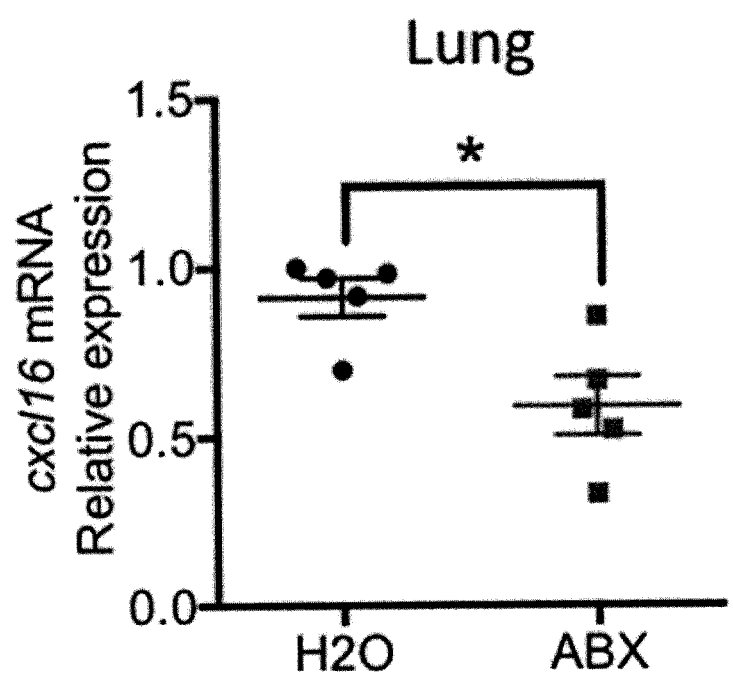
FIG. 27B is a dot plot showing real-time PCR analysis of CXCL16 mRNA levels in lung tissue from mice administered ABX or H$_2$O. n=5, p<0.05, Student's t-test.
Figure 27C:
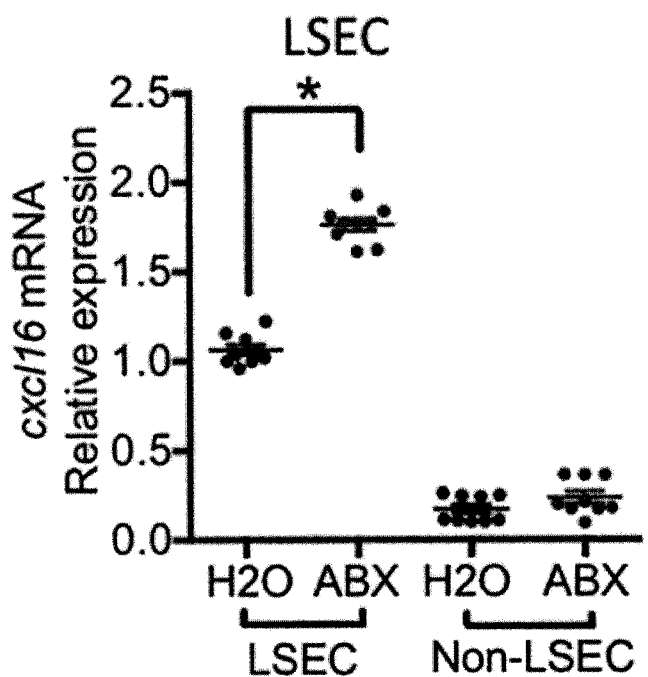
FIG. 27C is a dot plot showing CXCL16 mRNA levels measured by real time PCR in primary LSECs isolated from mice administered ABX or H$_2$O, in accordance with embodiments of the invention. n=9, p<0.05, two-way ANOVA.
Figure 27D:
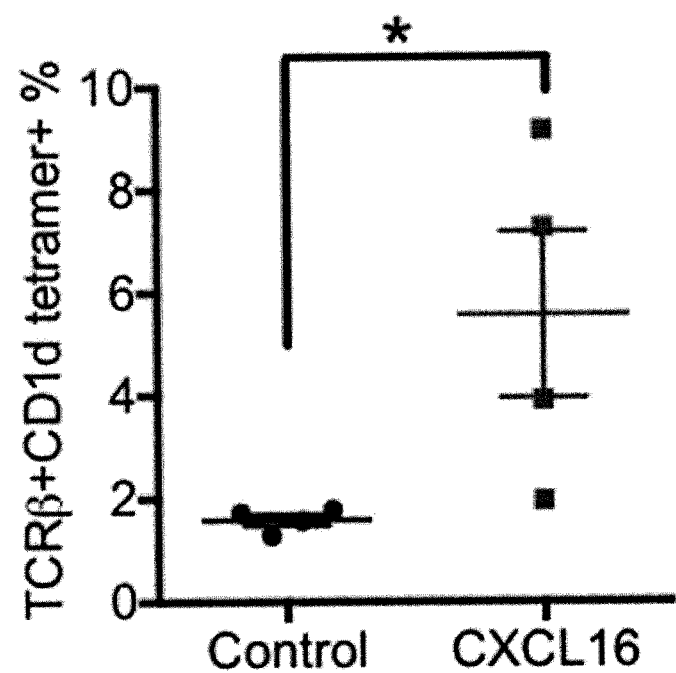
FIG. 27D is a dot plot showing hepatic NKT cell levels measured by flow cytometry of CXCL16-expressing plasmid delivered into mouse liver by hydrodynamic injection, in accordance with embodiments of the invention. n=4, p<0.05, Student's t-test.

Higher cxcl16 mRNA levels were found in the liver of ABX administered mice (FIG. 27A). This increase of cxcl16 mRNA was not detected in the lung (FIG. 27B). Liver sinusoidal endothelial cells (LSEC) have been reported to be the major source of CXCL16 production in liver. To identify the source of CXCL16, LSECs were isolated from ABX-administered mice. FIG. 27C shows that there was an almost two-fold increase of cxcl16 mRNA in LSECs from ABX-administered mice. Consistent with the previous report, LSECs have a much higher basal level of cxcl16 mRNA, and ABX administration did not affect cxcl16 mRNA expression in non-LSECs. The increase of CXCL16 protein in LSECs was confirmed by immunohistochemistry staining. In addition, enforced CXCL16 expression in the liver increased hepatic NKT levels (FIG. 27D). Together, these results suggest that ABX administration causes LSECs to produce more CXCL16 and recruits NKT cells to the liver.

Figure 28A:
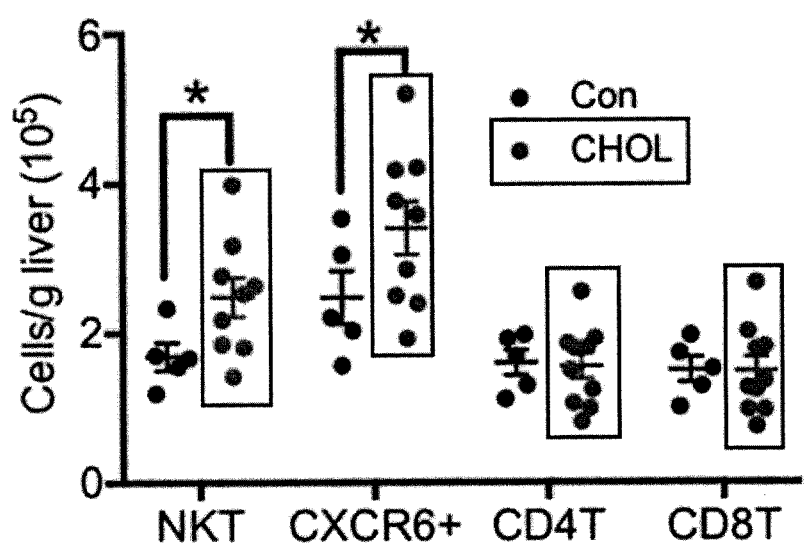
FIG. 28A is a dot plot showing hepatic NKT, CXCR6$^+$, CD4 T, and CD8 T cells measured from mice fed with a 2% cholestyramine (CHOL) or control diet (Con), in accordance with embodiments of the invention. n=5 for control, 9 for cholestyramine diet. p<0.05, two-way ANOVA.
Figure 28B:
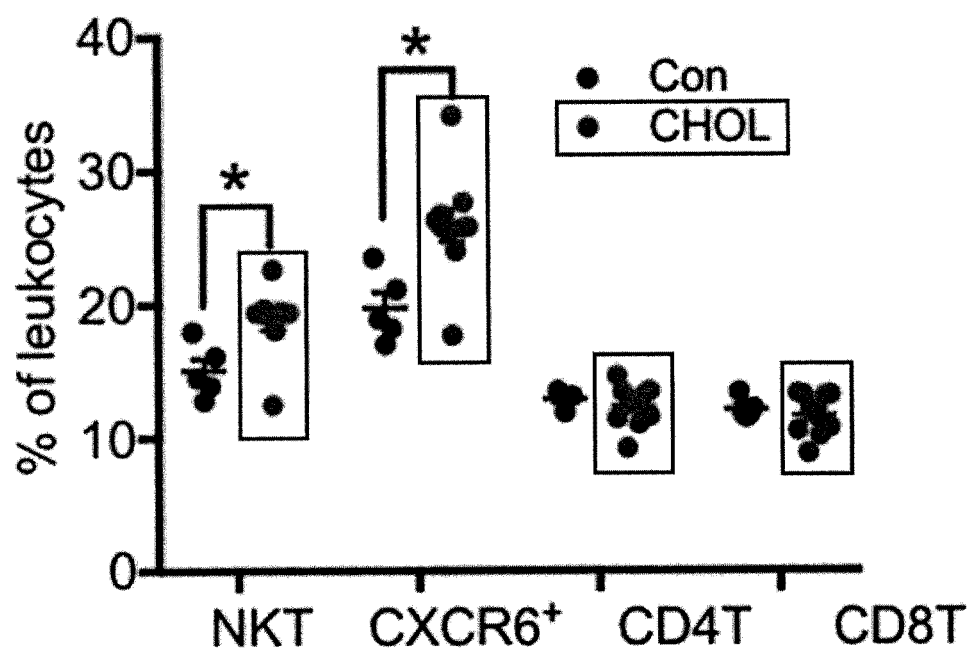
FIG. 28B is a dot plot showing frequencies of hepatic NKT, CXCR6$^+$, CD4 T and CD8 T cells determined from mice fed with 2% cholestyramine diet (CHOL) or a control diet (Con) as described in FIG. 28A, in accordance with embodiments of the invention. N=5 for control, n=10 for cholestyramine. p<0.05, two-way ANOVA.
Figure 28C:
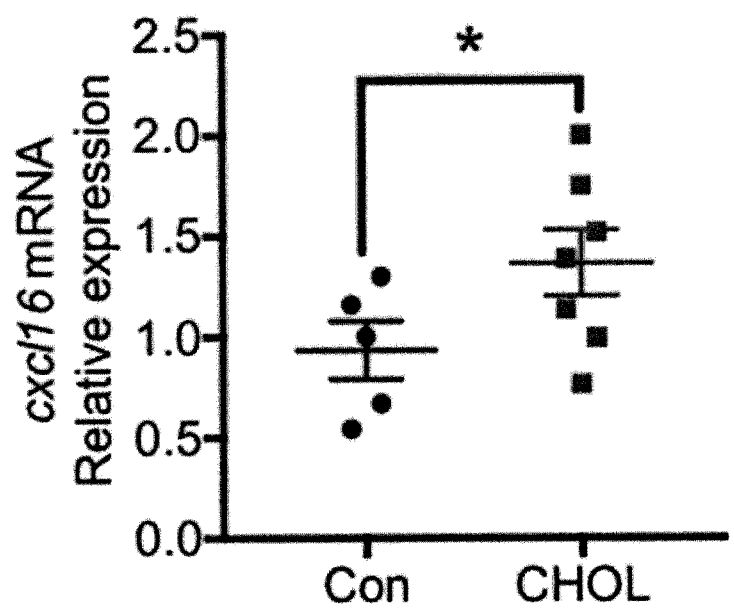
FIG. 28C is a dot plot showing liver tissue CXCL16 mRNA levels of the mice of FIG. 28B measured by real-time PCR, in accordance with embodiments of the invention. N=5 for control, n=10 for cholestyramine. p<0.05, Student's t-test.

Cholestyramine, a bile acid sequestrant, was used to block the enterohepatic circulation, thus reducing bile acid levels in the liver. Cholestyramine administration increased hepatic NKT and CXCR6$^+$ cells, but not CD4$^+$ T or CD8$^+$ T cells (FIGS. 28A and 28B). In parallel, cxcl16 mRNA was upregulated in the liver (FIG. 28C). This result suggests that bile acids are involved in the accumulation of NKT cells in the liver via CXCL16 regulation.

Figure 28D:
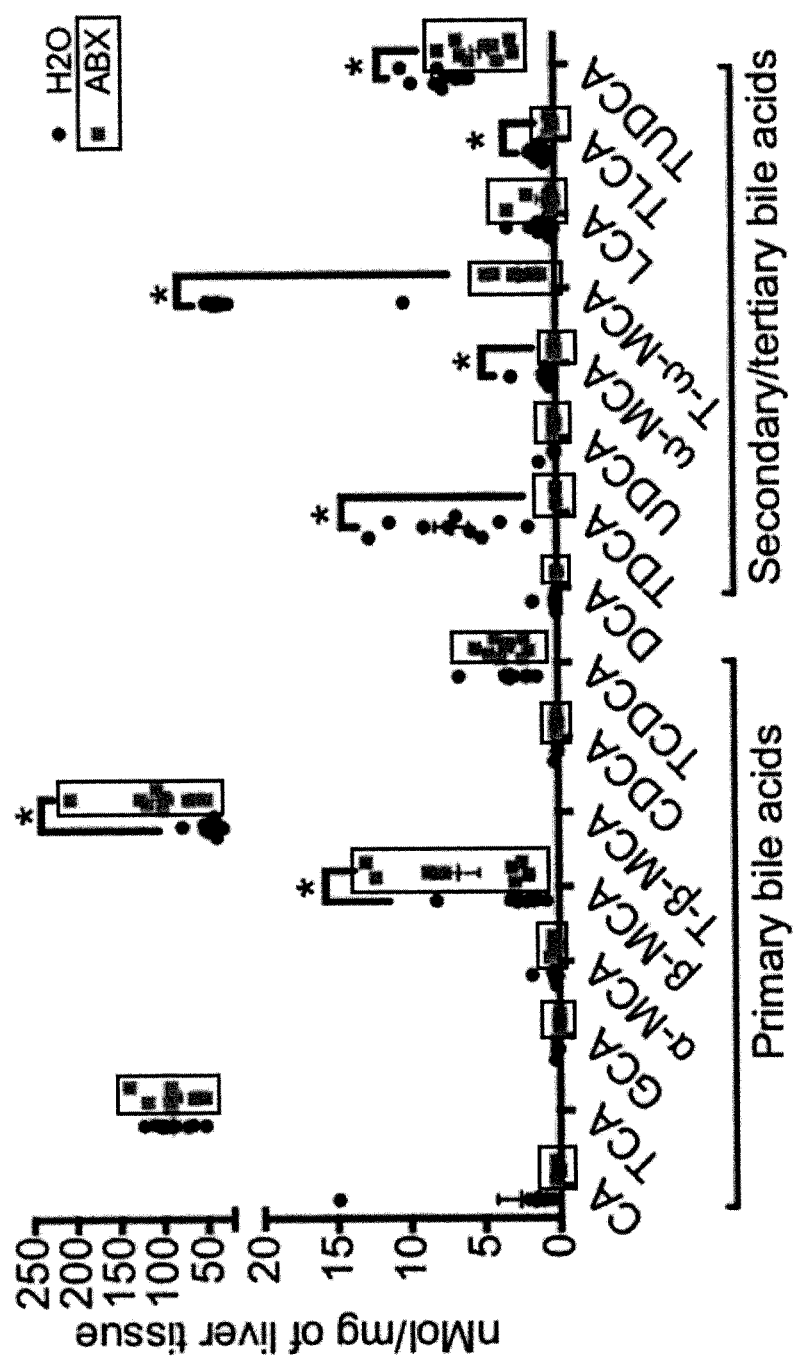
FIG. 28D is a dot plot showing liver bile acids profile of ABX or H$_2$O administered mice. n=9, p<0.05, Student's t-test.

To identify the bile acids involved in NKT cell regulation, the liver bile acid profile was determined. Control mouse liver contains the highest amount of primary bile acid taurocholic acid (TCA), followed by primary bile acid tauro-β-muricholic acid (T-β-MCA), and secondary bile acid tauro-ω-muricholic acid (T-ω-MCA) (FIG. 28D). ABX administration did not affect liver TCA but significantly increased primary bile acids T-β-MCA and β-MCA. Gut commensal bacteria convert primary bile acids into secondary bile acids. Secondary bile acids T-ω-MCA, taurodeoxycholic acid (TDCA), ω-MCA, taurolithocholic acid (TLCA), and tauroursodeoxycholic acid (TUDCA) were reduced in ABX administered mice (FIG. 28D).

Figure 28E:
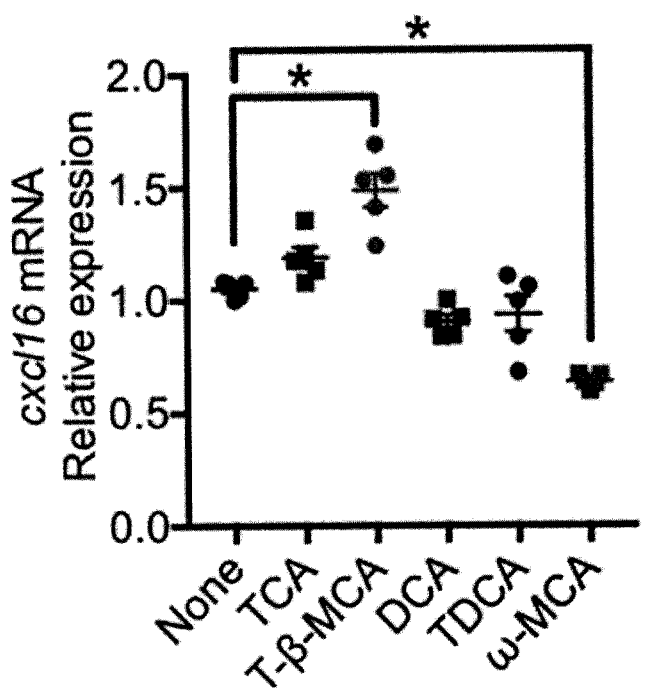
FIG. 28E is a dot plot showing CXCL16 mRNA levels of isolated LSECs administered different bile acids, in accordance with embodiments of the invention. n=5, p<0.05, one-way ANOVA.
Figure 28F:
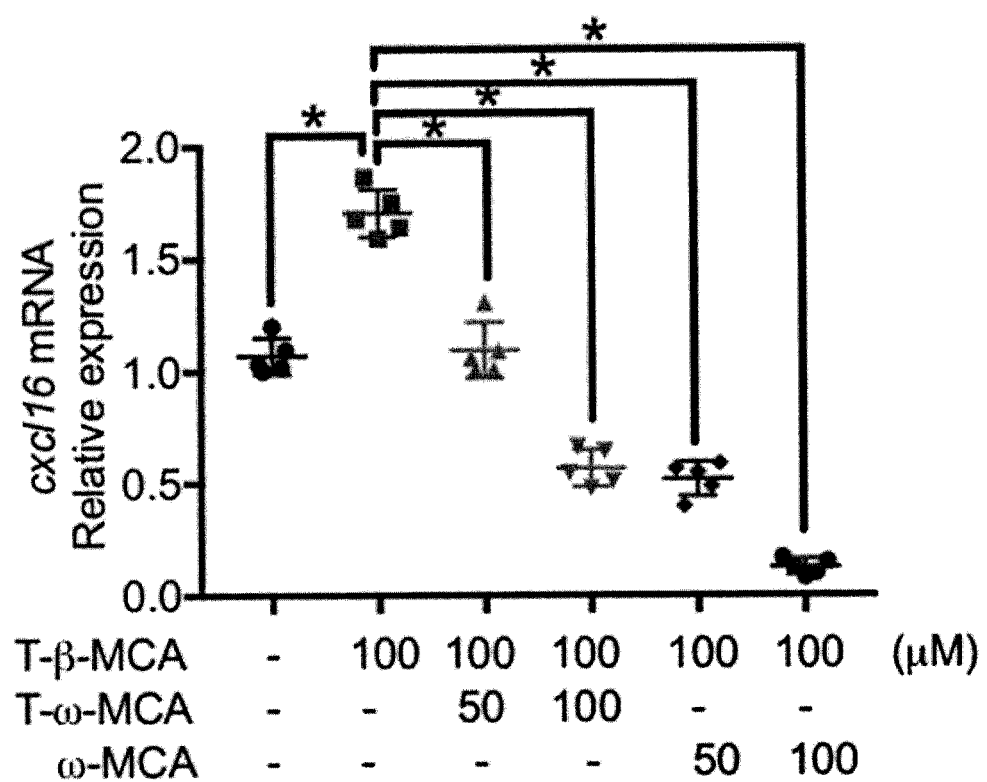
FIG. 28F is a dot plot showing CXCL16 mRNA levels of isolated LSECs administered a combination of T-b-MCA with T-w-MCA or ω-MCA. n=5, p<0.05, one-way ANOVA.

To connect these findings, the effect of bile acids on CXCL16 expression in primary murine LSECs in vitro was studied. FIG. 28E shows that the secondary bile acid ω-MCA decreased cxcl16 mRNA expression, while the primary bile acid T-β-MCA induced cxcl16 mRNA. Since cholestyramine administration reduces both primary and secondary bile acids, and caused NKT accumulation, the possibility that primary and secondary bile acids have opposing effects on CXCL16 regulation was tested. The secondary bile acid compromised the primary acid-induced cxcl16 mRNA upregulation, and even impaired cxcl16 mRNA expression below the unadministered baseline levels (FIG. 28F).

Figure 28G:
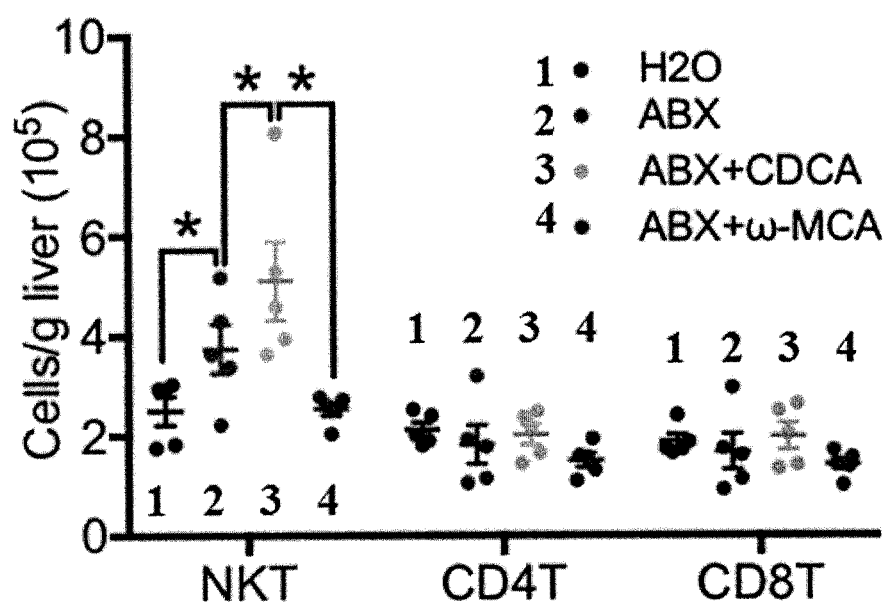
FIG. 28G is a dot plot showing hepatic NKT cell levels from 5 week old ABX-administered mice given three times oral gavage of CDCA or ω-MCA at the dose of 6 mg/15 g body weight at 48, 24, and 16 hours before measurements were taken at 6 weeks old. n=5, p<0.05, two-way ANOVA.

To confirm these in vitro findings, mice were fed with bile acids. ABX-administered mice were used to avoid the conversion of primary bile acids into secondary bile acids by commensal bacteria. FIG. 28G shows that feeding ω-MCA, a secondary bile acid, effectively reversed hepatic NKT accumulation, whereas feeding chenodeoxycholic acid (CDCA), a primary bile acid, enhanced NKT cell accumulation. This demonstrates that primary and secondary bile acids control hepatic NKT cell recruitment and have opposing effects.

Figure 28H:
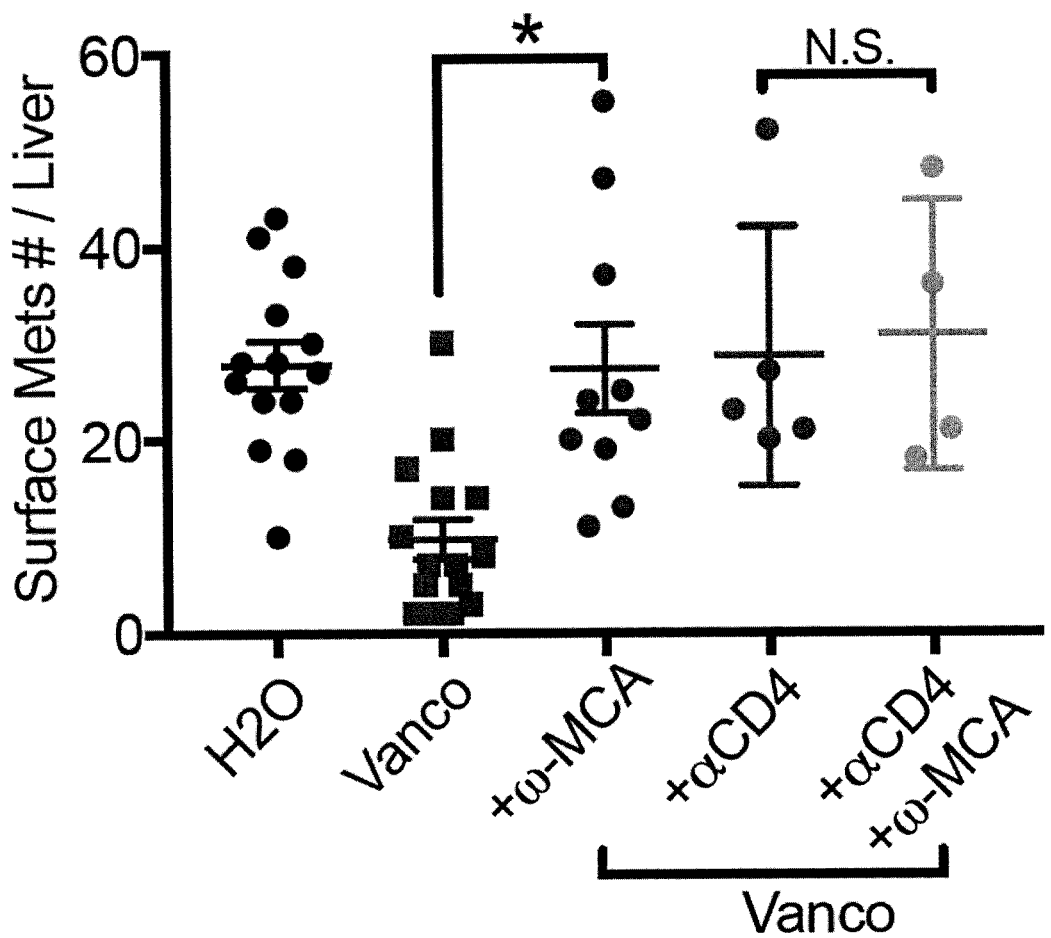
FIG. 28H is a dot plot showing A20 liver metastasis in vancomycin (Vanco) or H$_2$O-administered mice receiving ω-MCA feeding, high dose anti-CD4 depletion or the combination. n=15 for H$_2$O and vancomycin (Vanco), n=10 for +ω-MCA, n=5 for +αCD4, n=4 for +αCD4+ω-MCA, p<0.05, one-way ANOVA.
Figure 28I:
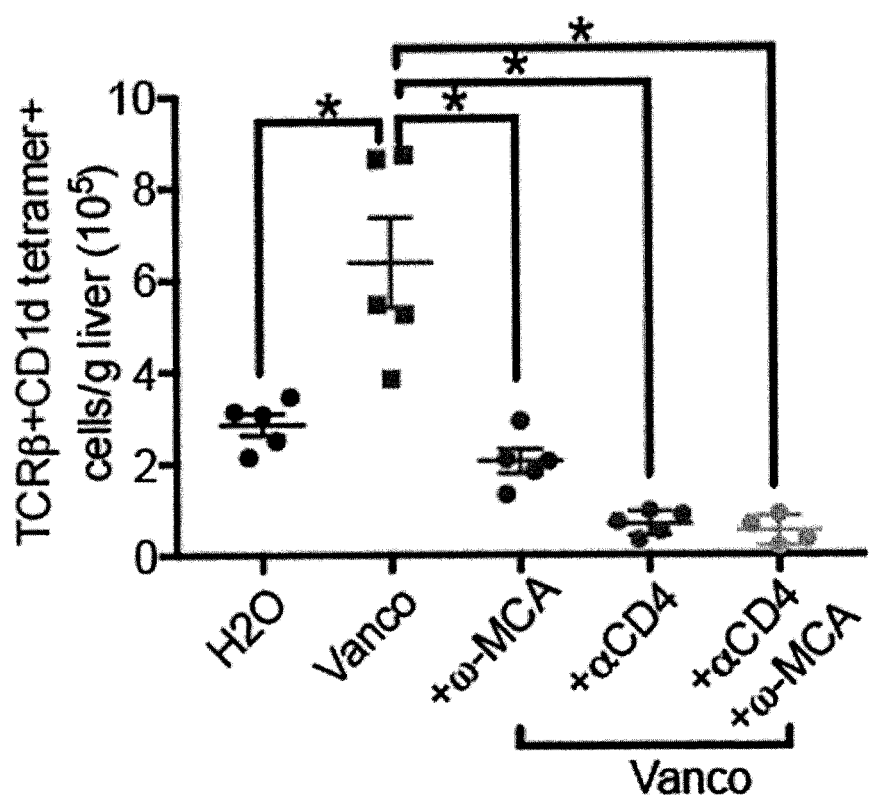
FIG. 28I is a dot plot showing hepatic NKT cells measured from A20 tumor-bearing mice fed with vancomycin (Vanco) or H$_2$O with the administration of ω-MCA, anti-CD4 depletion or the combination.
Figure 28J:
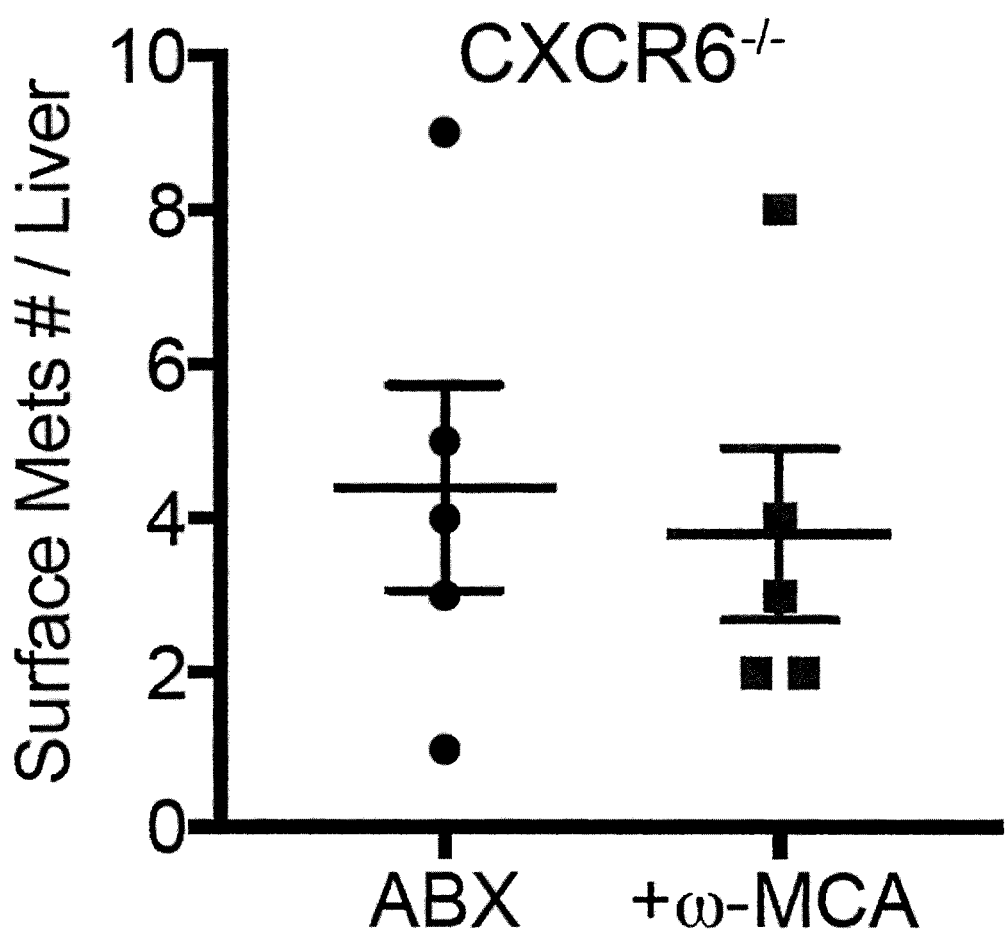
FIG. 28J is a dot plot showing EL4 liver metastasis in ABX-administered CXCR6$^{-/-}$ mice with or without ω-MCA feeding. n=5.

Next, ω-MCA was fed to liver tumor-bearing mice to test the effect of bile acids on liver tumor growth. ω-MCA feeding reversed the inhibition of liver tumor growth caused by antibiotic administration (FIG. 28H). NKT depletion eliminated the effect of ω-MCA on liver tumor growth (FIGS. 28H and 28I), suggesting that it is NKT cells mediated. Similarly, ω-MCA failed to affect liver tumor development in CXCR6$^{-/-}$ mice which have selective liver NKT cells lose (FIG. 28J).

Together, these results suggest that depleting commensal bacteria with antibiotics alters bile acids, preserving primary bile acids that induce CXCL16 expression and reducing secondary bile acids that inhibit, causing CXCL16 upregulation in LSECs, followed by NKT cell accumulation in the liver.

*Clostridium* Species Regulate Liver NKT Accumulation

Figure 29A:
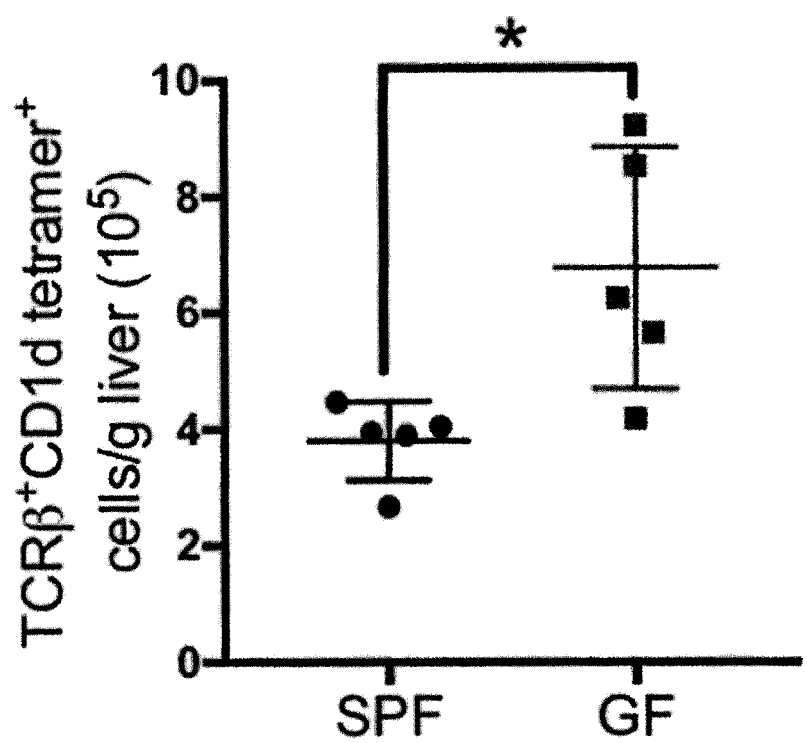
FIG. 29A is a dot plot showing hepatic NKT cell levels from germ-free mice or matched SPF mice with C57BL/6 background, in accordance with embodiments of the invention. n=5, p<0.05, Student's t-test.
Figure 29B:
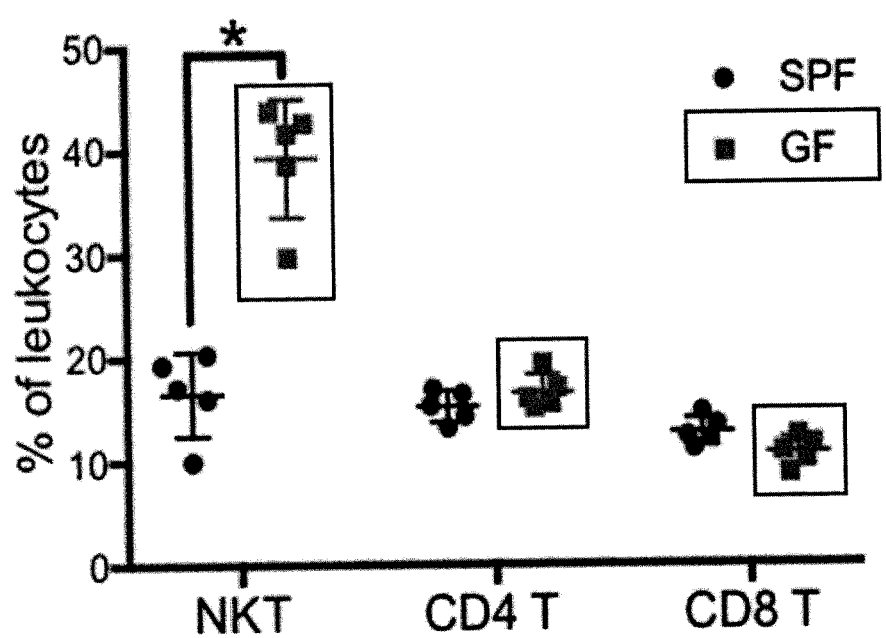
FIG. 29B is a dot plot showing frequencies of hepatic NKT cells measured in Germ-free mice or matched SPF mice with C57BL/6 background, in accordance with embodiments of the invention.
Figure 29C:
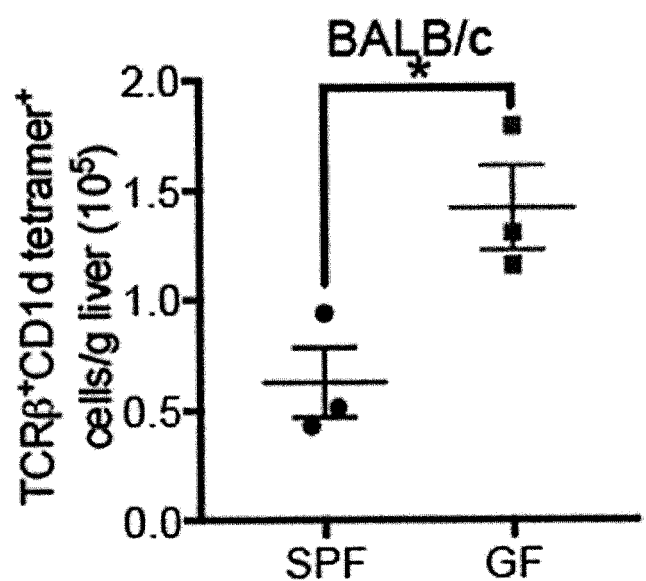
FIG. 29C is a dot plot showing absolute number of hepatic NKT cells measured in Germ-free mice or matched SPF mice with BALB/c background.
Figure 29D:
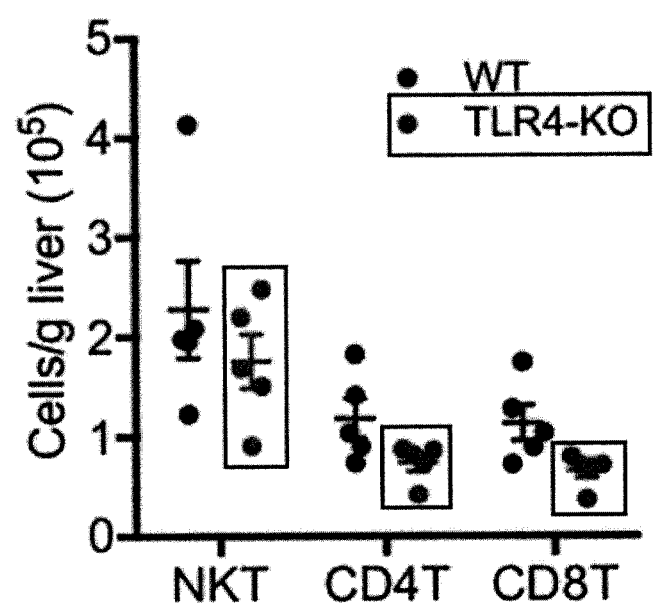
FIG. 29D is a dot plot showing hepatic NKT levels of TLR4 knockout mice or matched WT mice.
Figure 29E:
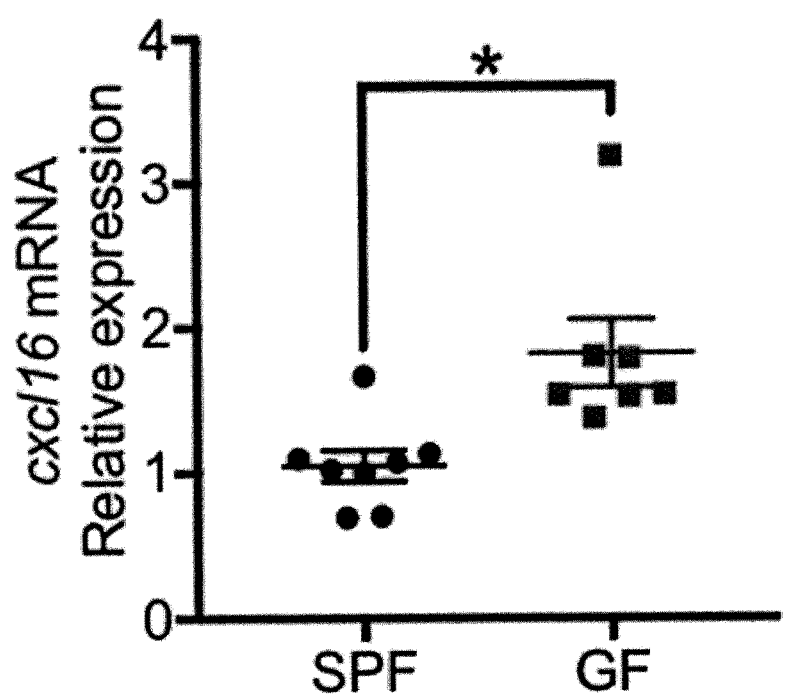
FIG. 29E is a dot plot showing cxcl16 mRNA expression in liver tissue from germ-free or SPF mice with C57BL/6 background, in accordance with embodiments of the invention. n=8 for SPF, 7 for GF, p<0.05, Student's t-test.

Although ABX administration caused more than a 1000-fold reduction of gut commensal bacteria load, it did not result in complete elimination of gut bacteria (FIG. 1). To rule out the possibility that the remaining bacteria mediate NKT accumulation, the experiment was repeated in germ-free mice. Again, more hepatic NKTs were found in germ-free mice when compared to the matched SPF control mice (FIG. 29A-29C), whereas no change was seen in TLR4 knockout mice (FIG. 29D). Similarly, cxcl16 mRNA levels were higher in the liver of germ-free mice (FIG. 29E).

Figure 29F:
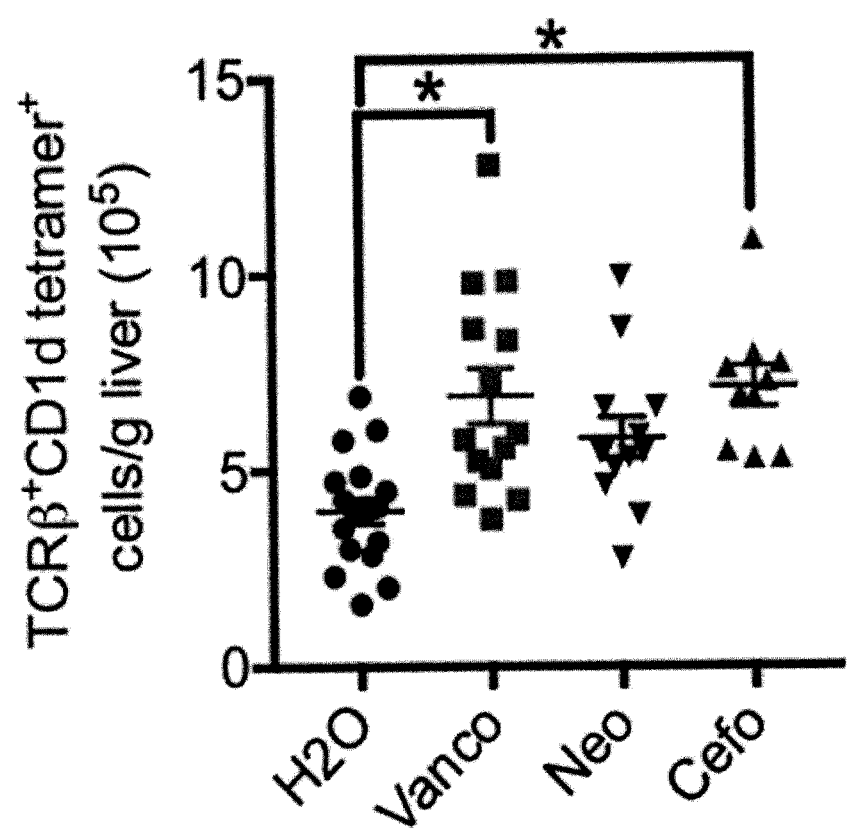
FIG. 29F is a dot plot showing hepatic NKT levels of naïve C57BL/6 mice fed with vancomycin (Vanco), neomycin (Neo) or cefoperazone (Cefo), in accordance with embodiments of the invention. Cumulative data are shown. n=18 for H$_2$O, 14 for vancomycin, 14 for neomycin, 10 for cefoperazone. p<0.05, one-way ANOVA.
Figure 29G:
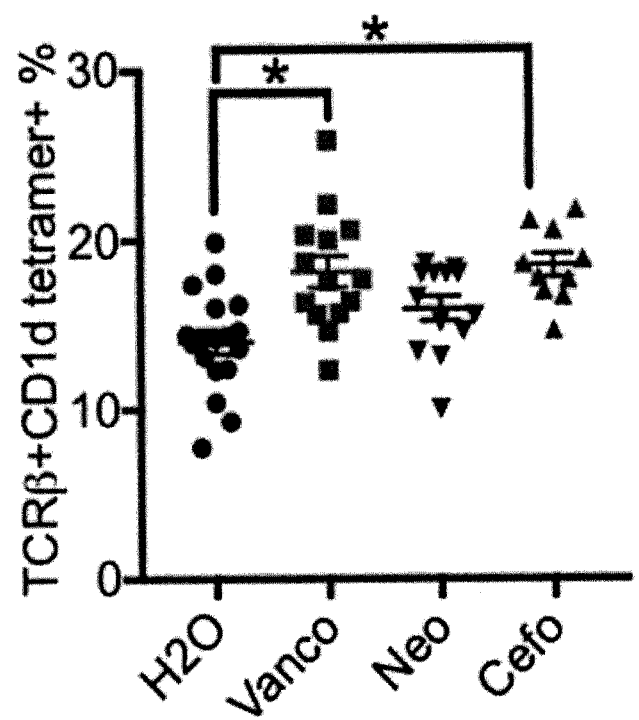
FIG. 29G is a dot plot showing frequencies of hepatic NKT cells of mice administered vancomycin, neomycin, cefoperazone or H$_2$O, in accordance with embodiments of the invention. n=18 for H$_2$O, 14 for vancomycin, 14 for neomycin, and 10 for cefoperazone.
Figure 29H:
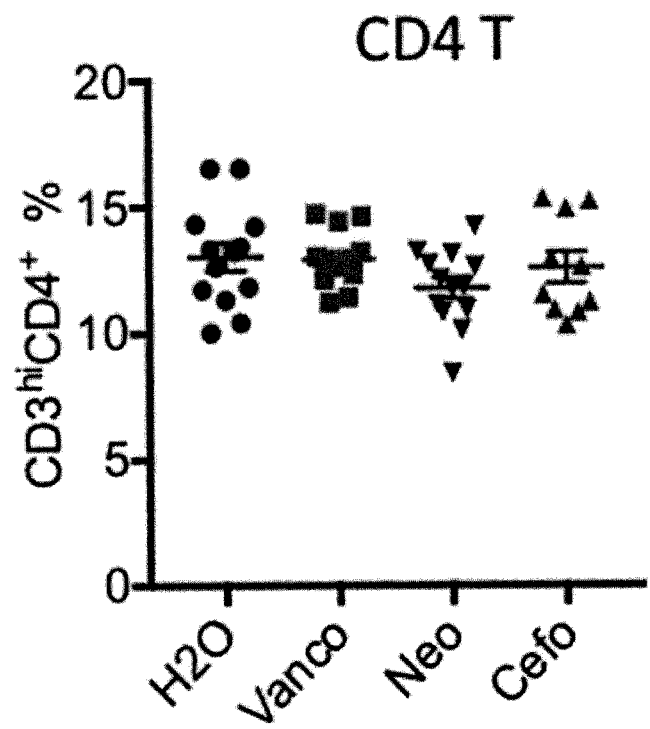
FIG. 29H is a dot plot showing frequencies of hepatic CD4 T cells of mice administered vancomycin, neomycin, cefoperazone or H$_2$O. n=18 for H$_2$O, 14 for vancomycin, 14 for neomycin, and 10 for cefoperazone.
Figure 29I:
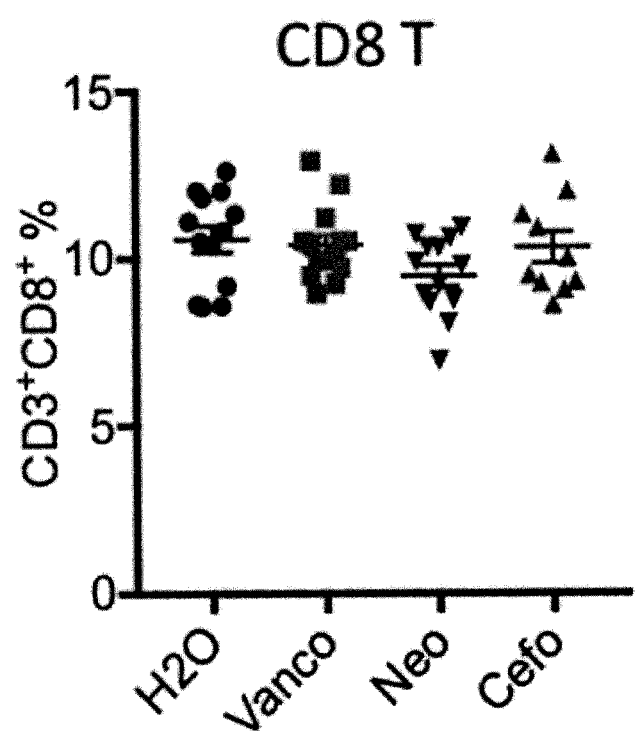
FIG. 29I is a dot plot showing frequencies of hepatic CD8 T cells of mice administered vancomycin, neomycin, cefoperazone or H$_2$O. n=18 for H$_2$O, 14 for vancomycin, 14 for neomycin, and 10 for cefoperazone.

Next, identification of the commensal bacteria responsible for the observed phenotype was attempted. The ABX antibiotic cocktail used here contains three antibiotics with different activity spectrums. Therefore, individual antibiotic administration was performed to narrow down the targeting bacteria. FIGS. 29F and 29G show that vancomycin alone was sufficient to increase hepatic NKT cells, while neomycin had little effect. An increase of liver NKT cells was also be observed in mice fed with cefoperazone. No significant changes of hepatic CD4$^+$ or CD8 T$^+$ cells were observed (FIGS. 29H and 29I). Both vancomycin and cefoperazone target gram-positive bacteria. Vancomycin and cefoperazone have been reported to deplete secondary bile acids and increase primary bile acids in the gut, which is consistent with the finding that bile acids also change in the liver and regulate NKT cell accumulation.

Secondary Bile Acid Reversed the Inhibition of Live Tumor Growth

Figure 30A:
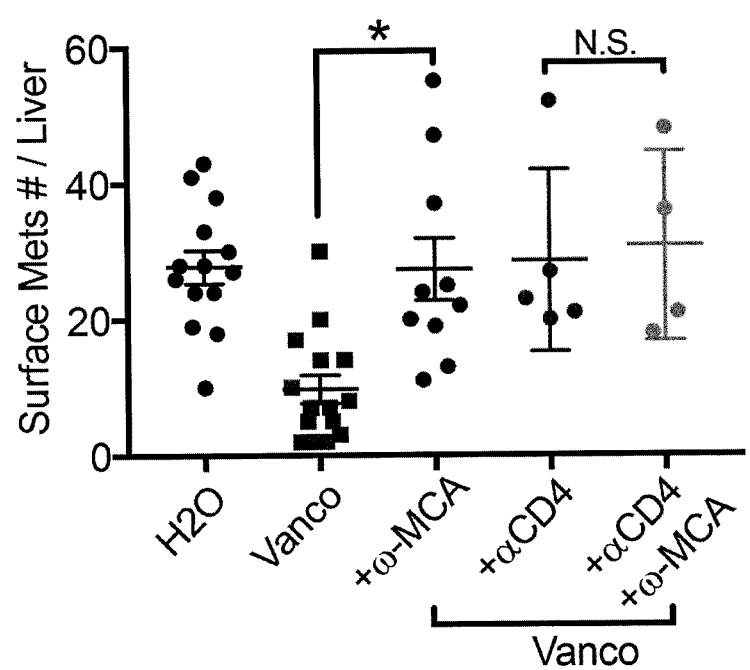
FIG. 30A is a dot plot showing liver surface tumor nodule counts. n=15 for H$_2$O and Vanco, n=10 for +ω-MCA, n=5 for +aCD4, n=4 for +aCD4+ω-MCA, p<0.05, one-way ANOVA.
Figure 30B:
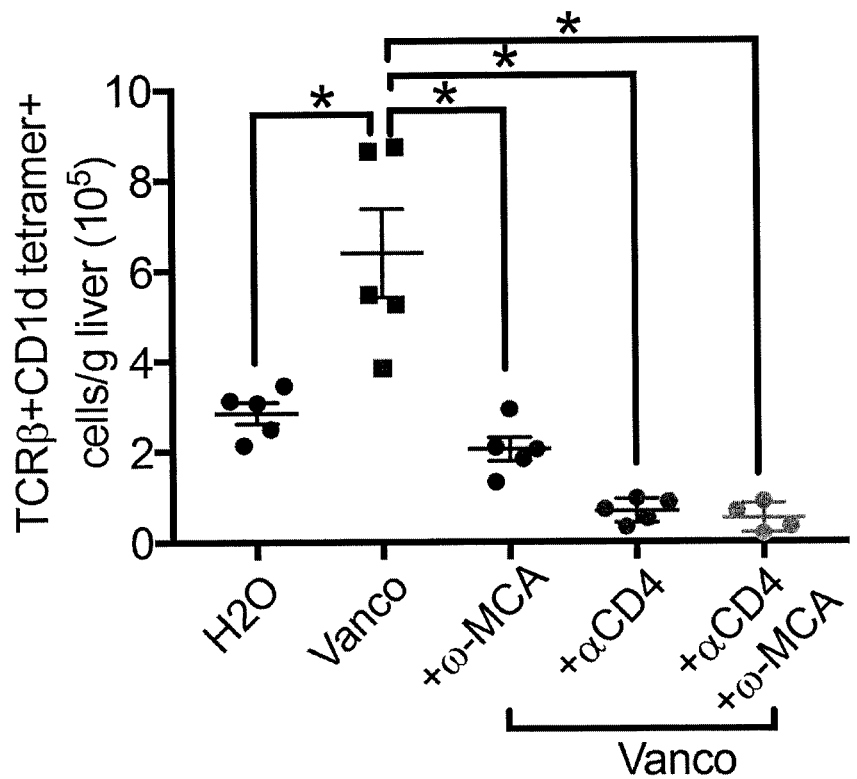
FIG. 30B is a dot plot showing hepatic NKT cell levels measured by flow cytometry. n=15 for H$_2$O and Vanco, n=10 for +ω-MCA, n=5 for +aCD4, n=4 for +aCD4+ω-MCA, p<0.05, one-way ANOVA.

A20 tumor cells were i.v. injected into vancomycin- (Vanco) or $H_2O$-administered BALB/c mice. ω-MCA (5 mg/mouse) was given by oral gavage three times/week. aCD4 antibody (GK1.5) was given i.p. at the dose of 500 μg/mouse weekly to deplete MKT cells. FIGS. 30A and 30B show the results after 3 weeks.

Figure 30C:
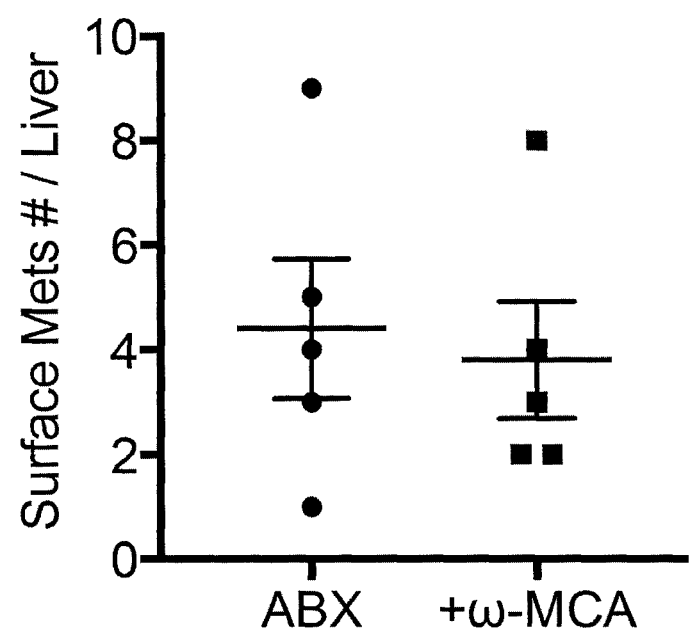
FIG. 30C is a dot plot showing liver surface tumor nodule counts.

EL4 tumor cells were injected into ABX-pre-administered $CXCR6^{-/-}$ mice. ω-MCA was given as described above. Liver surface tumors were counted three weeks after tumor injection. FIG. 30C shows the results.

Figure 31:
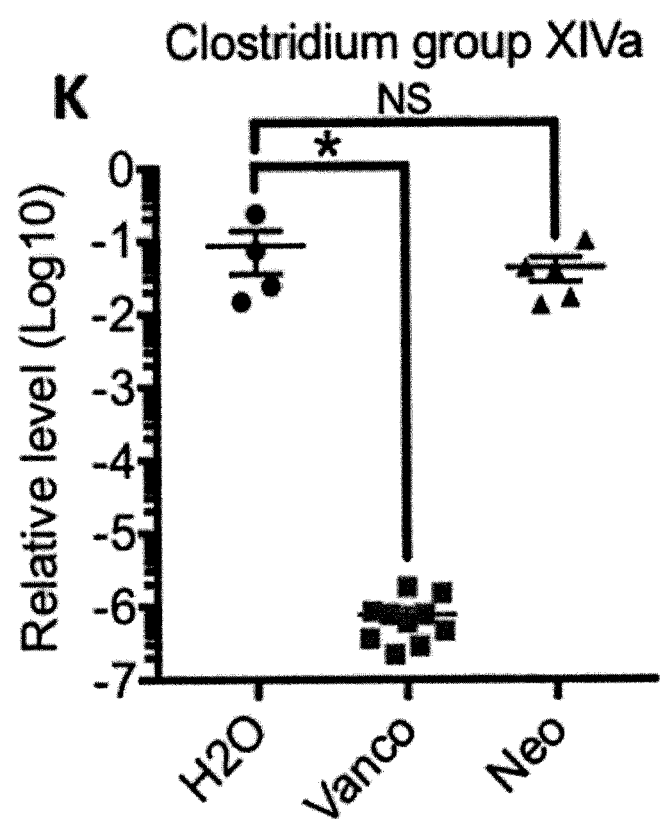
FIG. 31 is a dot plot showing the stool levels of *Clostridum* Cluster XIVa from single antibiotic administration measured by real-time PCR. Mice were administered vancomycin, neomycin, cefoparazone or H$_2$O. n=4 for H$_2$O, 10 for vancomycin, 5 for neomycin, p<0.05, one-way ANOVA.

The 7α-dehydroxylation reaction is the most quantitatively important process performed by the gut bacteria in the production of secondary bile acids. This multistep biochemical process is restricted to a narrow phylogenetic group of gram-positive bacterial species belonging to the *Clostridium* cluster XIV. In line with these findings, it was observed that vancomycin, which increased liver NKT cells, depleted *Clostridium*; but neomycin, which had little effect on liver NKT, could not remove *Clostridium* (FIG. 31).

Figure 32:
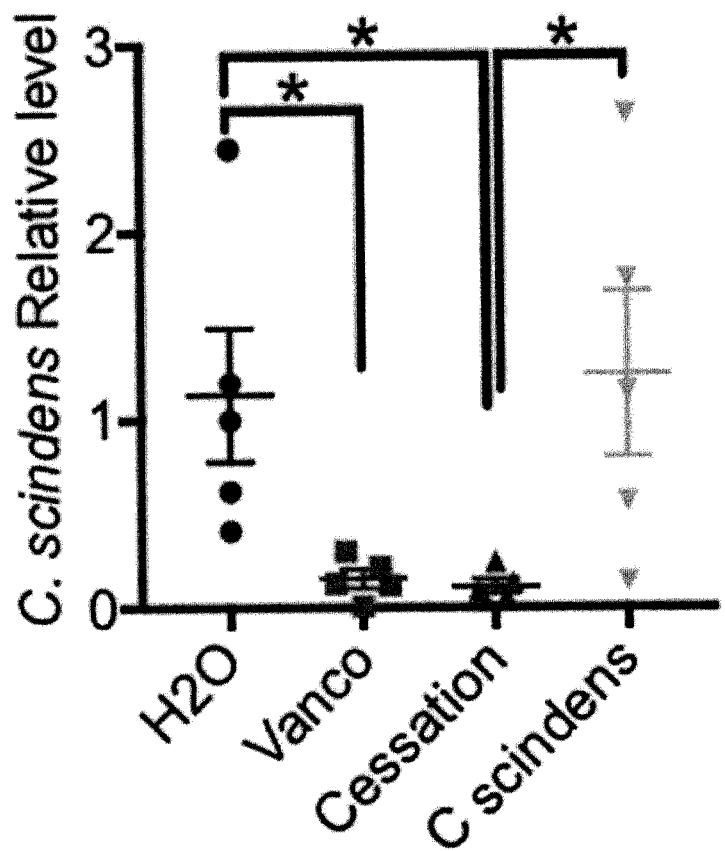
FIG. 32 is a dot plot showing colonization testing by real-time PCR with *Clostridium scindens* (*C. scindens*)-specific primers. Five week old mice were administered vancomycin for one week. Then vancomycin was stopped, and mice were given oral gavage of *C. scindens* or vehicle (cessation). Measurements were taken twenty-four hours after gavage.
Figure 33A:
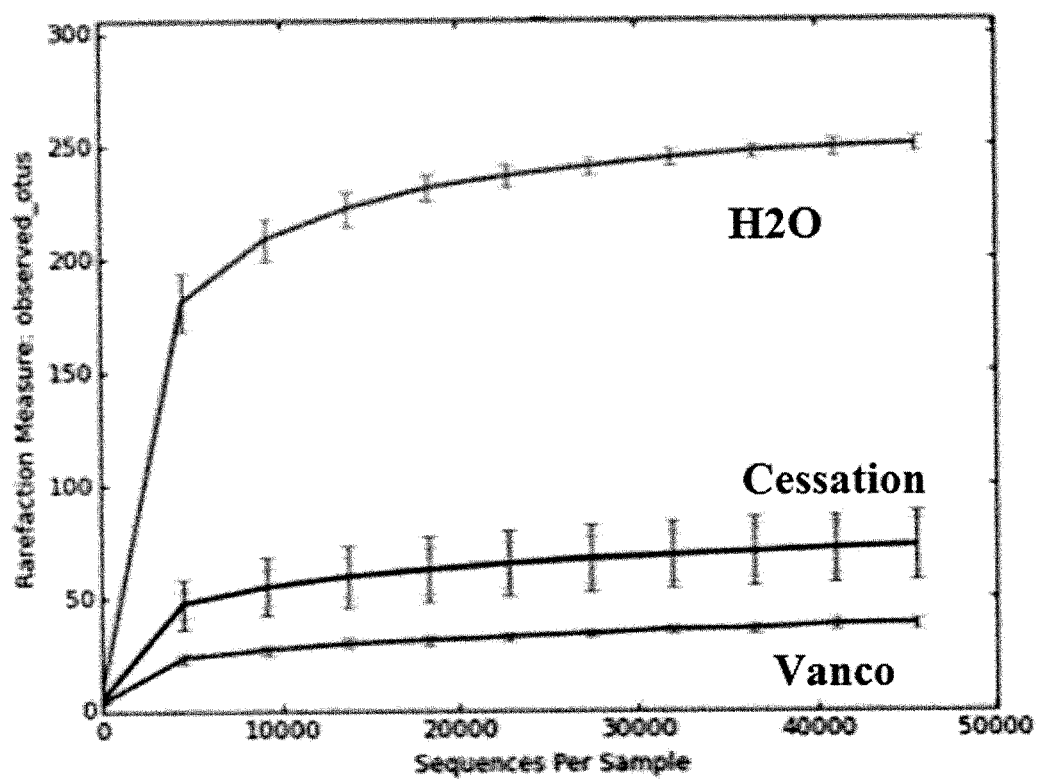
FIG. 33A is a line graph showing stool bacteria analysis performed by 16S rRNA sequencing, in accordance with embodiments of the invention. Five week old mice were administered vancomycin for one week. Then vancomycin was stopped, and mice were given oral gavage of *C. scindens* or vehicle (cessation). Measurements were taken twenty-four hours after gavage. Alpha diversity is shown.
Figure 33B:
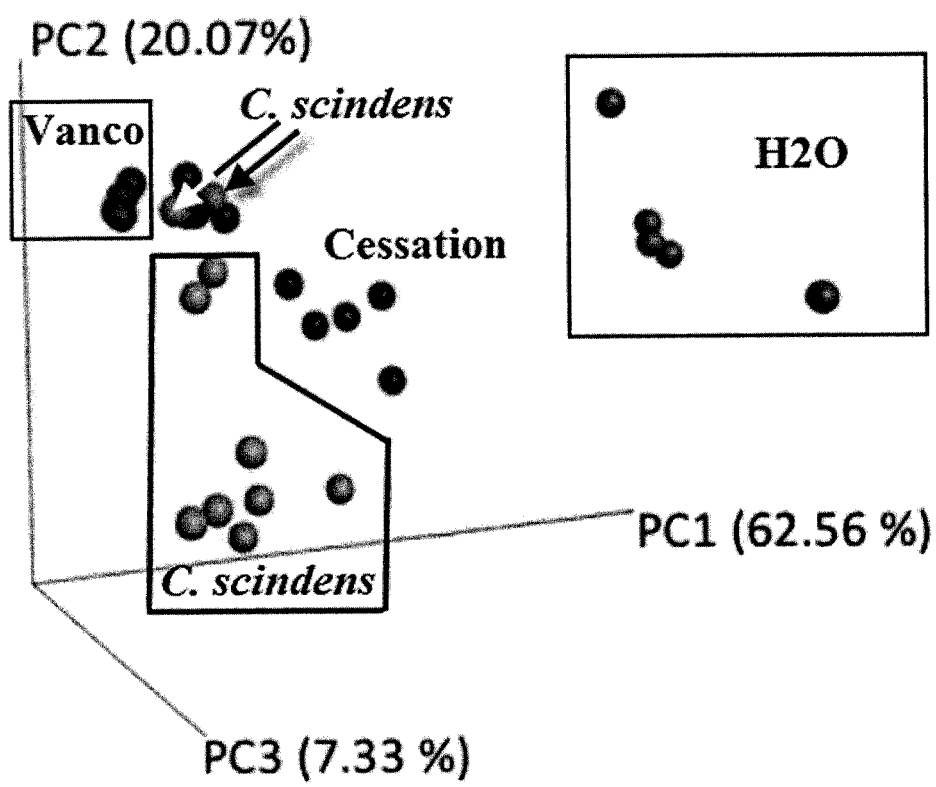
FIG. 33B is a dot plot showing stool bacteria analysis performed by 16S rRNA sequencing, in accordance with embodiments of the invention. Five week old mice were administered vancomycin for one week. Then vancomycin was stopped, and mice were given oral gavage of *C. scindens* or vehicle (cessation). Measurements were taken twenty-four hours after gavage. Beta diversity is shown.

Next, the possible role of *Clostridium* species on liver NKT cell accumulation was tested in a colonization experiment. *Clostridium scindens* was chosen because it is commonly found in both mice and human and has a conserved bai ("bile acid inducible") gene operon for the 7α-dehydroxylation reaction. Mice were fed with vancomycin for one week to induce hepatic NKT cells, then vancomycin was stopped, and the mice were given *C. scindens* or vehicle. The successful colonization with *Clostridium scindens* was confirmed (FIG. 32). One day after oral gavage, fecal bacterial were analyzed by 16S rRNA sequencing (FIGS. 33A and 33B, Table 1).

TABLE 1

| | Vanco (%) | Cessation (%) | C. scindens (%) | $H_2O$ (%) |
|---|---|---|---|---|
| Verrucomicrobiales | 34.3 | 30.9 | 34.4 | 0.0 |
| Enterobacteriales | 10.7 | 4.6 | 10.4 | 0.1 |
| Burkholderiales | 4.4 | 2.6 | 2.9 | 0.4 |
| Clostridiales | 3.9 | 5.6 | 12.8 | 28.9 |
| Lactobacillales | 43.7 | 40.3 | 17.1 | 32.1 |
| Bacteroidales | 0.0 | 15.1 | 19.9 | 35.3 |

Continuous vancomycin administration caused a reduction of Clostridiales and Bacteroidales but an expansion of Verrucomicrobiales compared to $H_2O$ group. An early recovery of Bacteroidales was observed after vancomycin cessation.

Figure 33C:
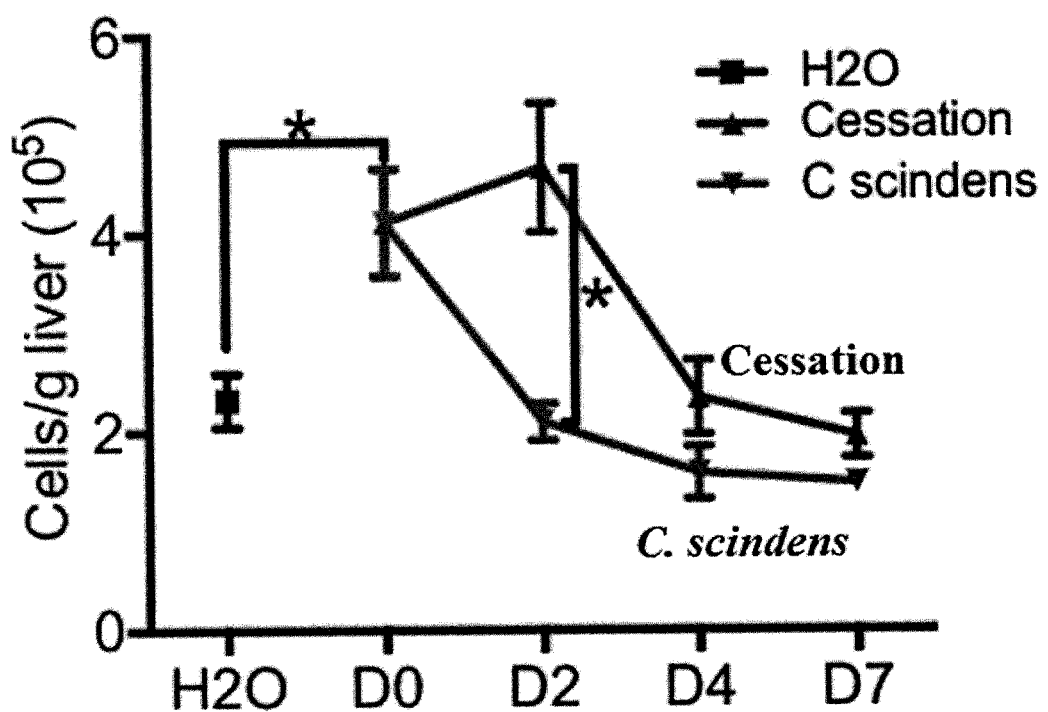
FIG. 33C is a line graph showing a time course study of hepatic NKT levels, in accordance with embodiments of the invention. Mice were administered vancomycin for one week. Then vancomycin was stopped and mice were given oral gavage of *C. scindens* or cessation. Cumulative data are shown. n=10 for H$_2$O, D0, *C. scindens* D4 and Cessation D4; 5 for *C. scindens* D2, Cessation D2, *C. scindens* D7 and Cessation D7. p<0.05, two-way ANOVA.
Figure 33D:
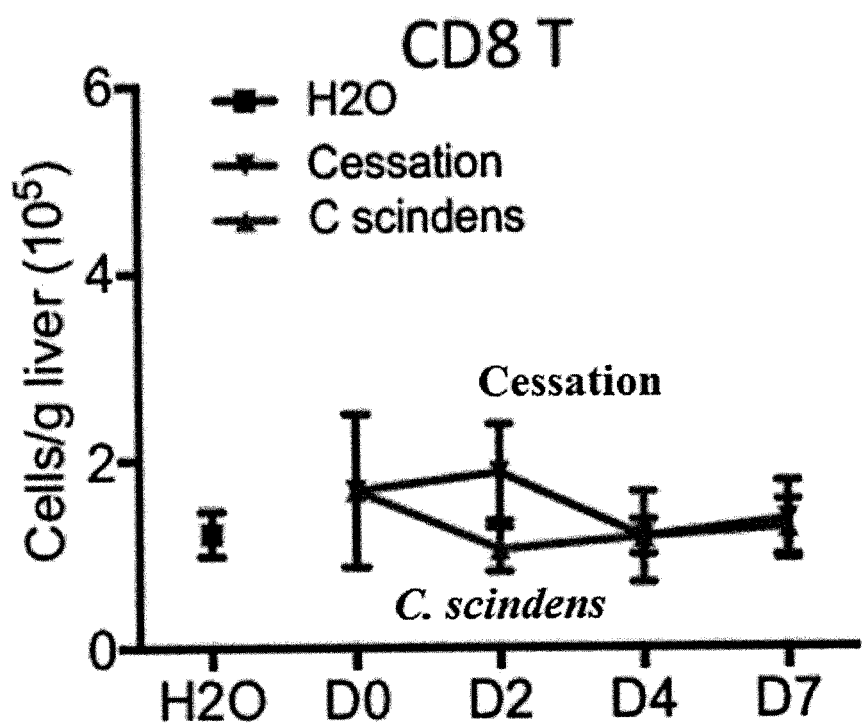
FIG. 33D is a line graph showing a time course study of hepatic CD8$^+$ T cell levels. Five week old mice were administered vancomycin for one week. Then vancomycin was stopped, and mice were given oral gavage of *C. scindens* or vehicle (cessation). n=10 for H$_2$O, D0, *C. scindens* D4 and Cessation D4; 5 for *C. scindens* D2, Cessation D2, *C. scindens* D7 and Cessation D7.
Figure 33E:
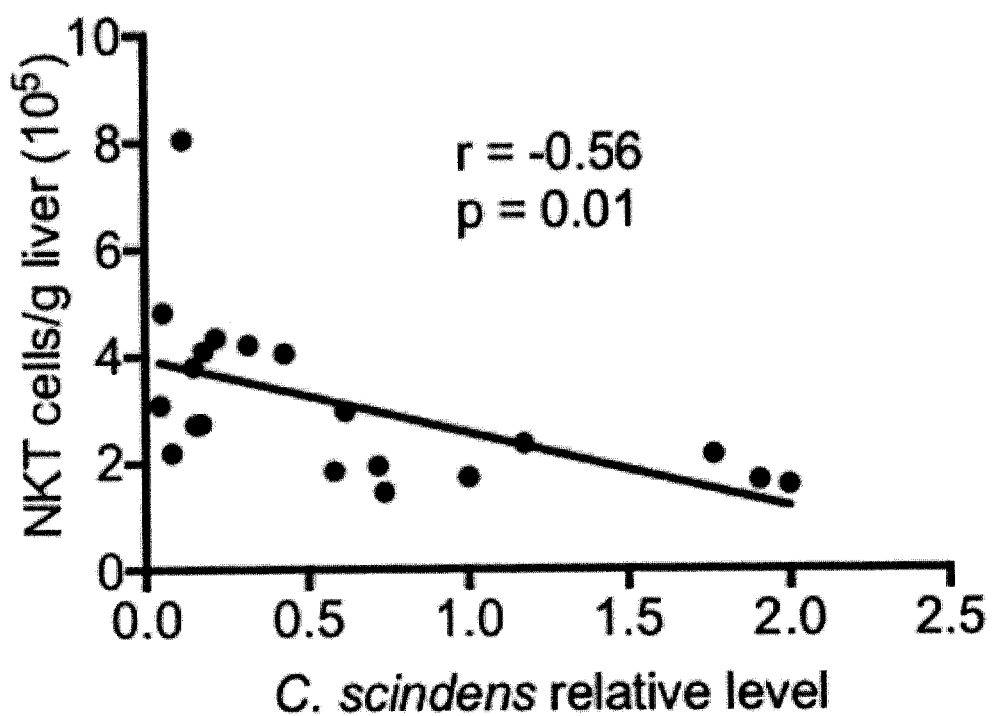
FIG. 33E is dot plot showing the correlation between hepatic NKT cells and *C. scindens* levels, in accordance with embodiments of the invention. Five week old mice were administered vancomycin for one week. Then vancomycin was stopped, and mice were given oral gavage of *C. scindens* or vehicle (cessation). Measurements were taken two days after gavage.

Gavage of *Clostridium scindens* increased Clostridiales population. A time course study shows that hepatic NKT levels started to drop between day 2 and day 4 after vancomycin withdrawal (FIG. 33C), suggesting the recovering of gut commensal bacteria. Colonization of *C. scindens* induced a quick and dramatic reduction of hepatic NKT cells (FIG. 33C) but did not affect other immune cells (FIG. 33D). An inverse correlation between the frequency of hepatic NKT cells and *C. scindens* levels was seen (FIG. 33E). Thus, the results suggest that *Clostridium* species such as *C. scindens* are involved in the regulation of hepatic NKT cell accumulation.

Bile Acids Control Liver CXCL16 Expression in Humans

Figure 34A:
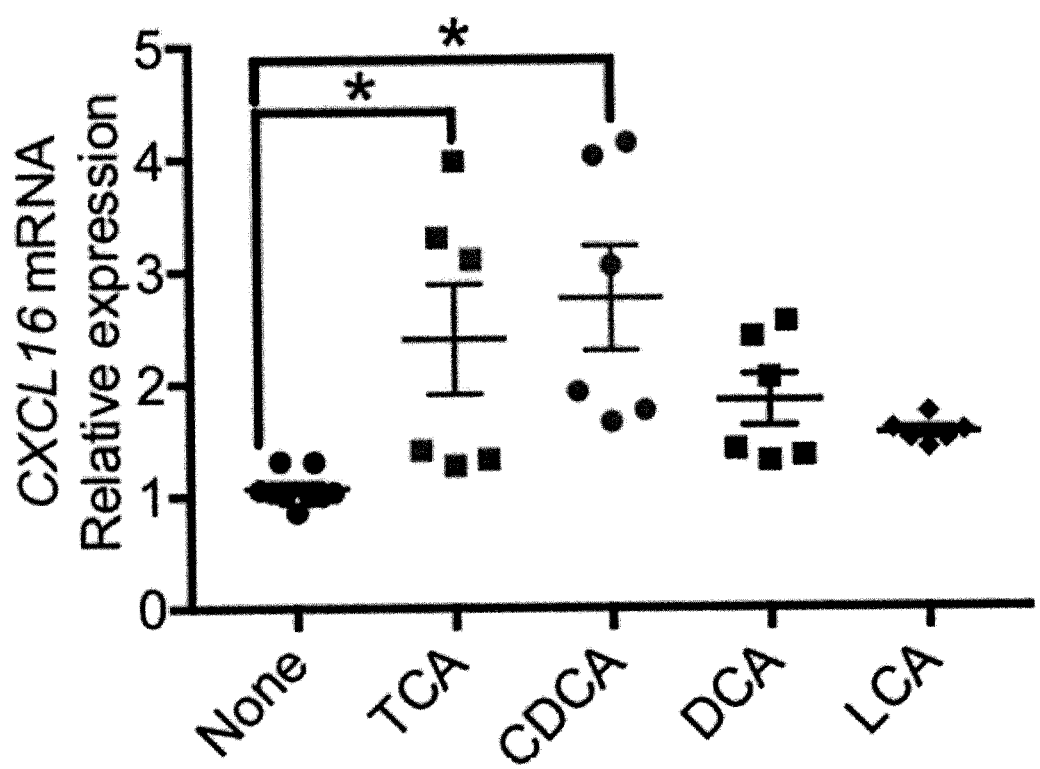
FIG. 34A is a dot plot showing CXCL16 mRNA levels measured by real-time PCR in SK-HEP1 cells administered different bile acids, in accordance with embodiments of the invention. n=6, p<0.05, one-way ANOVA.
Figure 34B:
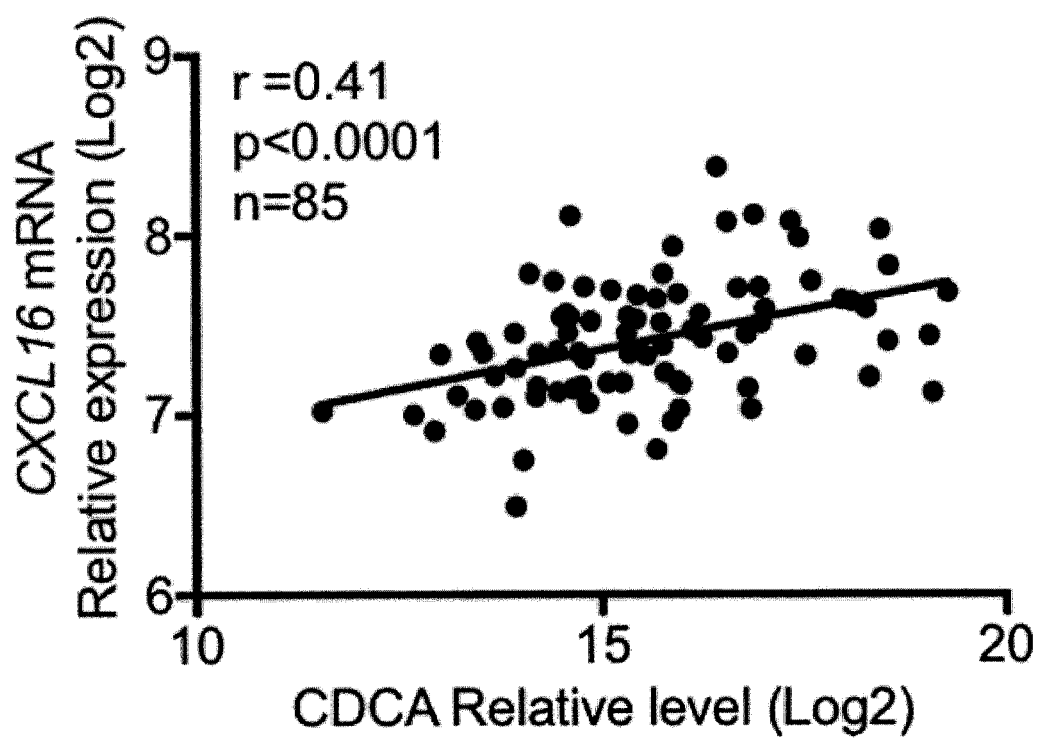
FIG. 34B is a dot plot showing the correlation between primary bile acid CDCA and CXCL16 mRNA expression in non-tumor liver tissues from HCC or CCA patients of the TIGER cohort, in accordance with embodiments of the invention. Pearson correlation coefficient test was performed.
Figure 34C:
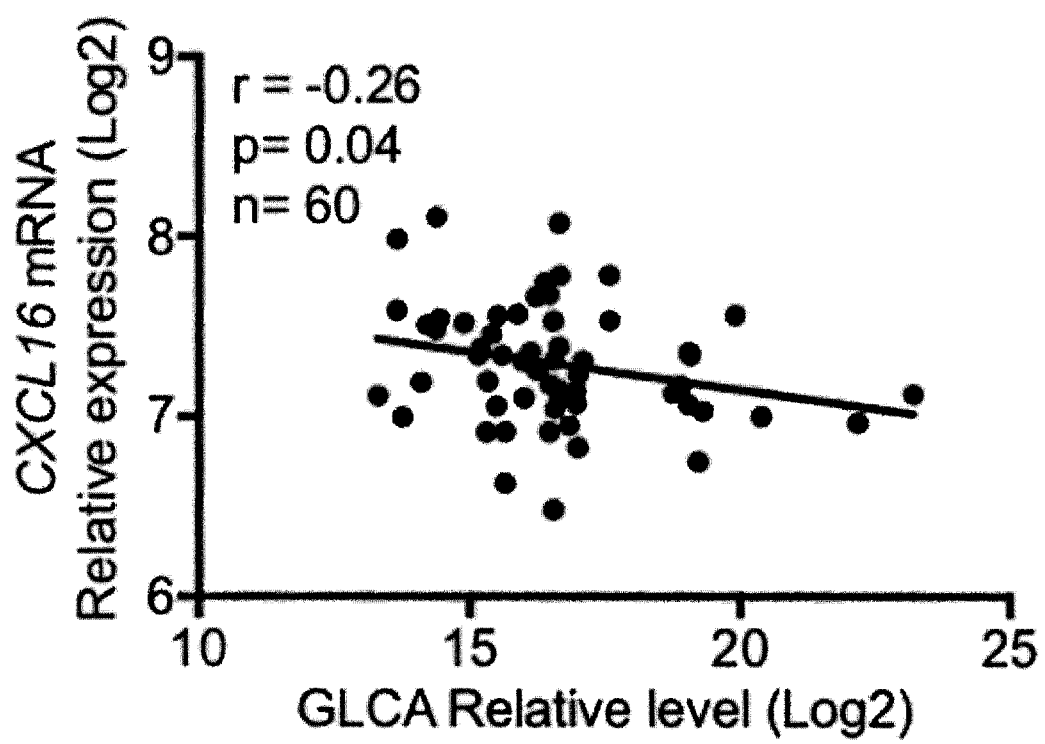
FIG. 34C is a dot plot showing the correlation between bile acid GLCA and CXCL16 expression in non-tumor liver tissues from patients of TIGER cohort. Pearson correlation coefficient test was used.
Figure 34D:
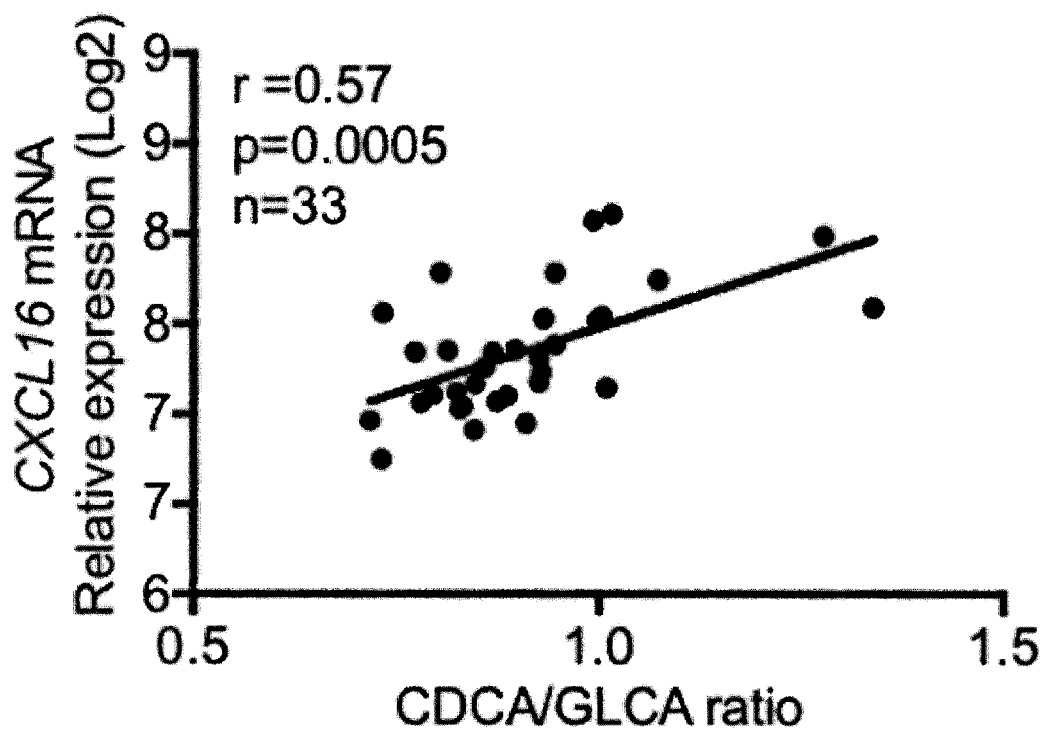
FIG. 34D is a dot plot showing the correlation between bile acid ratio (CDCA/GLCA) and CXCL16 expression in non-tumor liver tissues from patients of TIGER cohort, in accordance with embodiments of the invention. Pearson correlation coefficient test was used.

The effect of bile acids on human LSEC CXCL16 mRNA expression was tested. SK-HEP1 cells were administered different bile acids. Primary bile acids CDCA and TCA induced CXCL16 mRNA expression (FIG. 34A). Next, the correlation between bile acids and CXCL16 expression was tested in non-tumor liver tissues from HCC or cholangiocarcinoma patients of the TIGER cohort. Primary bile acid CDCA levels correlated with CXCL16 expression (FIG. 34B), and the opposite was found with the secondary bile acid glycolithocholate (GLCA) (FIG. 34C). The primary/secondary ratio was associated with CXCL16 increase (FIG. 34D), indicating that the opposing effect of bile acids on CXCL16 expression also exists in humans.

In humans, mucosal-associated invariant T (MAIT) cells are enriched in the liver and comprise 20-50% of hepatic lymphocytes. CXCR6 is expressed on MAIT cells. Thus, liver MAIT cells may also be controlled by gut bacteria via CXCL16 regulation. MAIT cells recognize bacterial derivatives, and are involved in inflammatory liver diseases such as non-alcoholic steatohepatitis (NASH).

Besides anti-tumor function, NKT cells have been suggested as important regulators of autoimmune responses. The results here indicate that gut commensal bacteria and bile acids could be potential targets for controlling liver autoimmune diseases.

Example 2

This example demonstrates tadalafil suppresses tumor growth, reduces tumor MDSC number, and modulates tumor microenvironment.

Figure 35A:
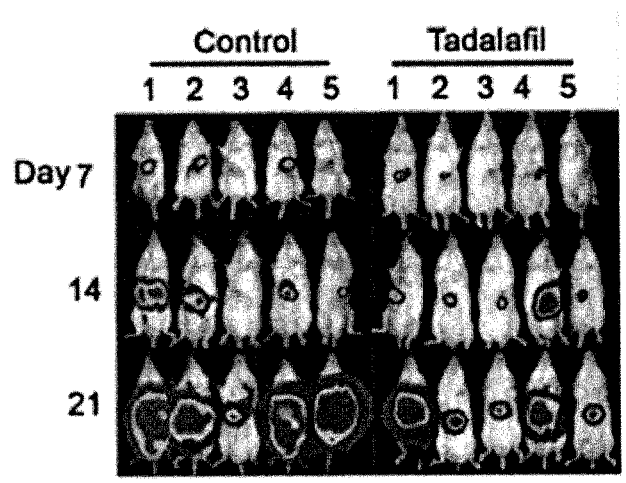
FIG. 35A is as image showing hepatoma cells implanted into the livers of male mice.
Figure 35B:
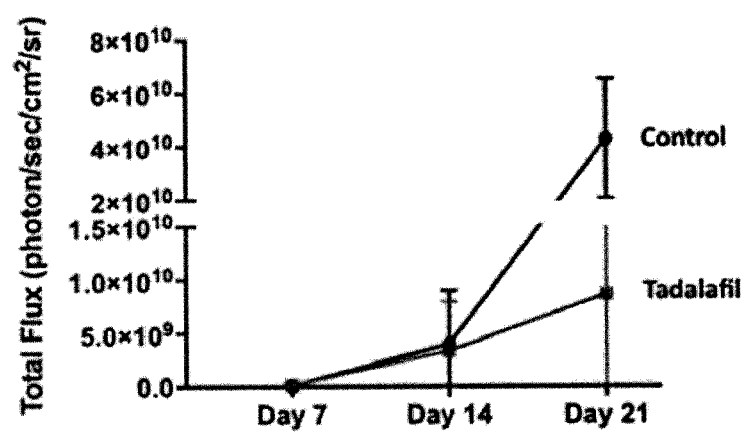
FIG. 35B is a graph showing analysis of the BLI images of FIG. 35A.

FIG. 35A is as image showing RIL-175 hepatoma cells ($5\times10^5/20$ μL) orthotopically implanted into the livers of male B6(Cg)-$Tyr^{c-2J}$/J mice. The establishment and growth of tumors were blindly monitored by bioluminescence (BLI) with the Xenogen IVIS. Darker shading of BLI represents proliferation rate through luciferase total flux signals. They were followed for 21 days. Tadalafil (2 mg/kg), a PDE5 inhibitor, was daily administered i.p. in tumor bearing mice. Analysis of the BLI images of FIG. 35A was carried out by Living Image 2.50 software (PerkinElmer, Waltham, Mass., USA), and calculated ROIs were graphed (FIG. 35B). Accumulation of intrahepatic tumoral myeloid derived suppressor cells (MDSCs) was determined by flow cytometry (FIG. 35C).

Figure 35C:
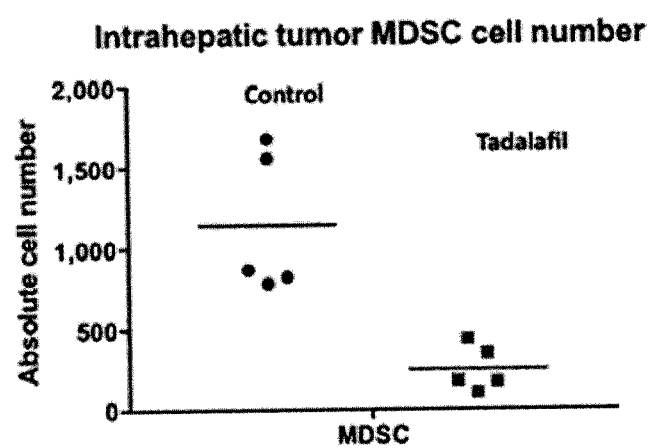
FIG. 35C is a dot plot showing accumulation of intrahepatic tumoral myeloid derived suppressor cells (MDSCs) determined by flow cytometry.

The treatment with a PDE5 inhibitor, tadalafil, caused suppression of tumor growth by reversing MDSC suppressor function and number (FIGS. 35A-35C).

Figure 36A:
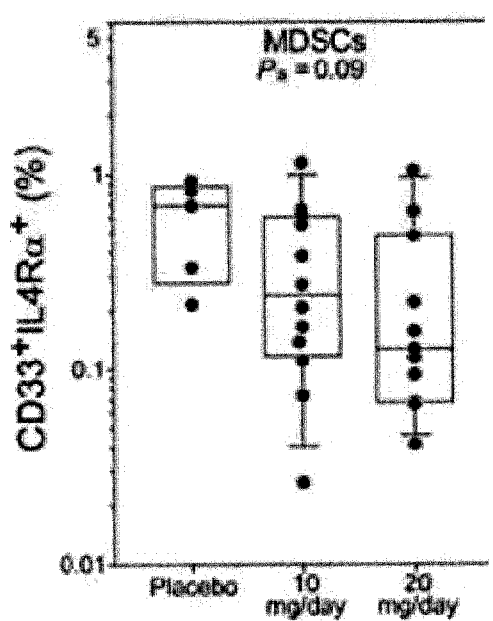
FIG. 36A is a graph showing CD33/IL4Rα intratumoral concentration evaluated by immune-fluorescence microscopy in head and neck squamous cell carcinoma (HNSCC).
Figure 36B:
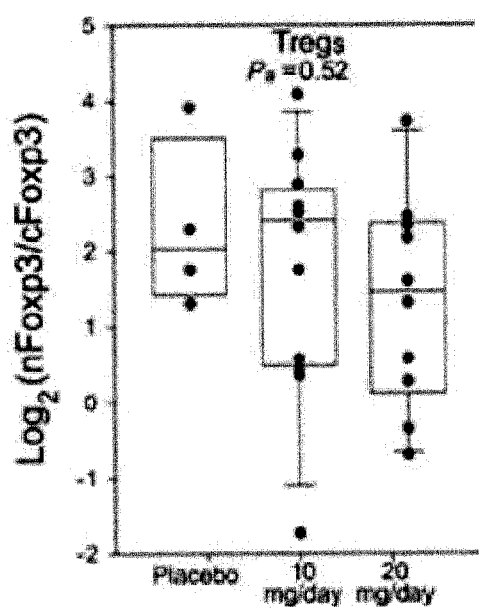
FIG. 36B is a graph showing CD4/FoxP3 intratumoral concentration evaluated by immune-fluorescence microscopy in HNSCC.
Figure 36C:
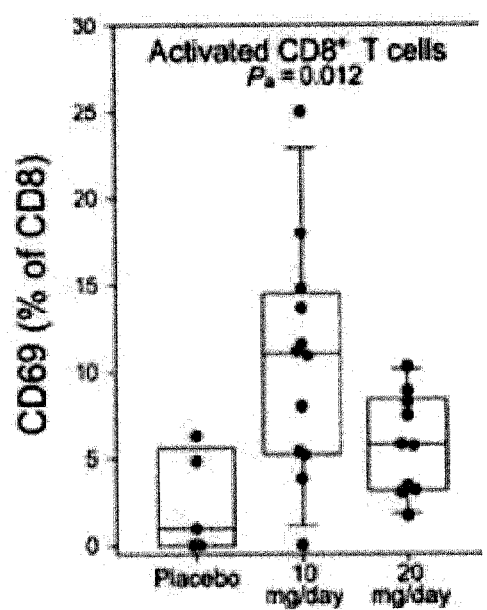
FIG. 36C is a graph showing CD8/CD69 intratumoral concentration evaluated by immune-fluorescence microscopy in HNSCC.

CD33/IL4Rα (FIG. 36A), CD4/FoxP3 (FIG. 36B), and CD8/CD69 (FIG. 36C) intratumoral concentration were evaluated by immune-fluorescence microscopy in HNSCC.

Based on the above, tadalafil modulates tumor microenvironment and depletes it of cells with immune suppressor function.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A set comprising vancomycin and a checkpoint inhibitor, wherein the checkpoint inhibitor is the programmed death 1 (PD-1) inhibitor nivolumab, wherein the vancomycin is the sole antibiotic, wherein the set further comprises a primary bile acid, and wherein the primary bile acid is taurocholic acid (TCA), β-muricholic acid (β-MCA), tauro-β-muricholic acid (T-β-MCA), or chenodeoxycholic acid (CDCA).

2. The set according to claim 1, wherein the set further comprises a phosphodiesterase type 5 (PDE5) inhibitor.

3. The set according to claim 2, wherein the PDE5 inhibitor is tadalafil.

4. A method of treating an adverse condition of the liver of a human subject, the method comprising administering to the subject an effective amount of a set comprising vancomycin and a checkpoint inhibitor, wherein the vancomycin is the sole antibiotic, wherein the set further comprises a primary bile acid, and wherein the primary bile acid is taurocholic acid (TCA), β-muricholic acid (β-MCA), tauro-β-muricholic acid (T-β-MCA), or chenodeoxycholic acid (CDCA).

5. The method according to claim 4, wherein the checkpoint inhibitor is a programmed death 1 (PD-1) inhibitor.

6. The method according to claim 5, wherein the PD-1 inhibitor is nivolumab.

7. The method according to claim 4, wherein the set further comprises a phosphodiesterase type 5 (PDE5) inhibitor.

8. The method according to claim 7, wherein the PDE5 inhibitor is tadalafil.

9. The method according to claim 4, wherein the adverse condition is tumor growth, tumor metastasis, or autoimmune disease.

10. The method according to claim 9, wherein the autoimmune disease is Type 1 diabetes, allergic encephalomyelitis, arthritis, systemic lupus erythematosus, inflammatory colitis, or Graves's thyroiditis.

11. The method according to claim 4, wherein the adverse condition is liver metastasis or hepatocellular carcinoma (HCC).

12. The method according to claim 4, wherein the primary bile acid is formulated for direct absorption by the intestine, formulated for protection from intestinal enzymes, or both.

13. The method according to claim 4, wherein the method further comprises separately administering a substance in addition to the set comprising the vancomycin, checkpoint inhibitor, and primary bile acid, wherein the substance inhibits immunosuppression or elicits an immune response.

* * * * *